United States Patent [19]
Welch
[11] Patent Number: 4,465,506
[45] Date of Patent: Aug. 14, 1984

[54] HERBICIDAL N-[HETEROCYCLICAMINOCARBONYL]-1H-INDENE AND TETRAHYDRONAPHTHALENE SULFONAMIDES

[75] Inventor: John T. Welch, Albany, N.Y.
[73] Assignee: E. I. DuPont de Nemours and Company, Wilmington, Del.

[21] Appl. No.: 440,209
[22] Filed: Nov. 10, 1982

Related U.S. Application Data

[63] Continuation-in-part of Ser. No. 331,891, Dec. 17, 1981, abandoned.

[51] Int. Cl.[3] .................... A01N 43/54; A01N 43/64; A01N 43/66; A01N 43/90

[52] U.S. Cl. .................... 71/92; 71/93; 544/211; 544/212; 544/253; 544/278; 544/321; 544/332; 548/265

[58] Field of Search .................... 71/92, 93; 544/211, 544/212, 278, 253, 321, 332; 548/265

[56] References Cited

U.S. PATENT DOCUMENTS 4,127,405 11/1978 Levitt .................... 71/93
4,370,479 1/1983 Levitt .................... 544/278

FOREIGN PATENT DOCUMENTS 0079683 5/1983 European Pat. Off. .

*Primary Examiner*—Paul M. Coughlan, Jr.

[57] ABSTRACT

N-[Heterocyclicaminocarbonyl]-1H-indene and tetrahydronaphthalene sulfonamides, such as 2,3-dihydro-N-[(4,6-dimethoxypyrimidin-2-yl)aminocarbonyl]-1H-indene-4-sulfonamide, are useful for the regulation of plant growth and as preemergent and postemergent herbicides.

26 Claims, No Drawings

HERBICIDAL N-[HETEROCYCLICAMINOCARBONYL]-1H-INDENE AND TETRAHYDRONAPHTHALENE SULFONAMIDES

RELATED APPLICATION

This application is a continuation-in-part of my copending application U.S. Ser. No. 331,891, filed Dec. 17, 1981, now abandoned.

BACKGROUND OF THE INVENTION

This invention relates to herbicidal 1H-indene and tetrahydronaphthalene sulfonamides which are useful as general or selective herbicides, both pre-emergence and post-emergence.

U.S. Pat. No. 4,127,405 teaches compounds which are useful for controlling weeds in wheat having the formula:

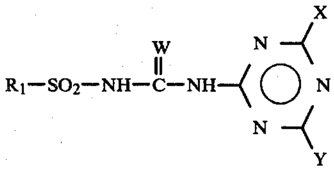

(I)

wherein $R_1$ is

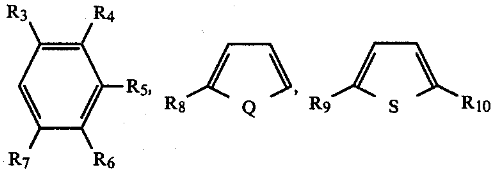

or

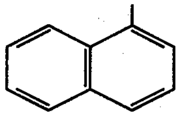

;

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$- or $CH_3CH_2S(O)_n$-;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$- or $CH_3OCH_2$-; and Y is methyl or mehthoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

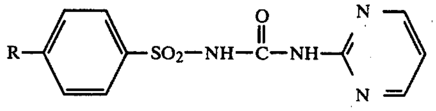

wherein

R=H, halogen, $CF_3$ or alkyl.

Logemann et al., Chem. Ab., 53, 18052 g (1959), disclose a number of sulfonamides, including uracil derivatives and those having the formula:

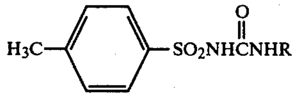

wherein

R is butyl, phenyl or

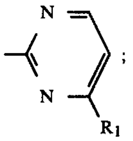

;

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) (Chem. Ab., 59 1633 e) describes the synthesis of N-[(2,6-dimethoxypyrimidin-4yl)aminocarbonyl]-4-methylbenzenesulfonamide:

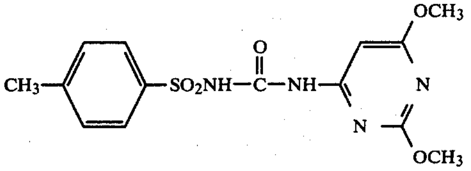

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

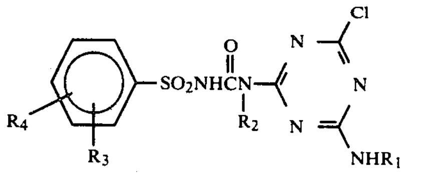

(i)

wherein $R_1$ and $R_2$ may independently be alkyl of 1-4 carbon atoms; and $R_3$ and $R_4$ may independently be hydrogen, chlorine or alkyl of 1-4 carbon atoms.

Compounds of Formula (ii), and their use as antidiabetic agents, are reported in *J. Drug. Res.* 6, 123 (1974),

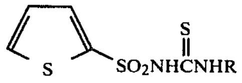

(ii)

wherein

R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to compounds of Formulae I, II, and III, suitable agricultural compositions containing them, and their methods of use as general and/or selective pre-emergent and/or post-emergent herbicides.

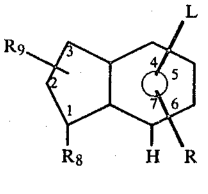

I

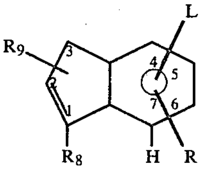

II

-continued

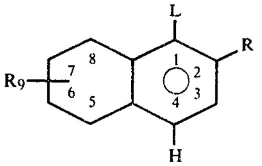

III wherein

L is

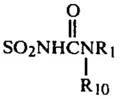

R is H, Cl, Br, $NO_2$, $QR_2$, $CO_2R_3$, $SO_3NR_5R_6$, $SO_2N(OCH_3)CH_3$, $OSO_2R_7$ or $C_1$–$C_3$ alkyl;

$R_2$ is $C_1$–$C_3$ alkyl, $CF_2H$, $CF_3$ or $CF_2CF_2H$;

$R_3$ is $C_1$–$C_3$ alkyl, $CH_2CH{=}CH_2$, $CH_2CH_2OCH_3$ or $CH_2CH_2Cl$;

$R_5$ and $R_6$ are independently $C_1$–$C_2$ alkyl;

$R_7$ is $C_1$–$C_3$ alkyl or $CF_3$;

$R_8$ is H, $CH_3$or Cl;

$R_9$ is H or $CH_3$;

$R_{10}$ is H or $CH_3$;

Q is O, S or $SO_2$;

$R_1$ is

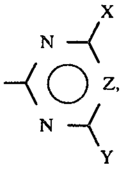

,

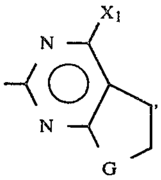

,

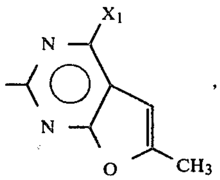

,

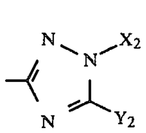

or

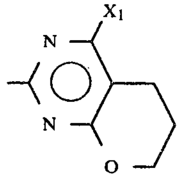

X is $CH_3$, $OCH_3$ or Cl;

Y is $CH_3$, $C_2H_5$, $OCH_3$, $OC_2H_5$, $CH_2OCH_3$, $NH_2$, $NHCH_3$, $SCH_3$, $CH(OCH_3)_2$;

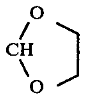

or $N(CH_3)_2$;

Z is CH or N;

$X_1$ is $CH_3$ or $OCH_3$;

G is O or $CH_2$;

$X_2$ is $C_1$-$C_3$ alkyl or $CH_2CF_3$; and $Y_2$ is $SCH_3$, $SC_2H_5$, $OCH_3$ or $OC_2H_5$.

and their agriculturally suitable salts; provided that (1) in Formula I, L is not in the 6-position;

(2) in Formula I, when L is in the 4-position and R is in the 6-position, then R is H, Cl, Br, $NO_2$, $CH_3$ or $OCH_3$;

(3) in Formula II, when $R_8$ is Cl, then R is other than $C_1$-$C_3$ alkyl; and (4) when X is Cl, then Z is CH and Y is $NH_2$, $NHCH_3$, $N(CH_3)_2$ or $OCH_3$.

Preferred for reasons of their higher herbicidal activity and/or more favorable ease of synthesis are:

(1) Compounds of the generic scope of Formula I;
(2) Compounds of the generic scope of Formula II;
(3) Compounds of the generic scope of Formula III;
(4) Compounds of Preferred (1) where L is fixed at the 4-position and $R_9$ is at the 2 or 3 position;
(5) Compounds of Preferred (4) where R is fixed at the 5-position and $R_{10}$ is H;
(6) Compounds of Preferred (5) where $R_1$ is

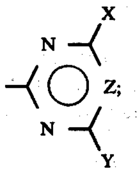

(7) Compounds of Preferred (6) where R is $CO_2CH_3$, $SO_2CH_3$, $SO_2N(CH_3)_2$, Cl, $NO_2$, $OSO_2CH_3$, $OCF_2H$, $SCF_2H$ or H.

Specifically preferred are:

2,3-dihydro-N-[(4,6-dimethoxypyrimidin-2-yl)aminocarbonyl]-1H-indene-4-sulfonamide;
2,3-dihydro-N-[(4,6-dimethylpyrimidin-2-yl)aminocarbonyl]-1H-indene-4-sulfonamide;
2,3-dihydro-N-[(4-methoxy-6-methylpyrimidin-2-yl)aminocarbonyl]-1H-indene-4-sulfonamide;
2,3-dihydro-N-[(4,6-dimethoxy-1,3,5-triazin-2-yl)aminocarbonyl]-1H-indene-4-sulfonamide;
2,3-dihydro-N-[(4,6-dimethyl-1,3,5-triazin-2-yl)aminocarbonyl]-1H-indene-4-sulfonamide; and
2,3-dihydro-N-[(4-methoxy-6-methyl-1,3,5-triazin-2-yl)aminocarbonyl]-1H-indene-4-sulfonamide.

SYNTHESIS

Many of the compounds of Formulae I, II or III may be prepared as shown in Equation 1 by the reaction of an appropriately substituted sulfonyl isocyanate, $L_1SO_2NCO$ wherein $L_1$ is a radical selected from:

(Ia)

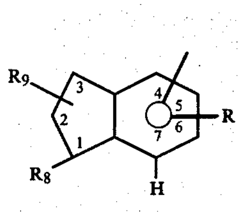

(IIa)

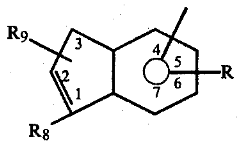

(IIIa)

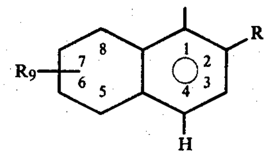

and the appropriate heterocyclic amine $R_1R_{10}NH$ (V); R, $R_1$, $R_8$, $R_9$ and $R_{10}$ being as previously defined.

EQUATION 1

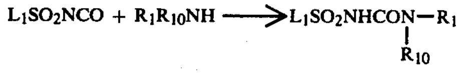

(IV) (V) (Ib, IIb, IIIb)

The reaction of Equation 1 is generally carried out by adding a solution of the sulfonyl isocyanate (IV) in an inert solvent such as methylene chloride or acetonitrile to a suspension or solution of the heterocyclic amine (V) in the same solvent under anhydrous conditions. Since the sulfonyl isocyanate (IV) is usually a liquid or readily soluble in the solvent used, it is usually convenient to add this to a suspension or solution of the amine. The mixture is then stirred from one to sixteen hours at temperatures from ambient to the reflux temperature of the solvent used. In some cases, the reaction is exothermic and the products crystallize from the reaction mixture on cooling. When the product is soluble in the reaction medium it can be isolated by evaporation of the solvent and trituration with a suitable solvent such as 1-chlorobutane, hexane or similar non-polar solvent.

Sulfonyl isocyanates can be prepared by the reaction of sulfonamides of structure IVa with phosgene in the presence of an alkyl isocyanate such as butyl isocyanate in an inert solvent, such as chlorobenzene or xylene, by the procedure of H. Ulrich and A. A. Y. Sayigh (Newer Methods of Preparative Organic Chemistry, Vol. VI, p. 233–41, Academic Press, New York and London, W. Foerst, Ed.) as shown by Equation 2.

EQUATION 2

$$L_1SO_2NH_2 + COCl_2 \xrightarrow[\text{xylene}]{C_4H_9NCO} L_1SO_2NCO$$

(IVa) (IV)

An alternative procedure for the preparation of the sulfonylureas of this invention is via the reaction of a carbamate of structure IVb with a heterocyclic amine (V) by the procedure of W. Meyer and W. Forg, EPO 44,807 as shown in Equation 2a.

EQUATION 2a

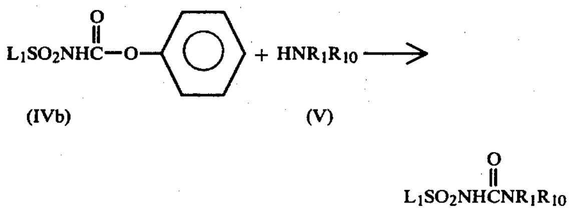

(IVb) (V)

(Ib, IIb, IIIb)

The carbamates of structure IVb can be prepared by methods also described by M. Meyer and W. Forg (op. cit).

Alternatively, many of the sulfonylureas of this invention may be prepared by the reaction of sulfonamides of Formula IVa with heterocyclic isocyanates of Formula Va followed by replacement of the active halogens on the hetero ring as shown by the sequence in Equation 3.

EQUATION 3

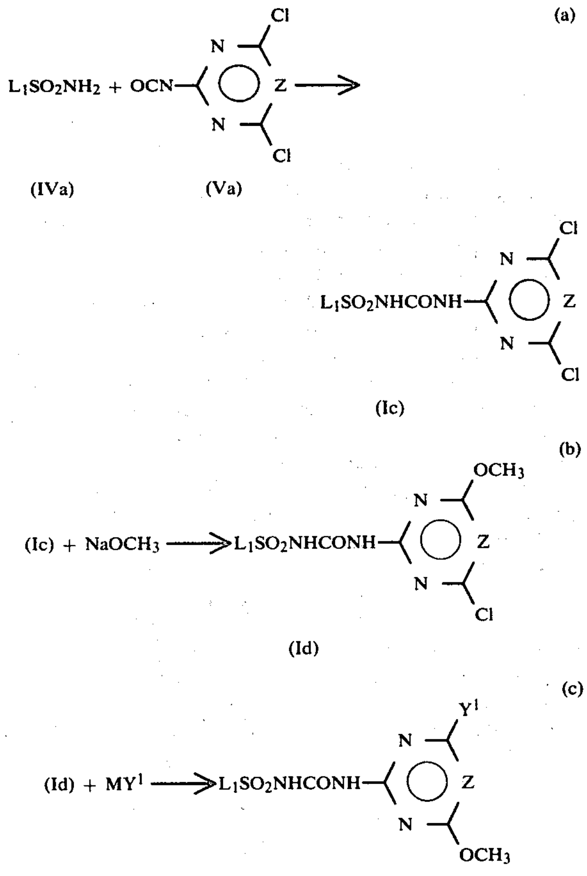

(IVa) (Va)

(Ic)

(Id)

(Ie)

In Equation 3, $L_1$ and Z are as previously defined, $Y^1$ is $OCH_3$, $OC_2H_5$, $NH_2$, $NHCH_3$ or $N(CH_3)_2$ and M is H or an alkali metal cation. In Reaction Step (3a), an appropriately substituted sulfonamide is reacted with a heterocyclic isocyanate of Formula Va to yield a sulfonylurea of Formula Ic. The heterocyclic isocyanates used in Reaction 3a may be prepared according to the method described in Swiss Pat. No. 579,062; U.S. Pat. No. 3,919,228, U.S. Pat. No. 3,732,223 and *Angew Chem. Int. Ed.*, 10, 402 (1976), the disclosures of which are herein incorporated by reference.

In Reaction Step (3a), an appropriately substituted sulfonamide is contacted with a heterocyclic isocyanate of Formula Va in the presence of an inert organic solvent such as methylene chloride, tetrahydrofuran, acetonitrile, acetone or butanone. Optionally, a catalytic amount of a base such as 1,4-diazabicyclo[2.2.2]octane (DABCO), potassium carbonate or sodium hydroxide may be added to the reaction mixture.

In Reaction Steps (3b) and (3c), one or two of the chlorine atoms on the pyrimidinyl or triazinyl ring of the compound of Formula Ic is displaced by an alcohol or amine (3c). Generally, this may be done by contacting the compound of Formula Ic with methanol or methoxide. Thus, in Reaction Step (3b), a compound of Formula Ic may be contacted with at least one equivalent of methanol. This reaction is sluggish, however, and it is preferred to contact the compound of Formula Ic with at least two equivalents of sodium methoxide in acetonitrile, THF or dimethylformamide.

It should be noted that two equivalents of methoxide are required for Reaction Step (3b) whereas only one equivalent of methanol is needed for the same process. When methoxide is used, the first equivalent of base removes a proton from the sulfonyl nitrogen, and it is only the second equivalent which effects displacement of the halogen. As a result, two equivalents of methoxide are required. The resulting salt must be acidified, e.g., with sulfuric, hydrochloric or acetic acid, to yield a compound of Formula Id. Applicant, of course, does not intend to be bound by the mechanism described above.

In Reaction Step (3c), a compound of Formula Id is contacted with either one equivalent of alkanol, $CH_3OH$ or $C_2H_5OH$, or with two equivalents of alkoxide, $CH_3O$— or $C_2H_5O$— or two equivalents of $NH_3$, $H_2NCH_3$ or $HN(CH_3)_2$.

Sulfonyl chlorides and sulfonamides of 1,2,3,4-tetrahydronaphthalene and 2,3-dihydro-1H-indene are well known in the art (c.f. Organic Chemistry of Sulfur, p. 484, C. M. Suter, John Wiley and Sons, New York, 1944). The preparation of sulfonamides of Formula IVa from the corresponding sulfonyl chlorides may be carried out using methods widely reported in the literature [e.g., Crossley et al., *J. Am. Chem. Soc.*, 60, 2223 (1938); or Cross et al., *J. Med. Chem.*, 21, 348 (1978)]. Sulfonyl chlorides may be prepared, for example, by direct chlorosulfonation of the aromatic ring using chlorosulfonic acid according to the method of R. T. Arnold and H. E. Zaugg, (*J. Am. Chem. Soc.*, 63, 1317-20 (1941)).

Sulfonation also may be carried out with sulfuric acid according to the procedure of A. Courtin, *Helv. Chim. Acta.*, 64, 572-78 (1981). The sulfonic acid thus obtained may be converted to the sulfonyl chloride by treatment with thionyl chloride, phosphorus trichloride or phosphorus pentachloride according to W. A. Gregory, U.S. Pat. No. 2,888,486. Alternatively, appropriately substituted amines, may also be converted to sulfonyl chlorides by preparing their diazonium chlorides and treating these with sulfur dioxide in the presence of a copper salt.

The preparation of 1,2,3,4-tetrahydro-5-nitronaphthalene-4-sulfonyl chloride via the diazonium chloride salt route (Equation 4) was reported by Courtin (op. cit.)

EQUATION 4

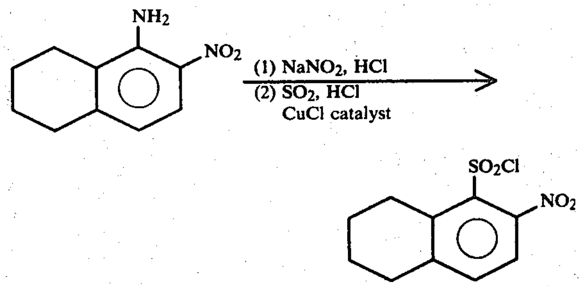

Nitration of 2,3-dihydro-1H-indene sulfonic acid derivatives, following the procedure of H. V. B. Joy and M. T. Bogart, *J. Org. Chem.*, 1, 236-244 (1936) and J. Hornya, et al., *Czech*, 155,849 (15, Nov. 1974). 2,3-Dihydro-1H-indene-4-sulfonyl chloride yields the 6-nitrc derivative and 2,3-dihydro-1H-indene-5-sulfonic acid yields a mixture of the 4,6- and 7-nitro derivatives which can be separated by fractional crystallization of the potassium salts.

Substituted benzenepropionic acids and benzenebutyric acids may be converted to 2,3-dihydro-1H-indenes and 1,2,3,4-tetrahydronaphthalene derivatives as shown in Equation 5 according to the procedure of M. Olivier and E. Marechal (*Bull. Soc. Chim. Fr.*, 1973, 3092), wherein R is Cl, Br, $OR_2$, $SR_2$ or $C_1$-$C_3$ alkyl and $R_2$ is as previously defined.

EQUATION 5

(a)

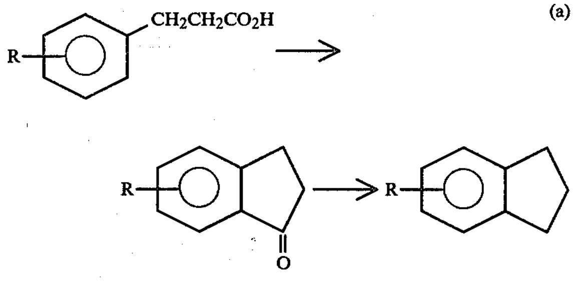

(b)

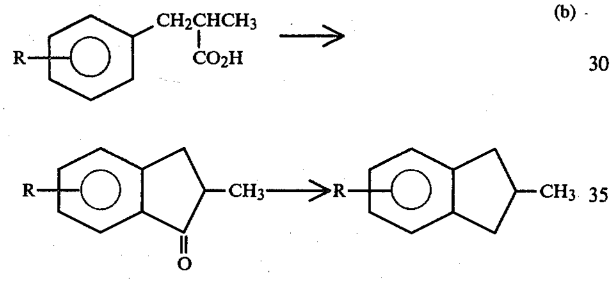

(c)

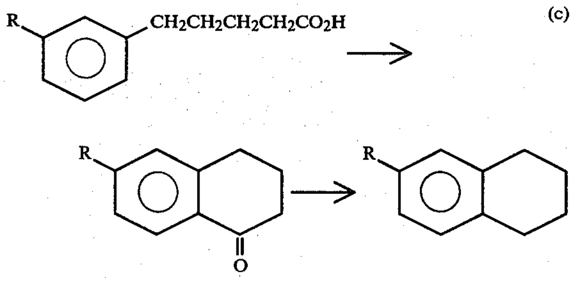

The intermediates obtained by the procedure of Equation 5 can be sulfonated or chlorosulfonated by the procedures previously described.

Nitro-2,3-dihydro-1H-indenylamines such as those reported by R. T. Arnold and J. Richter, *J. Am. Chem. Soc.*, 70, 3505 (1948) and J. Majer et al., Czech. 152238 (15, Feb. 1974) C. A. 82, 97885 (1975) and 1,2,3,4-tetrahydro-4-nitro-5-naphthyl amine can be diazotized according to the procedure of A. Courtin (op. cit.) and the salt thus obtained can be reacted to obtain derivatives wherein the amino group has been replaced by R' where R'=Br, Cl, SH, $SO_2Cl$, CN or OH moieties as shown in Equation 6 by methods described by D. S. Wulfman (The Chemistry of Diazonium Salts, Part I, pages 274–312, Saul Patai, Editor, John Wiley and Sons, New York, 1978) or Courtin (op. cit.).

EQUATION 6

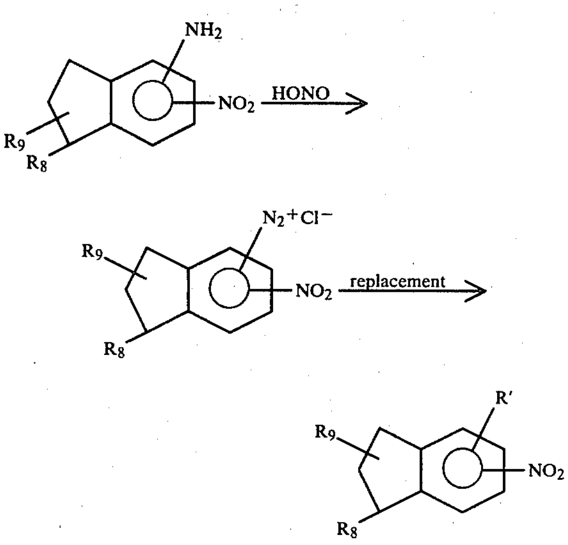

The intermediates thus prepared wherein R' is OH or SH can be alkylated by methods well known in the art to obtain derivatives where R' is $OR_2$ or $SR_2$. The thioethers thus obtained can be oxidized to yield intermediates with the $SO_2R_2$ moiety by warming the thioethers in acetic acid containing excess 30% hydrogen peroxide. In those instances where R'=$SO_2Cl$, those moieties can be converted to $SO_2NR_5R_6$ or $SO_2N(OCH_3)CH_3$ by methods well known in the art, such as Crossley et al. (op. cit.) or Cross et al. (op. cit.). Reaction of the intermediates where R'=OH with $R_7SO_2Cl$ in the presence of a base such as triethylamine yields intermediates with the $R_7SO_2O$-moiety.

Intermediates wherein R' is $CO_2R_3$ can be prepared from compounds where R' is CN by methods well known in the art. Hydrolysis of the nitrile group by aqueous sodium hydroxide yields the sodium salt of the acid (R' is $CO_2Na$) which can be converted to the desired carboxylic ester (where R' is $CO_2R_3$) by refluxing the product from the hydrolysis with the appropriate alcohol in the presence of a mineral acid.

As shown in Equation 7, the substituted 2,3-dihydro(4- , 5- or 6-)nitro-1H-indenes and 1,2,3,4-tetrahydro-5-nitronaphthalenes obtained above can be reduced to the corresponding amines which can be converted in turn to the desired sulfonyl chlorides.

EQUATION 7

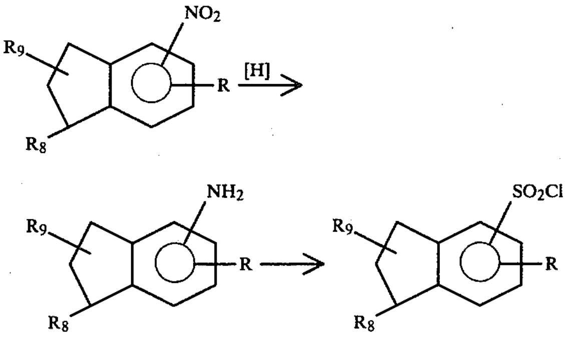

Reaction with hydrogen at a pressure of 100 to 1000 p.s.i.g. at a temperature of 80° to 150° in the presence of a suitable catalyst such as palledium, nickel or platinum in a solvent, such as ethanol, ethyl acetate or dimethylformamide, yields the desired substituted (4-, 5- or 6-(amino-2,3-dihydro-1H-indenes or 4-amino-1,2,3,4-tetrahydronaphthalenes. The product can be converted to the corresponding 2,3-dihydro-1H-indenyl-4-, 5- or 6-sulfonyl chlorides or 1,2,3,4-tetrahydronaphthyl-4-sulfonyl chloride via diazotization of the amine followed by reaction of the diazonium salt with sulfur dioxide and hydrochloric acid in the presence of cuprous or cupric chloride by the procedure of Courtin (op. cit.).

Using methods described in *Organic Synthesis,* V. 2, pages 924-5, V. Midrigician, Reinhold Publ. Co., New York, 1960, the 2,3-dihydro-1H-indenyl-(4-, 5- or 6-)sulfonamide intermediates prepared according to the above methods can be converted to the corresponding 1H-indenyl-(4-, 5- or 6-)sulfonamides by contacting the appropriate 2,3-dihydro derivative with a N-halogenated imide such as N-bromosuccinimide (NBS) followed by dehalogenation as shown in Equation 8 wherein R, $R_8$ and $R_9$ are as previously defined.

EQUATION 8

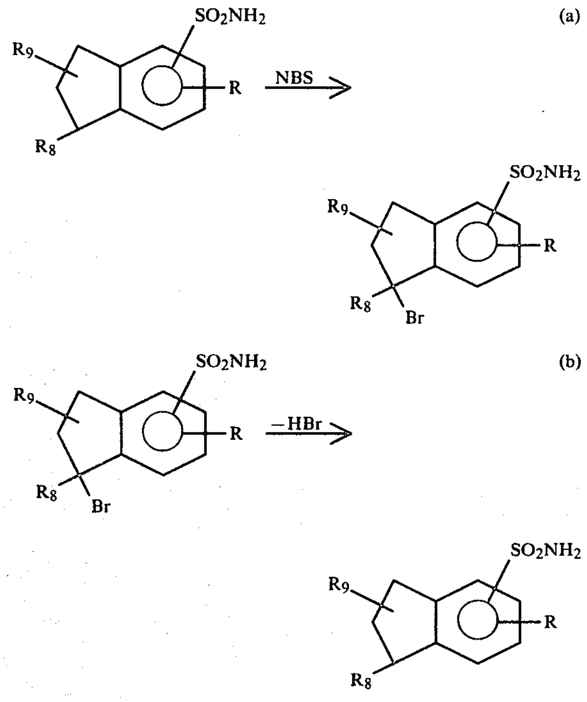

3-Chloro-1H-indene-7-sulfonyl chloride may be prepared by the chlorination of 2,3-dihydro-1H-indene-4-sulfonyl chloride with chlorine oxide in carbon tetrachloride as described in Example 9.

The synthesis of pyrimidine and triazine amines of Formula V has been reviewed in "The Chemistry of Heterocyclic Compounds," a series published by Interscience Publishers, Inc., N.Y. and London. 2-Aminopyrimidines are described by D. J. Brown in "The Pyrimidines," Vol. 26 of this series. The 2-amino-1,3,5-triazines are reviewed by K. R. Huffman in "The Triazines" of this same series. The synthesis of triazines is also described by F. C. Schaefer, U.S. Pat. No. 3,154,547, and by K. R. Huffman and F. C. Schaefer, *J. Org. Chem.,* 28, 1816 (1963).

Braker, Sheehan, Spitzmiller and Lott, *J. Am. Chem. Soc.,* 69, 3072 (1947) describe the preparation of 6,7-dihydro-4-methoxy-5H-cyclopentapyrimidin-2-amine by the following sequence of reactions.

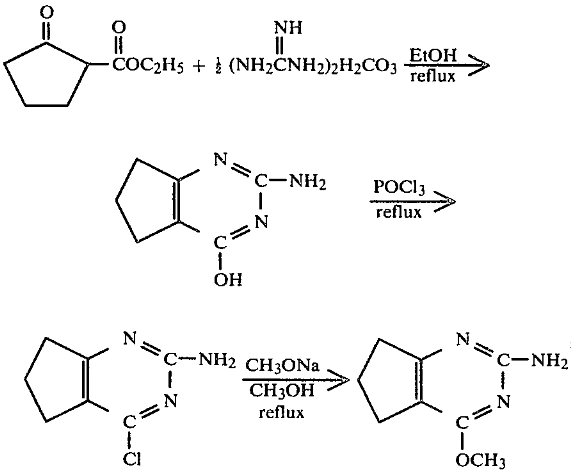

6,7-dihydro-4-methoxy-5H—cyclopentapyrimidin-2-amine.

An analogous sequence of reactions can be used to prepare 5,6,7,8-tetrahydro-4-methoxy-2-quinazolinamine.

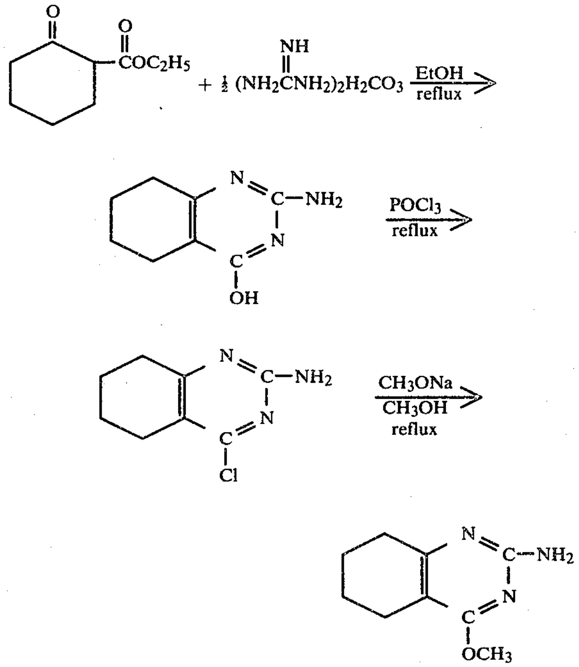

5,6,7,8-tetrahydro-4-methoxy-2-quinazolinamine.

Mitter and Bhattacharya, *Quart. J. Indian Chem. Soc.,* 4, 152 (1927) describe the preparation of 5,6,7,8-tetrahydro-4-methyl-2-quinazolinamine as follows:

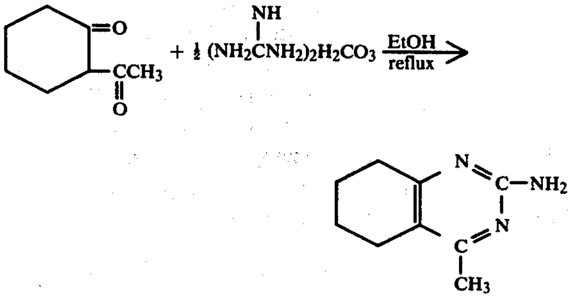

5,6,7,8-tetrahydro-4-methyl-2-quinazolinamine.

Similarly, 6,7-dihydro-4-methyl-5H-cyclopentapyrimidin-2-amine can be prepared by the condensation of 2-acetylcyclopentanone with guanidine carbonate, but preferably under acidic conditions, removing the water formed.

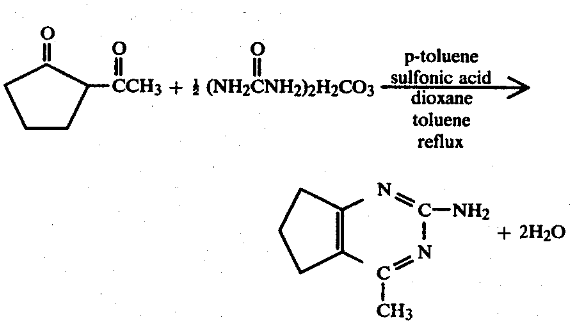

6,7-dihydro-4-methyl-5H—cyclopentapyrimidin-2-amine.

Shrage and Hitchings, *J. Org. Chem.*, 16, 1153 (1951) describe the preparation of 5,6-dihydro-4-methylfuro[2,3-d]pyrimidin-2-amine by the following sequence of reactions

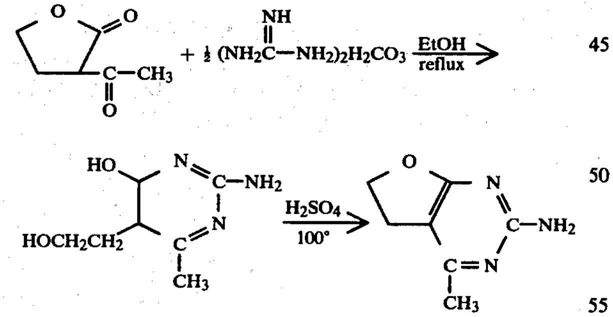

An analogous sequence of reactions can be used to prepare 6,7-dihydro-4-methyl-5H-pyrano[2,3-d]pyrimidin-2-amine starting with 2-acetyl-8 valerolactone (Korte and Wusten, *Tetrahedron* 19, 1423 (1963)).

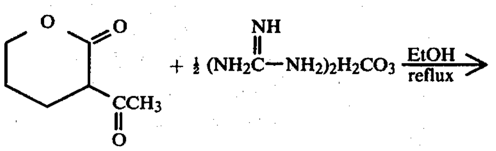

-continued

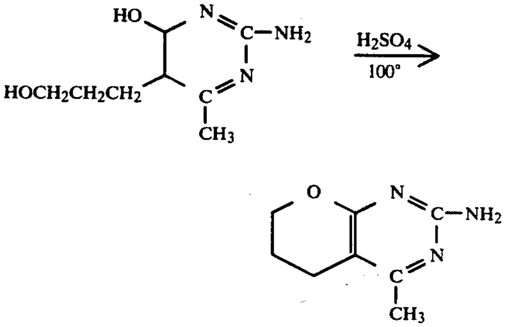

5,6-Dihydro-4-methoxyfuro[2,3-d]pyrimidin-2-amine can be prepared by the method of Braker et al., *J. Am. Chem. Soc.*, 69, 3072 (1947), using 5,6-dihydro-4-hydroxyfuro[2,3-d]pyrimidin-2-amine (Svab, Budesinski and Vavrina, *Collection Czech. Chem. Commun.*, 32, 1582 (1967)).

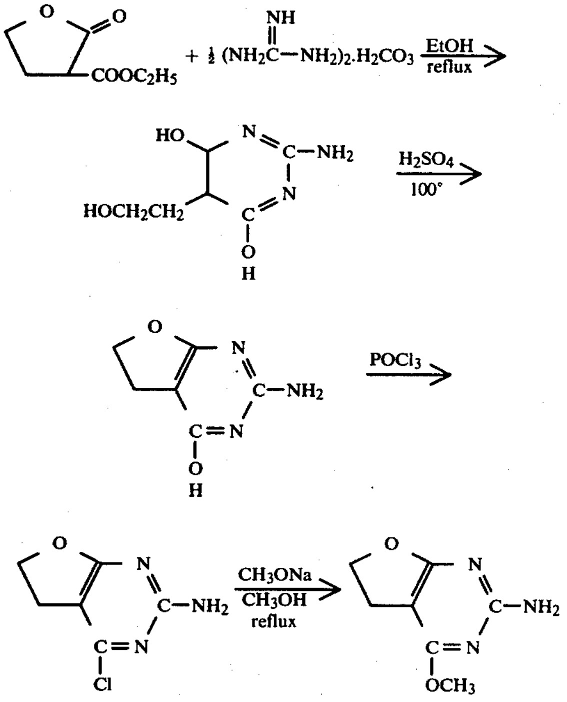

An analogous sequence of reactions can be used to prepare 6,7-dihydro-4-methoxy-5H-pyrano[2,3-d]pyrimidin-2-amine.

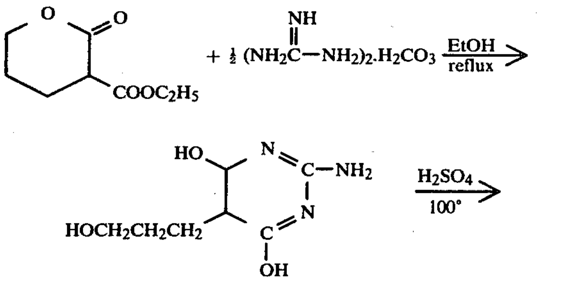

-continued

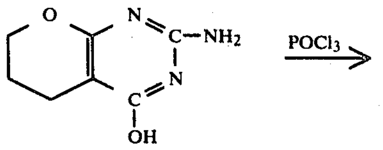

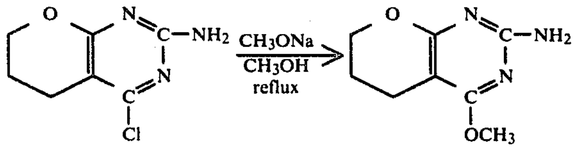

Caldwell, Kornfeld and Donnell, *J. Am. Chem. Soc.*, 63, 2188 (1941), describe the preparation of 6,7-dihydro-5H-cyclopentapyrimidin-2-amine by the following sequence of reactions.

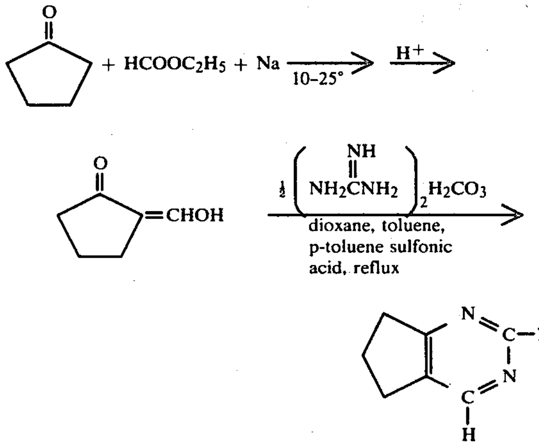

Fissekis, Myles and Brown, *J. Org. Chem.*, 29, 2670 (1964), describe the preparation of 2-amino-4-hydroxy-5-(2-hydroxyethyl)pyrimidine which can be converted to 5,6-dihydrofuro[2,3-d]pyrimidin-2-amine by dehydration.

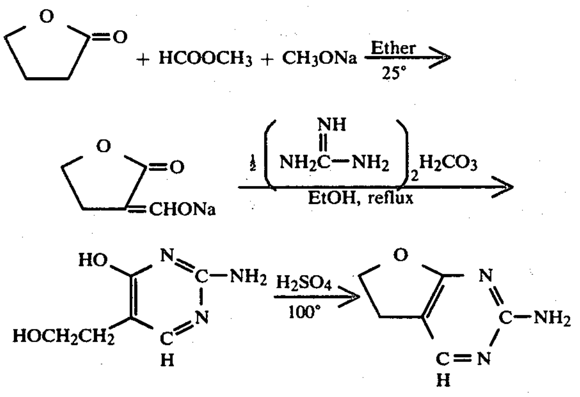

Preparations of 3-amino-1,2,4-triazoles are known in the art and 1,2,4-triazoles are reviewed in *The Chemistry of Heterocyclic Compounds* "Triazoles 1,2,4" (John Wiley and Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature syntheses are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); *Berichte,* 96, 1064 (1963).

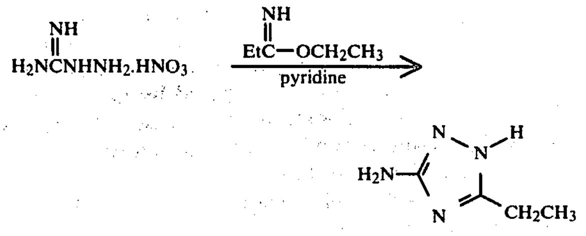

Condensation of hydrazine with ethyl N-cyanoacetimidate yields 3-amino-5-methyltriazole; *Journal of Organic Chemistry,* 28, 1816 (1963).

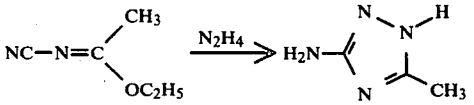

Trifluoromethyl 3-aminotriazole can be obtained by thermal dehydration of the hydrazide of trifluoroacetic acid. *Zh. Obshch. Khim.,* 39, 2525 (1969); *Chemical Abstracts,* 72: 78954v (1970).

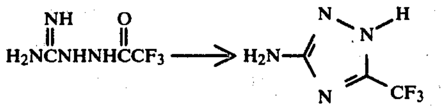

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

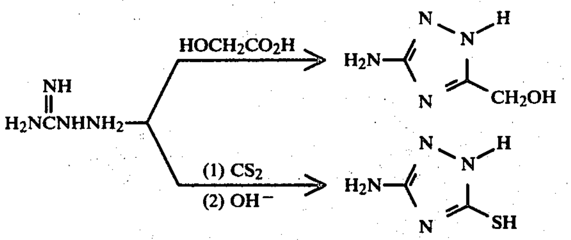

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry,* 39, 1522 (1974).

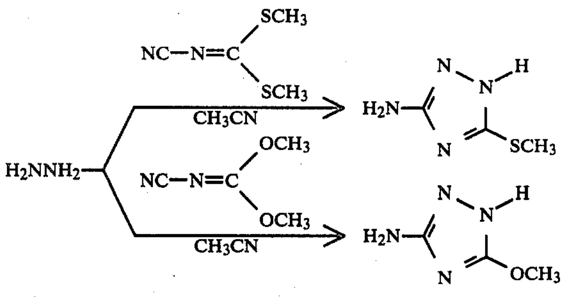

Reaction of substituted hydrazines with N-cyanothioimidocarbonates (prepared according to the procedure given in D. M. Wieland, PH.D. Thesis, 1971, pp. 123–124) yields disubstituted aminotriazoles as shown below.

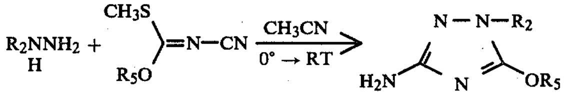

Furo[2,3-d]pyrimidine Intermediates

The pyrimidine intermediates III in which Z is hydrogen or methyl and X is methyl have been reported in the literature by E. Bisagni et al., (*Bul. Soc. Chim. Fr.*, 803 (1969)). An apparently more efficient procedure is depicted in Equation 3 for the case in which Z is hydrogen.

EQUATION 3

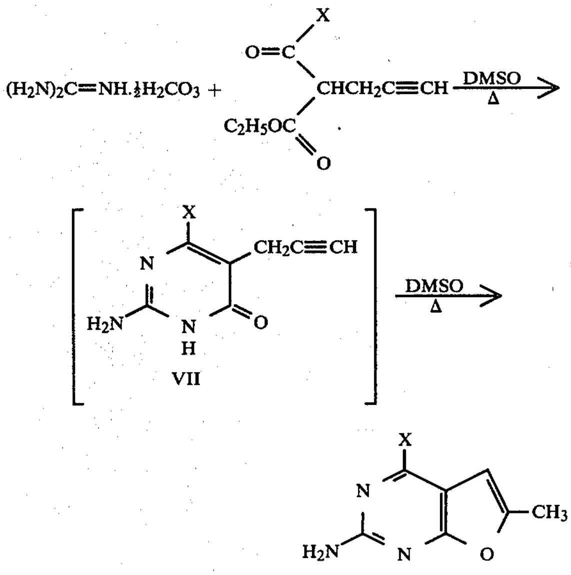

VIII (Z = H)

X = $CH_3$ or $C_2H_5$

The keto-ester precursors VI are prepared by well known literature methods, e.g., J. F. Tinker and T. E. Whatmough, *J. Amer. Chem. Soc.*, 74, 5235 (1952).

Treatment of VI with an excess of guanidine carbonate in an organic solvent, preferably a polar aprotic solvent such as dimethylsulfoxide (DMSO), dimethylformamide (DMF), or N,N-dimethylacetamide, at a temperature of 80° to 200°, preferably 100° to 160°, ambient pressure and preferably under an inert atmosphere, yields both VIII and VII as products. The products are isolated upon dilution of the reaction mixture with, for example, acetone and water successively. Higher reaction temperatures and longer reaction times (e.g., in DMSO at 130°–150° for 2 to 8 hours) favor the production of the furopyrimidine VIII over the uncyclized pyrimidine VII.

Agriculturally suitable salts of compounds of Formulae I, II and III are also useful herbicides and can be prepared in a number of ways known to the art. For example, metal salts can be made by reacting compounds of Formulae I, II and III with a solution of an alkali or alkaline earth metal salt having a sufficiently basic anion (e.g. hydroxide, alkoxide, carbonate or hydride); quaternary amine salts can be made by similar techniques. Detailed examples of such techniques are given in U.S. Pat. No. 4,127,405, the disclosure of which is herein incorporated by reference.

In the following examples, unless otherwise indicated, all parts are by weight and temperatures in °C.

EXAMPLE 1

2,3-Dihydro-5-nitro-1H-indene-4-sulfonyl isocyanate

To 6.05 g of 2,3-dihydro-5-nitro-1H-indene-4-sulfonamide was added with stirring 50 ml of mixed xylenes with 2.47 g of butyl isocyanate and a catalytic amount of 1,4-diazabicyclo[2.2.2]octane (DABCO) at reflux. Phosgene was passed into the mixture slowly under a dry ice cooled reflux condenser until the temperature of the mixture fell to 124° C. The phosgene flow was discontinued until the reflux temperature rose to 134° whereupon the phosgene addition was resumed. Addition of phosgene was continued until the temperature once again fell to 124°. This cycling of phosgene addition was continued until the reflux temperature remained at 120°–124° without further phosgene addition. Evaporation of the butyl isocyanate and xylene under reduced pressure yielded a residue. Infrared analysis of this residue showed a strong absorption peak at 2240 $cm^{-1}$ consistent for sulfonyl isocyanate and the disappearance of the urea carbonyl peak at 1700 $cm^{-1}$ and no NH peaks at 3360 and 3240 $cm^{-1}$. This residue was dissolved in 25 ml of dry methylene chloride and used in the following examples, as stated, without further purification.

EXAMPLE 2

2,3-Dihydro-N-[(4,6-dimethylpyrimidin-2-yl)aminocarbonyl]-5-nitro-1H-indene-4-sulfonamide To 0.615 g of 2-amino-4,6-dimethylpyrimidine in 5 ml of anhydrous methylene chloride, was added with stirring, one fifth of the 2,3-dihydro-5-nitro-1H-indenesulfonyl isocyanate, prepared in the preceding example, which was dissolved in anhydrous methylene chloride. After stirring at reflux, overnight, the solvent was removed by evaporation and the product triturated with chlorobutane and filtered. The solid thus obtained melted at 172° with decomposition and showed infrared absorption peaks at 3230–3160 $cm^{-1}$ (NH); 1700 $cm^{-1}$ (CO); 1540 $cm^{-1}$ ($NO_2$) and 1340–1370, 1160 ($SO_2$) consistent for the desired product. Proton Magnetic Resonance absorption peaks at 7.6–8.0 δ (aromatic CH), 6.9 δ (pyrimidine, 5-CH), 3.6–2.8 δ (cyclic $CH_2$), 2.4 δ ($CH_3$) confirmed the presence of the desired structure.

EXAMPLE 3

2,3-Dihydro-N-[(4-methoxy-6-methylpyrimidin-2-yl)aminocarbonyl]-5-nitro-1H-indene-4-sulfonamide To 0.69 g of 2-amino-4-methoxy-6-methylpyrimidine suspended in 5 ml of anhydrous methylene chloride was added with stirring one fifth of the solution of 2,3-dihydro-5-nitro-1H-indenesulfonyl isocyanate prepared in Example 1. After stirring at reflux for 16 hours, the methylene chloride was removed in vacuo on a rotary evaporator and the residue was triturated with 1-chlorobutane and methylene chloride to yield a solid which decomposed at 75°-93°. This product showed absorption peaks by infrared spectroscopy at 3400 $cm^{-1}$ (NH), 1670 $cm^{-1}$ (CO), 1540 $cm^{-1}$ ($NO_2$) and 1360 $cm^{-1}$ ($SO_2$). The structure was confirmed by Proton Magnetic Resonance absorption peaks at 7.6 ppm (aromatic CH), 6.4 ppm (pyrimidine CH), 2.8-3.6 ppm (cyclic $CH_2$) and 3.9 ppm ($CH_3O$).

EXAMPLE 4

2,3-Dihydro-N-[(4,6-dimethoxypyrimidin-2-yl)aminocarbonyl]-5-nitro-1H-indene-4-sulfonamide To 0.78 g of 2-amino-4,6-dimethoxypyrimidine in 5 ml of anhydrous methylene chloride was added, with stirring, one fifth of the 2,3-dihydro-5-nitro-1H-indenesulfonyl isocyanate prepared in Example 1. The mixture was protected from moisture under nitrogen and heated to reflux for sixteen hours after which the solvent was removed in-vacuo. Trituration of the residual solid with 1-chlorobutane yielded a solid melting at 162°-172°. Infrared spectroscopy analysis of this product showed absorption peaks at 3360 $cm^{-1}$ (NH), 1740 $cm^{-1}$ (C═O), 1540 $cm^{-1}$ ($NO_2$), 1360 and 1160 $cm^{-1}$ ($SO_2$) consistent for the desired structure and also absorption peaks by proton magnetic resonance at 7.5-7.7 ppm (aromatic CH), 6.0 ppm (pyrimidine CH), 3.9 ppm ($OCH_3$), 3.6-2.8 ppm (cyclic $CH_2$) confirmed the presence of the desired structure.

EXAMPLE 5

N-Butylaminocarbonyl-5,6,7,8-tetrahydronaphthalene-1-sulfonamide

To 10.9 g of 5,6,7,8-tetrahydronaphthalene-1-sulfonamide dissolved in 25 ml of anhydrous acetonitrile was added 6.13 g of n-butyl isocyanate and the mixture was heated to reflux with stirring for 16 hours. The mixture was then filtered and concentrated in vacuo to an oil which solidified to yield 15.5 g of the desired product melting at 173°-175°. The structure was confirmed by infrared absorption peaks at 1680 $cm^{-1}$ (CO) and 3350 $cm^{-1}$ (NH) and proton magnetic absorption peaks at 7.2-8.0 ppm (aromatic CH) and 1-3.2 ppm ($CH_2$).

EXAMPLE 6

5,6,7,8-Tetrahydronaphthalene-1-sulfonyl isocyanate

Into a solution of 15.5 g of N-butylaminocarbonyl-5,6,7,8-tetrahydronaphthalene-1-sulfonamide, and a catalytic amount of 1,4-diazabicyclo[2.2.2]octane dissolved in 50 ml of mixed xylenes at reflux (133°) was added enough phosgene to cause the reflux temperature to drop to 120°-124° C. The addition of phosgene was discontinued until the temperature rose to 130°. Additional phosgene was added until the reflux temperature was depressed to 120°-124° whereupon the phosgene addition was again halted. The cycling of the phosgene addition was continued until the reflux temperature remained at 120°-122° without further phosgene addition. The formation of the desired product was monitored by periodically removing a small sample of the solution and checking for the appearance of an absorption peak by infrared at 2230 $cm^{-1}$, consistent for $SO_2NCO$ and the disappearance of the NH peak at 3350 $cm^{-1}$. The reaction mixture was concentrated in vacuo to remove the xylene solvent and butyl isocyanate by-product and the desired product was isolated as a residue. This residue was dissolved in anhydrous methylene chloride to a total volume of 60 ml and used without further purification.

EXAMPLE 7

N-[(4,6-Dimethylpyrimidin-2-yl)aminocarbonyl]-5,6,7,8-tetrahydronaphthalene-1-sulfonamide To 1.02 g of 2-amino-4,6-dimethylpyrimidine dissolved in 6 ml of anhydrous methylene chloride was added 10 ml of the methylene chloride solution of 5,6,7,8-tetrahydronaphthalene-1-sulfonyl isocyanate prepared in Example 6. The mixture was heated to reflux for 16 hours. After evaporation of the solvent in vacuo, the product was isolated by trituration with 1-chlorobutane and filtration. It melted at 152°-155° and showed absorption peaks in the infrared region at 1690 $cm^{-1}$ (CO) and by proton magnetic resonance at 7.2-7.6 ppm (aromatic CH), 6.3 (pyrimidine CH), 2.2 ppm ($CH_3$) consistent for the desired structure.

EXAMPLE 8

N-[(4,6-Dimethoxy-1,3,5-triazin-2-yl)aminocarbonyl]-5,6,7,8-tetrahydronaphthalene-1-sulfonamide To a stirred suspension, 1.29 g of 2-amino-4,6-dimethoxy-1,3,5-triazine in 6 ml of methylene chloride was added 10 ml of the methylene chloride solution of 5,6,7,8-tetrahydronaphthalene-1-sulfonyl isocyanate prepared in Example 6. After the mixture was refluxed for sixteen hours, the solvent was removed by evaporation in vacuo and the residue triturated with 1-chlorobutane. The mixture was filtered and the filtrate partially evaporated to yield additional solid which melted at 171°-173°. This product showed absorption peaks in the infrared region at 1710 $cm^{-1}$ (CO) and 3300 $cm^{-1}$ (NH) and by proton magnetic resonance at 7.2-7.6 ppm (aromatic CH), 4.1 ppm ($OCH_3$) and 1.0-3.2 ppm ($CH_2$) consistent for the desired structure.

EXAMPLE 9

3-Chloro-1H-indene-4-sulfonyl chloride

To 8.64 g of 2,3-dihydro-1H-indene-4-sulfonyl chloride in 100 ml of carbon tetrachloride was added, with stirring, 75 ml of a 1.06 molar solution of chlorine oxide in carbon tetrachloride dropwise at such a rate that the temperature of the reaction mixture was allowed to rise to 40°. After the addition was completed, the mixture was stirred for 16 hours, then sparged with nitrogen for 10 minutes and the solvent evaporated in vacuo. The residue thus obtained was used in the following example without further purification.

EXAMPLE 10

3-Chloro-1H-indene-4-sulfonamide

1-Chloro-3H-indene-4-sulfonyl chloride (7.0 g) in 50 ml of anhydrous tetrahydrofuran was cooled to −40° and 1.25 ml of liquified ammonia was added so that the reaction mixture temperature remained below −35°. After stirring for one half hour following the addition, the mixture was filtered, the filtered solids washed with tetrahydrofuran and the filtrate concentrated to yield an oil. The oil was purified by column chromatography on silica gel (200–400 mesh) and eluting with 150 ml hexane followed by 300 ml of 30% ethyl acetate in hexane. On standing, this oil solidified. It showed absorption peaks at 3250 and 3350 $cm^{-1}$ for $NH_2$ and 1380 and 1160 consistent for $SO_2$ and melted at 100°–101°.

EXAMPLE 11

3-Chloro-1H-indene-4-sulfonyl isocyanate

An anhydrous mixture of 6.0 g of 1-chloro-3H-indene-4-sulfonamide, 2.6 g of butyl isocyanate and 50 ml of mixed xylenes was heated to reflux at 135°. After 30 minutes, phosgene was passed into the solution under a dry ice cooled reflux condenser until the reflux temperature dropped to 120° whereupon the phosgene addition was discontinued. Heating was continued until the temperature rose to 130° and phosgene addition was resumed. This cycling addition of phosgene was continued until the reflux temperature remained at 120° for at least 30 minutes indicating the presence of an excess of phosgene in the system and completion of the reaction. The reaction mixture was cooled, filtered and evaporated in vacuo to remove xylene and butyl isocyanate. Infrared absorption analysis of the residue showed a peak at 2220 $cm^{-1}$, consistent for the desired structure. The product was diluted to 25 ml in methylene chloride.

EXAMPLE 12

3-Chloro-N-[(4-methoxy-6-methylpyrimidin-2-yl)aminocarbonyl]-1H-indene-4-sulfonamide To 0.69 g of 2-amino-4-methoxy-6-methylpyrimidine in 5 ml of dry methylene chloride was added with stirring 5 ml of 1-chloro-3H-indene-4-sulfonyl isocyanate in methylene chloride from the preceding example. The mixture was heated to reflux for 16 hours and the solvent was evaporated in vacuo. Elutriation of the residue with 1-chlorobutane yielded the solid product which was removed by filtration; it melted at 168°–172°. Infrared absorption peaks at 1700 $cm^{-1}$ (C═O), 1350 $cm^{-1}$ and 1160 $cm^{-1}$ ($SO_2$) and proton magnetic resonance absorption peaks at 2.1 ppm ($CH_3$), 3.6 ppm ($CH_2$), 3.9 ppm ($OCH_3$), 6.2 ppm (pyrimidine CH) and 7.2–8.5 (aromatic CH) confirmed the structure of the product.

EXAMPLE 13

3-Chloro-N-[(4-methoxy-6-methyl-1,3,5-triazin-2-yl)aminocarbonyl]-1H-indene-4-sulfonamide To 0.70 g of 2-amino-4-methoxy-6-methyl-1,3,5-triazine in 5 ml of anhydrous methylene chloride with stirring was added 5 ml of methylene chloride solution of 1-chloro-3H-indene-4-sulfonyl isocyanate prepared above. The mixture was stirred and heated to reflux for 16 hours after which the solvent was removed by evaporation in vacuo. Trituration of the product with 1-chlorobutane dissolved the desired product, but did not dissolve unreacted amino triazine, which was removed by filtration. Addition of hexane to the filtrate caused the desired product to precipitate as a solid which was filtered off, m.p. 168°–170°. It showed absorption peaks in the infrared region at 1710 $cm^{-1}$ (C═O), 1360 and 1160 $cm^{-1}$ ($SO_2$), 3400 $cm^{-1}$ (NH) and by proton magnetic resonance at 2.5 ppm ($CH_3$), 3.5 ppm ($CH_2$), 3.9 ppm ($OCH_3$), and 7.4–8.5 ppm (aromatic CH) consistent for the desired structure.

Using the procedures of the previous Examples, 1–13, the following compounds of Tables I–III can be prepared.

TABLE Ia

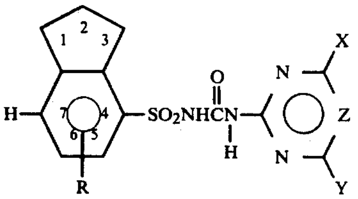

| R | X | Y | Z | m.p.(°C.) |
|---|---|---|---|---|
| H | $CH_3$ | $CH_3$ | CH | 107–110° |
| H | $OCH_3$ | $CH_3$ | CH | 186–188° |
| H | $OCH_3$ | $OCH_3$ | CH | 165–167° |
| H | $CH_3$ | $C_2H_5$ | CH | |
| H | $OCH_3$ | $C_2H_5$ | CH | |
| H | $CH_3$ | $OC_2H_5$ | CH | |
| H | $OCH_3$ | $OC_2H_5$ | CH | |
| H | $CH_3$ | $CH_2OCH_3$ | CH | |
| H | $OCH_3$ | $CH_2OCH_3$ | CH | |
| H | $OCH_3$ | $NH_2$ | CH | |
| H | $OCH_3$ | $NHCH_3$ | CH | |
| H | $OCH_3$ | $N(CH_3)_2$ | CH | |
| H | $CH_3$ | $CH_3$ | N | 167–169° |
| H | $OCH_3$ | $CH_3$ | N | 205–207° |
| H | $OCH_3$ | $OCH_3$ | N | 164–166° |
| H | $CH_3$ | $C_2H_5$ | N | |
| H | $OCH_3$ | $C_2H_5$ | N | |
| H | $CH_3$ | $OC_2H_5$ | N | |
| H | $OCH_3$ | $OC_2H_5$ | N | |
| H | $CH_3$ | $CH_2OCH_3$ | N | |
| H | $OCH_3$ | $CH_2OCH_3$ | N | |
| H | $OCH_3$ | $NH_2$ | N | |
| H | $OCH_3$ | $NHCH_3$ | N | |
| H | $OCH_3$ | $N(CH_3)_2$ | N | |
| H | $CH_3$ | $CH(OCH_3)_2$ | CH | |
| H | $OCH_3$ | $CH(OCH_3)_2$ | CH | |
| H | $CH_3$ | 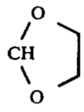 | CH | |
| H | $OCH_3$ | 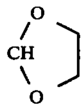 | CH | |
| H | $CH_3$ | $CH(OCH_3)_2$ | N | |
| H | $OCH_3$ | $CH(OCH_3)_2$ | N | |
| H | $CH_3$ | 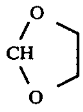 | | N |
| H | $OCH_3$ | 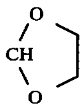 | N | |
| H | Cl | $OCH_3$ | CH | |
| H | Cl | $NH_2$ | CH | |
| H | Cl | $NHCH_3$ | CH | |
| H | Cl | $N(CH_3)_2$ | CH | |
| H | $CH_3$ | $SCH_3$ | N | |
| H | $OCH_3$ | $SCH_3$ | N | |
| H | $CH_3$ | $SCH_3$ | CH | |
| H | $OCH_3$ | $SCH_3$ | CH | |
| 5-Cl | $CH_3$ | $CH_3$ | CH | |

TABLE Ia-continued

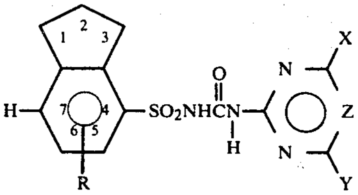

| R | X | Y | Z | m.p.(°C.) |
|---|---|---|---|---|
| 5-Cl | OCH3 | CH3 | CH | |
| 5-Cl | OCH3 | OCH3 | CH | |
| 5-Cl | CH3 | C2H5 | CH | |
| 5-Cl | OCH3 | C2H5 | CH | |
| 5-Cl | CH3 | OC2H5 | CH | |
| 5-Cl | OCH3 | OC2H5 | CH | |
| 5-Cl | CH3 | CH2OCH3 | CH | |
| 5-Cl | OCH3 | CH2OCH3 | CH | |
| 5-Cl | OCH3 | NH2 | CH | |
| 5-Cl | OCH3 | NHCH3 | CH | |
| 5-Cl | OCH3 | N(CH3)2 | CH | |
| 5-Cl | CH3 | CH3 | N | |
| 5-Cl | OCH3 | CH3 | N | |
| 5-Cl | OCH3 | OCH3 | N | |
| 5-Cl | CH3 | C2H5 | N | |
| 5-Cl | OCH3 | C2H5 | N | |
| 5-Cl | CH3 | OC2H5 | N | |
| 5-Cl | OCH3 | OC2H5 | N | |
| 5-Cl | CH3 | CH2OCH3 | N | |
| 5-Cl | OCH3 | CH2OCH3 | N | |
| 5-Cl | OCH3 | NH2 | N | |
| 5-Cl | OCH3 | NHCH3 | N | |
| 5-Cl | OCH3 | N(CH3)2 | N | |
| 5-Cl | CH3 | CH(OCH3)2 | CH | |
| 5-Cl | CH3 | CH(OCH3)2 | N | |
| 5-Cl | OCH3 | CH(OCH3)2 | CH | |
| 5-Cl | OCH3 | CH(OCH3)2 | N | |
| 5-Cl | CH3 | 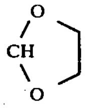 | CH | |
| 5-Cl | OCH3 | 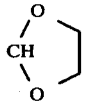 | CH | |
| 5-Cl | Cl | OCH3 | CH | |
| 5-Cl | Cl | NH2 | CH | |
| 5-Cl | Cl | N(CH3)2 | CH | |
| 6-Cl | CH3 | CH3 | CH | |
| 6-Cl | OCH3 | CH3 | CH | |
| 6-Cl | OCH3 | OCH3 | CH | |
| 6-Cl | CH3 | C2H5 | CH | |
| 6-Cl | OCH3 | C2H5 | CH | |
| 6-Cl | CH3 | OC2H5 | CH | |
| 6-Cl | OCH3 | OC2H5 | CH | |
| 6-Cl | CH3 | CH2OCH3 | CH | |
| 6-Cl | OCH3 | CH2OCH3 | CH | |
| 6-Cl | OCH3 | NH2 | CH | |
| 6-Cl | OCH3 | NHCH3 | CH | |
| 6-Cl | OCH3 | N(CH3)2 | CH | |
| 6-Cl | CH3 | NHCH3 | CH | |
| 6-Cl | CH3 | NH2 | CH | |
| 6-Cl | CH3 | N(CH3)2 | CH | |
| 6-Cl | CH3 | CH3 | N | |
| 6-Cl | OCH3 | CH3 | N | |
| 6-Cl | OCH3 | OCH3 | N | |
| 6-Cl | CH3 | C2H5 | N | |
| 6-Cl | OCH3 | C2H5 | N | |
| 6-Cl | CH3 | OC2H5 | N | |
| 6-Cl | OCH3 | OC2H5 | N | |
| 6-Cl | CH3 | CH2OCH3 | N | |
| 6-Cl | OCH3 | CH2OCH3 | N | |
| 6-Cl | OCH3 | NH2 | N | |
| 6-Cl | OCH3 | NHCH3 | N | |
| 6-Cl | OCH3 | N(CH3)2 | N | |

TABLE Ia-continued

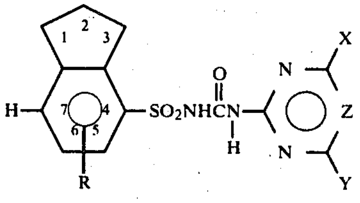

| R | X | Y | Z | m.p.(°C.) |
|---|---|---|---|---|
| 5-NO2 | CH3 | 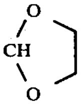 | CH | |
| 5-NO2 | OCH3 | 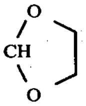 | CH | |
| 5-NO2 | CH3 | 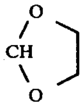 | N | |
| 5-NO2 | OCH3 | 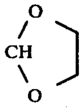 | N | |
| 5-NO2 | Cl | OCH3 | CH | |
| 5-NO2 | CH3 | CH3 | CH | 172 dec. |
| 5-NO2 | OCH3 | CH3 | CH | 65 dec. |
| 5-NO2 | OCH3 | OCH3 | CH | 162 dec. |
| 5-NO2 | CH3 | C2H5 | CH | |
| 5-NO2 | OCH3 | C2H5 | CH | |
| 5-NO2 | CH3 | OC2H5 | CH | |
| 5-NO2 | OCH3 | OC2H5 | CH | |
| 5-NO2 | CH3 | CH2OCH3 | CH | |
| 5-NO2 | OCH3 | CH2OCH3 | CH | |
| 5-NO2 | OCH3 | NH2 | CH | |
| 5-NO2 | OCH3 | NHCH3 | CH | |
| 5-NO2 | OCH3 | N(CH3)2 | CH | |
| 5-NO2 | CH3 | CH3 | N | |
| 5-NO2 | OCH3 | CH3 | N | 163 dec. |
| 5-NO2 | OCH3 | OCH3 | N | 170-175° |
| 5-NO2 | CH3 | C2H5 | N | |
| 5-NO2 | OCH3 | C2H5 | N | |
| 5-NO2 | CH3 | OC2H5 | N | |
| 5-NO2 | OCH3 | OC2H5 | N | |
| 5-NO2 | CH3 | CH2OCH3 | N | |
| 5-NO2 | OCH3 | CH2OCH3 | N | |
| 5-NO2 | OCH3 | NH2 | N | |
| 5-NO2 | OCH3 | NHCH3 | N | |
| 5-NO2 | OCH3 | N(CH3)2 | N | |
| 6-NO2 | CH3 | CH3 | CH | 170-178° |
| 6-NO2 | OCH3 | CH3 | CH | 85 dec. |
| 6-NO2 | OCH3 | OCH3 | CH | 200-206° |
| 6-NO2 | CH3 | C2H5 | CH | |
| 6-NO2 | OCH3 | C2H5 | CH | |
| 6-NO2 | CH3 | OC2H5 | CH | |
| 6-NO2 | OCH3 | CH | | |
| 6-NO2 | CH3 | CH2OCH3 | CH | |
| 6-NO2 | OCH3 | CH2OCH3 | CH | |
| 6-NO2 | OCH3 | NH2 | CH | |
| 6-NO2 | OCH3 | NHCH3 | CH | |
| 6-NO2 | OCH3 | N(CH3)2 | CH | |
| 6-NO2 | CH3 | NHCH3 | CH | |
| 6-NO2 | CH3 | NH2 | CH | |
| 6-NO2 | CH3 | N(CH3)2 | CH | |
| 6-NO2 | CH3 | CH3 | N | 140-143° |
| 6-NO2 | OCH3 | CH3 | N | |
| 6-NO2 | OCH3 | OCH3 | N | 170-172° |
| 6-NO2 | CH3 | C2H5 | N | |

TABLE Ia-continued

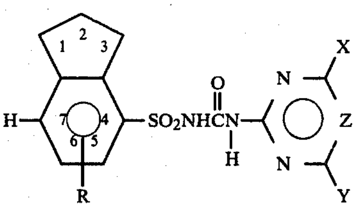

| R | X | Y | Z | m.p.(°C.) |
|---|---|---|---|---|
| 6-$NO_2$ | $OCH_3$ | $C_2H_5$ | N | |
| 6-$NO_2$ | $CH_3$ | $OC_2H_5$ | N | |
| 6-$NO_2$ | $OCH_3$ | $OC_2H_5$ | N | |
| 6-$NO_2$ | $CH_3$ | $CH_2OCH_3$ | N | |
| 6-$NO_2$ | $OCH_3$ | $CH_2OCH_3$ | N | |
| 6-$NO_2$ | $OCH_3$ | $NH_2$ | N | |
| 6-$NO_2$ | $OCH_3$ | $NHCH_3$ | N | |
| 6-$NO_2$ | $OCH_3$ | $N(CH_3)_2$ | N | |
| 6-$NO_2$ | $CH_3$ | $NHCH_3$ | N | |
| 6-$NO_2$ | $CH_3$ | $NH_2$ | N | |
| 6-$NO_2$ | $CH_3$ | $N(CH_3)_2$ | N | |
| 6-Br | $CH_3$ | $CH_3$ | CH | |
| 6-Br | $CH_3$ | $OCH_3$ | CH | |
| 6-Br | $OCH_3$ | $OCH_3$ | CH | |
| 6-$OCH_3$ | $CH_3$ | $CH_3$ | CH | |
| 6-$OCH_3$ | $OCH_3$ | $CH_3$ | CH | |
| 6-$OCH_3$ | $OCH_3$ | $OCH_3$ | CH | |
| 6-Br | $CH_3$ | $CH_3$ | N | |
| 6-Br | $CH_3$ | $OCH_3$ | N | |
| 6-Br | $OCH_3$ | $OCH_3$ | N | |
| 6-$OCH_3$ | $CH_3$ | $CH_3$ | N | |
| 6-$OCH_3$ | $OCH_3$ | $CH_3$ | N | |
| 6-$OCH_3$ | $OCH_3$ | $OCH_3$ | N | |
| 5-Br | $CH_3$ | $CH_3$ | CH | |
| 5-Br | $CH_3$ | $OCH_3$ | CH | |
| 5-Br | $OCH_3$ | $OCH_3$ | CH | |
| 5-$OCH_3$ | $CH_3$ | $CH_3$ | CH | |
| 5-$OCH_3$ | $OCH_3$ | $CH_3$ | CH | |
| 5-$OCH_3$ | $OCH_3$ | $OCH_3$ | CH | |
| 5-$OC_2H_5$ | $CH_3$ | $CH_3$ | CH | |
| 5-$OC_2H_5$ | $CH_3$ | $OCH_3$ | CH | |
| 5-$OC_2H_5$ | $OCH_3$ | $OCH_3$ | CH | |
| 5-$OCH(CH_3)_2$ | $CH_3$ | $CH_3$ | CH | |
| 5-$OCH(CH_3)_2$ | $OCH_3$ | $CH_3$ | CH | |
| 5-$OCH(CH_3)_2$ | $OCH_3$ | $OCH_3$ | CH | |
| 5-$OCH_2CH_2CH_3$ | $CH_3$ | $CH_3$ | CH | |
| 5-$OCH_2CH_2CH_3$ | $OCH_3$ | $CH_3$ | CH | |
| 5-$OCH_2CH_2CH_3$ | $OCH_3$ | $OCH_3$ | CH | |
| 5-Br | $CH_3$ | $CH_3$ | N | |
| 5-Br | $CH_3$ | $OCH_3$ | N | |
| 5-Br | $OCH_3$ | $OCH_3$ | N | |
| 5-$OCH_3$ | $CH_3$ | $CH_3$ | N | |
| 5-$OCH_3$ | $OCH_3$ | $CH_3$ | N | |
| 5-$OCH_3$ | $OCH_3$ | $OCH_3$ | N | |
| 5-$OC_2H_5$ | $CH_3$ | $CH_3$ | N | |
| 5-$OC_2H_5$ | $CH_3$ | $OCH_3$ | N | |
| 5-$OC_2H_5$ | $OCH_3$ | $OCH_3$ | N | |
| 5-$OCH(CH_3)_2$ | $CH_3$ | $CH_3$ | N | |
| 5-Br | $CH_3$ | $CH(OCH_3)_2$ | CH | |
| 5-Br | Cl | $OCH_3$ | CH | |
| 5-$OCH_3$ | $OCH_3$ | $CH(OCH_3)_2$ | CH | |
| 5-$OCH_3$ | $CH_3$ | $CH(OCH_3)_2$ | N | |
| 5-$OCH_3$ | Cl | $OCh_3$ | CH | |
| 5-$OC_2H_5$ | Cl | $OCh_3$ | CH | |
| 5-$OCH(CH_3)_2$ | Cl | $OCH_3$ | CH | |
| 5-$OCH(CH_3)_2$ | $CH_3$ | $CH(OCH_3)_2$ | CH | |
| 5-$OCH(CH_3)_2$ | $OCH_3$ | $CH_3$ | N | |
| 5-$OCH(CH_3)_2$ | $OCH_3$ | $OCH_3$ | N | |
| 5-$OCH_2CH_2CH_3$ | $CH_3$ | $CH_3$ | N | |
| 5-$OCH_2CH_2CH_3$ | $OCH_3$ | $CH_3$ | N | |
| 5-$OCH_2CH_2CH_3$ | $OCH_3$ | $OCH_3$ | N | |
| 5-$SO_2N(CH_3)_2$ | $CH_3$ | $CH_3$ | CH | |
| 5-$SO_2N(CH_3)_2$ | $CH_3$ | $OCH_3$ | CH | |
| 5-$SO_2N(CH_3)_2$ | $OCH_3$ | $OCH_3$ | CH | |
| 5-$SO_2N(C_2H_5)_2$ | $CH_3$ | $CH_3$ | CH | |
| 5-$SO_2N(C_2H_5)_2$ | $CH_3$ | $OCH_3$ | CH | |
| 5-$SO_2N(C_2H_5)_2$ | $OCH_3$ | $OCH_3$ | CH | |
| 5-$SO_2N(CH_3)C_2H_5$ | $CH_3$ | $CH_3$ | CH | |
| 5-$SO_2N(CH_3)C_2H_5$ | $CH_3$ | $OCH_3$ | CH | |
| 5-$SO_2N(CH_3)C_2H_5$ | $OCH_3$ | $OCH_3$ | CH | |

TABLE Ia-continued

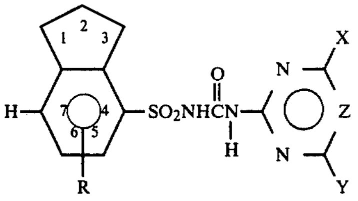

| R | X | Y | Z | m.p.(°C.) |
|---|---|---|---|---|
| 5-$SO_2N(CH_3)OCH_3$ | $CH_3$ | $CH_3$ | CH | |
| 5-$SO_2N(CH_3)OCH_3$ | $CH_3$ | $OCH_3$ | CH | |
| 5-$SO_2N(CH_3)OCH_3$ | $OCH_3$ | $OCH_3$ | CH | |
| 5-$OSO_2CF_3$ | $CH_3$ | $CH_3$ | CH | |
| 5-$OSO_2CF_3$ | $CH_3$ | $OCH_3$ | CH | |
| 5-$OSO_2CF_3$ | $OCH_3$ | $OCH_3$ | CH | |
| 5-$OSO_2CH_3$ | $CH_3$ | $CH_3$ | CH | |
| 5-$OSO_2CH_3$ | $CH_3$ | $OCH_3$ | CH | |
| 5-$OSO_2CH_3$ | $OCH_3$ | $OCH_3$ | CH | |
| 5-$OSO_2C_2H_5$ | $CH_3$<br>$CH_3$ | CH | | |
| 5-$OSO_2C_2H_5$ | $CH_3$ | $OCH_3$ | CH | |
| 5-$OSO_2C_2H_5$ | $OCH_3$ | $OCh_3$ | CH | |
| 5-$OSO_2$—n-$C_3H_7$ | $CH_3$ | $CH_3$ | CH | |
| 5-$OSO_2$—n-$C_3H_7$ | $CH_3$ | $OCH_3$ | CH | |
| 5-$OSO_2$—n-$C_3H_7$ | $OCH_3$ | $OCH_3$ | CH | |
| 5-$CO_2CH_3$ | $CH_3$ | $CH_3$ | CH | |
| 5-$CO_2CH_3$ | $CH_3$ | $OCH_3$ | CH | |
| 5-$CO_2CH_3$ | $OCH_3$ | $OCH_3$ | CH | |
| 5-$SO_2NN(CH_3)_2$ | Cl | $OCH_3$ | CH | |
| 5-$SO_2N(CH_3)_2$ | $CH_3$ | $CH(OCH_3)_2$ | CH | |
| 5-$SO_2N(CH_3)_2$ | $CH_3$ | $CH(OCH_3)_2$ | N | |
| 5-$SO_2N(CH_3)_2$ | $CH_3$ | 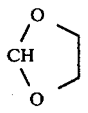 | N | |
| 5-$SO_2N(CH_3)_2$ | $CH_3$ | 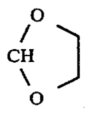 | CH | |
| 5-$SO_2N(C_2H_5)_2$ | 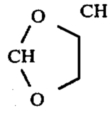 | CH | | |
| 5-$SO_2N(C_2H_5)_2$ | $OCH_3$ | $CH(OCH_3)_2$ | CH | |
| 5-$SO_2N(C_2H_5)_2$ | Cl | $OCH_3$ | CH | |
| 5-$SO_2N(OCH_3)CH_3$ | Cl | $OCH_3$ | CH | |
| 5-$SO_2N(OCH_3)CH_3$ | $CH_3$ | $CH(OCH_3)_2$ | CH | |
| 5-$SO_2N(OCH_3)CH_3$ | $OCH_3$ | $CH(OCH_3)_2$ | CH | |
| 5-$OSO_2CH_3$ | Cl | $OCH_3$ | CH | |
| 5-$OSO_2CH_3$ | $CH_3$ | $CH(OCH_3)_2$ | CH | |
| 5-$OSO_2CH_3$ | $OCH_3$ | $CH(OCH_3)_2$ | CH | |
| 5-$OSO_2CF_3$ | Cl | $OCH_3$ | CH | |
| 5-$OSO_2CF_3$ | $OCH_3$ | $CH(OCH_3)_2$ | CH | |
| 5-$OSO_2$—$CH_2CH_2CH_3$ | $OCH_3$ | $CH(OCH_3)_2$ | CH | |
| 5-$OSO_2$—$CH_2CH_2CH_3$ | Cl | $OCH_3$ | CH | |
| 5-$CO_2CH_3$ | $CH_3$ | $OCH_3$ | N | |
| 5-$CO_2CH_3$ | $OCH_3$ | $OCH_3$ | N | |
| 5-$CO_2CH_3$ | Cl | $OCH_3$ | CH | |
| 5-$CO_2CH_3$ | $CH_3$ | $CH(OCH_3)_2$ | CH | |
| 5-$CO_2CH_3$ | $OCH_3$ | $CH(OCH_3)_2$ | CH | |
| 5-$CO_2C_2H_5$ | Cl | $OCH_3$ | CH | |
| 5-$CO_2C_2H_5$ | $CH_3$ | $CH(OCH_3)_2$ | CH | |
| 5-$CO_2C_2H_5$ | $OCH_3$ | $CH(OCH_3)_2$ | N | |
| 5-$CO_2C_2H_5$ | $OCH_3$ | 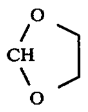 | N | |

TABLE Ia-continued

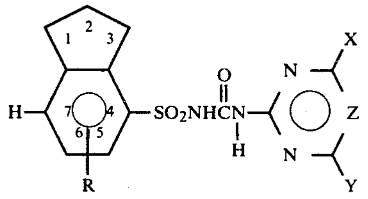

| R | X | Y | Z | m.p.(°C.) |
|---|---|---|---|---|
| 5-$CO_2C_2H_5$ | $OCH_3$ | 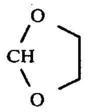 | CH | |
| 5-$CO_2CH_2CH_2OCH_3$ | Cl | $OCH_3$ | CH | |
| 5-$CO_2CH(CH_3)_2$ | Cl | $OCH_3$ | CH | |
| 5-$CO_2CH(CH_3)_2$ | $OCH_3$ | $CH_3$ | CH | |
| 5-$CO_2CH(CH_3)_2$ | $CH_3$ | 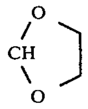 | CH | |
| 5-$CO_2C_2H_5$ | $CH_3$ | $CH_3$ | CH | |
| 5-$CO_2C_2H_5$ | $CH_3$ | $OCH_3$ | CH | |
| 5-$CO_2C_2H_2$ | $OCH_3$ | $OCH_3$ | CH | |
| 5-$CO_2$—n-$C_3H_7$ | $CH_3$ | $CH_3$ | CH | |
| 5-$CO_2$—n-$C_3H_7$ | $CH_3$ | $OCH_3$ | CH | |
| 5-$CO_2$—n-$C_3H_7$ | $OCH_3$ | $OCH_3$ | CH | |
| 5-$CO_2$—i-$C_3H_7$ | $CH_3$ | $CH_3$ | CH | |
| 5-$CO_2$—i-$C_3H_7$ | $CH_3$ | $OCH_3$ | CH | |
| 5-$CO_2$—i-$C_3H_7$ | $OCH_3$ | $OCH_3$ | CH | |
| 5-$CO_2CH_2$—CH=$CH_2$ | $CH_3$ | $CH_3$ | CH | |
| 5-$CO_2CH_2CH$=$CH_2$ | $CH_3$ | $OCH_3$ | CH | |
| 5-$CO_2CH_2CH$=$CH_2$ | $OCH_3$ | $OCH_3$ | CH | |
| 5-$CO_2CH_2CH_2OCH_3$ | $CH_3$ | $CH_3$ | CH | |
| 5-$CO_2CH_2CH_2OCH_3$ | $CH_3$ | $OCH_3$ | CH | |
| 5-$CO_2CH_2CH_2OCH_3$ | $OCH_3$ | $OCH_3$ | CH | |
| 5-$CO_2CH_2CH_2Cl$ | $CH_3$ | $CH_3$ | CH | |
| 5-$CO_2CH_2CH_2Cl$ | $CH_3$ | $OCH_3$ | CH | |
| 5-$CO_2CH_2CH_2Cl$ | $OCH_3$ | $OCH_3$ | CH | |
| 5-$SO_2CH_3$ | $CH_3$ | $CH_3$ | CH | |
| 5-$SO_2CH_3$ | $CH_3$ | $OCH_3$ | CH | |
| 5-$SO_2CH_3$ | $OCH_3$ | $OCH_3$ | CH | |
| 5-$SO_2N(CH_3)_2$ | $CH_3$ | $CH_3$ | N | |
| 5-$SO_2N(CH_3)_2$ | $CH_3$ | $OCH_3$ | N | |
| 5-$SO_2N(CH_3)_2$ | $OCH_3$ | $OCH_3$ | N | |
| 5-$SO_2N(C_2H_5)_2$ | $CH_3$ | $CH_3$ | N | |
| 5-$SO_2N(C_2H_5)_2$ | $CH_3$ | $OCH_3$ | N | |
| 5-$SO_2N(C_2H_5)_2$ | $OCH_3$ | $OCH_3$ | N | |
| 5-$SO_2N(CH_3)C_2H_5$ | $CH_3$ | $CH_3$ | N | |
| 5-$SO_2N(CH_3)C_2H_5$ | $CH_3$ | $OCH_3$ | N | |
| 5-$SO_2N(CH_3)C_2H_5$ | $OCH_3$ | $OCH_3$ | N | |
| 5-$SO_2N(CH_3)OCH_3$ | $CH_3$ | $CH_3$ | N | |
| 5-$SO_2N(CH_3)OCH_3$ | $CH_3$ | $OCH_3$ | N | |
| 5-$SO_2N(CH_3)OCH_3$ | $OCH_3$ | $OCH_3$ | N | |
| 5-$OSO_2CF_3$ | $CH_3$ | $CH_3$ | N | |
| 5-$OSO_2CF_3$ | $CH_3$ | $OCH_3$ | N | |
| 5-$OSO_2CF_3$ | $OCH_3$ | $OCH_3$ | N | |
| 5-$OSO_2CF_3$ | $CH_3$ | $CH_3$ | N | |
| 5-$OSO_2CF_3$ | $CH_3$ | $OCH_3$ | N | |
| 5-$OSO_2CF_3$ | $OCH_3$ | $OCH_3$ | N | |
| 5-$OSO_2C_2H_5$ | $CH_3$ | $CH_3$ | N | |
| 5-$OSO_2C_2H_5$ | $CH_3$ | $OCH_3$ | N | |
| 5-$OSO_2C_2H_5$ | $OCH_3$ | $OCH_3$ | N | |
| 5-$OSO_2$—n-$C_3H_7$ | $CH_3$ | $CH_3$ | N | |
| 5-$OSO_2$—n-$C_3H_7$ | $CH_3$ | $OCH_3$ | N | |
| 5-$OSO_2$—n-$C_3H_7$ | $OCH_3$ | $OCH_3$ | N | |
| 5-$CO_2CH_3$ | $CH_3$ | $CH_3$ | N | |
| 5-$CO_2CH_3$ | $CH_3$ | $OCH_3$ | N | |
| 5-$CO_2CH_3$ | $OCH_3$ | $OCH_3$ | N | |
| 5-$CO_2C_2H_5$ | $CH_3$ | $CH_3$ | N | |
| 5-$CO_2C_2H_5$ | $CH_3$ | $OCH_3$ | N | |
| 5-$CO_2C_2H_5$ | $OCH_3$ | $OCH_3$ | N | |
| 5-$CO_2$—n-$C_3H_7$ | $CH_3$ | $CH_3$ | N | |
| 5-$CO_2$—n-$C_3H_7$ | $CH_3$ | $OCH_3$ | N | |
| 5-$CO_2$—n-$C_3H_7$ | $OCH_3$ | $OCH_3$ | N | |

TABLE Ia-continued

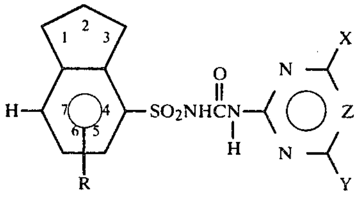

| R | X | Y | Z | m.p.(°C.) |
|---|---|---|---|---|
| 5-$CO_2$—i-$C_3H_7$ | $CH_3$ | $CH_3$ | N | |
| 5-$CO_2$—i-$C_3H_7$ | $CH_3$ | $OCH_3$ | N | |
| 5-$CO_2$—i-$C_3H_7$ | $OCH_3$ | $OCH_3$ | N | |
| 5-$CO_2CH_2CH$=$CH_2$ | $CH_3$ | $CH_3$ | N | |
| 5-$CO_2CH_2CH$=$CH_2$ | $CH_3$ | $OCH_3$ | N | |
| 5-$CO_2CH_2CH$=$CH_2$ | $OCH_3$ | $OCH_3$ | N | |
| 5-$CO_2CH_2CH_2OCH_3$ | $CH_3$ | $CH_3$ | N | |
| 5-$CO_2CH_2CH_2OCH_3$ | $CH_3$ | $OCH_3$ | N | |
| 5-$CO_2CH_2CH_2OCH_3$ | $OCH_3$ | $OCH_3$ | N | |
| 5-$CO_2CH_2CH_2Cl$ | $CH_3$ | $CH_3$ | N | |
| 5-$CO_2CH_2CH_2Cl$ | $CH_3$ | $OCH_3$ | N | |
| 5-$CO_2CH_2CH_2Cl$ | $OCH_3$ | $OCH_3$ | N | |
| 5-$SO_2CH_3$ | $CH_3$ | N | | |
| 5-$SO_2CH_3$ | $CH_3$ | $OCH_3$ | N | |
| 5-$SO_2CH_3$ | $OCH_3$ | $OCH_3$ | N | |
| 5-$SCH_3$ | $CH_3$ | $CH_3$ | N | |
| 5-$SCH_3$ | $OCH_3$ | $OCH_3$ | N | |
| 5-$SCH_3$ | $OCH_3$ | $CH_3$ | N | |
| 5-$SCH_3$ | $CH_3$ | $CH_3$ | CH | |
| 5-$SCH_3$ | $OCH_3$ | $OCH_3$ | CH | |
| 5-$SCH_3$ | $OCH_3$ | $CH_3$ | CH | |
| 5-$C_2H_5$ | $CH_3$ | $OCH_3$ | CH | |
| 5-$C_2H_5$ | $OCH_3$ | $OCH_3$ | CH | |
| 5-$C_2H_5$ | $CH_3$ | $OCH_3$ | N | |
| 5-$C_2H_5$ | $OCH_3$ | $OCH_3$ | N | |
| 5-$CH(CH_3)_2$ | $OCH_3$ | $CH_3$ | CH | |
| 5-$CH(CH_3)_2$ | $OCH_3$ | $OCH_3$ | CH | |
| 5-$CH(CH_3)_2$ | $CH_3$ | $OCH_3$ | N | |
| 5-$CH(CH_3)_2$ | $OCH_3$ | $OCH_3$ | N | |
| 5-n-$C_3H_7$ | $OCH_3$ | $OCH_3$ | N | |
| 5-n-$C_3H_7$ | $CH_3$ | $OCH_3$ | N | |
| 5-n-$C_3H_7$ | $CH_3$ | $CH_2OCH_3$ | N | |
| 5-$SCF_2H$ | $CH_3$ | $OCH_3$ | N | |
| 5-$SCF_2H$ | $OCH_3$ | $OCH_3$ | N | |
| 5-$SCF_2H$ | Cl | $OCH_3$ | CH | |
| 5-$OCF_3$ | $OCH_3$ | $OCH_3$ | CH | |
| 5-$OCF_3$ | $CH_3$ | $OCH_3$ | CH | |
| 5-$OCF_2H$ | $OCH_3$ | $CH_3$ | N | |
| 5-$OCF_2H$ | $OCH_3$ | $OCH_3$ | CH | |
| $OCF_2HCF_2H$ | $CH_3$ | $CH_3$ | CH | |
| $OCF_2HCF_2H$ | Cl | $OCH_3$ | CH | |
| $OCF_2HCF_2H$ | $OCH_3$ | $CH_3$ | CH | |
| $OCF_2HCF_2H$ | $OCH_3$ | $OCH_3$ | CH | |
| $OCF_2HCF_2H$ | $CH_3$ | $OCH_3$ | N | |
| $C_2H_5$ | $CH_3$ | $OCH_3$ | N | |
| $C_2H_5$ | $CH_3$ | $CH_3$ | CH | |
| $C_2H_5$ | $OCH_3$ | $CH_3$ | CH | |
| $C_2H_5$ | $OCH_3$ | $OCH_3$ | CH | |
| $C_2H_5$ | Cl | $OCH_3$ | CH | |
| $CH(CH_3)_2$ | $OCH_3$ | $OCH_3$ | CH | |
| $CH(CH_3)_2$ | $CH_3$ | $OCH_3$ | CH | |
| $CH(CH_3)_2$ | $CH_3$ | $CH_3$ | CH | |
| n-$C_3H_7$ | $CH_3$ | $CH_3$ | CH | |
| n-$C_3H_7$ | $OCH_3$ | $CH_3$ | CH | |
| n-$C_3H_7$ | $OCH_3$ | $OCH_3$ | CH | |

TABLE Ib

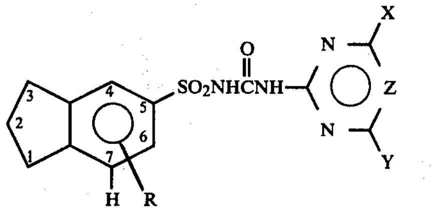

| R | X | Y | Z | m.p. (°C.) |
|---|---|---|---|---|
| H | $CH_3$ | $CH_3$ | CH | 168–170° |
| H | $OCH_3$ | $CH_3$ | CH | 177–178° |
| H | $OCH_3$ | $OCH_3$ | CH | 177–178° |
| H | $CH_3$ | $C_2H_5$ | CH | |
| H | $OCH_3$ | $C_2H_5$ | CH | |
| H | $CH_3$ | $OC_2H_5$ | CH | |
| H | $OCH_3$ | $OC_2H_5$ | CH | |
| H | $CH_3$ | $CH_2OCH_3$ | CH | |
| H | $OCH_3$ | $CH_2OCH_3$ | CH | |
| H | $OCH_3$ | $NH_2$ | CH | |
| H | $OCH_3$ | $NHCH_3$ | CH | |
| H | $OCH_3$ | $N(CH_3)_2$ | CH | |
| H | $CH_3$ | $CH_3$ | N | 167–170° |
| H | $OCH_3$ | $CH_3$ | N | $>150$ dec |
| H | $OCH_3$ | $OCH_3$ | N | 180–182° |
| H | $CH_3$ | $C_2H_5$ | N | |
| H | $OCH_3$ | $C_2H_5$ | N | |
| H | $CH_3$ | $OC_2H_5$ | N | |
| H | $OCH_3$ | $OC_2H_5$ | N | |
| H | $CH_3$ | $CH_2OCH_3$ | N | |
| H | $OCH_3$ | $CH_2OCH_3$ | N | |
| H | $OCH_3$ | $NH_2$ | N | |
| H | $OCH_3$ | $NHCH_3$ | N | |
| H | $OCH_3$ | $N(CH_3)_2$ | N | |
| H | $OCH_3$ | $SCH_3$ | N | |
| H | $CH_3$ | $SCH_3$ | N | |
| H | $OCH_3$ | $SCH_3$ | CH | |
| H | $CH_3$ | $SCH_3$ | CH | |
| 4-Cl | $CH_3$ | $CH_3$ | CH | |
| 4-Cl | $OCH_3$ | $CH_3$ | CH | |
| 4-Cl | $OCH_3$ | $OCH_3$ | CH | |
| 4-Cl | $CH_3$ | $C_2H_5$ | CH | |
| 4-Cl | $OCH_3$ | $C_2H_5$ | CH | |
| 4-Cl | $CH_3$ | $OC_2H_5$ | CH | |
| 4-Cl | $OCH_3$ | $OC_2H_5$ | CH | |
| 4-Cl | $CH_3$ | $CH_2OCH_3$ | CH | |
| 4-Cl | $OCH_3$ | $CH_2OCH_3$ | CH | |
| 4-Cl | $OCH_3$ | $NH_2$ | CH | |
| 4-Cl | $OCH_3$ | $NHCH_3$ | CH | |
| 4-Cl | $OCH_3$ | $N(CH_3)_2$ | CH | |
| 4-Cl | $CH_3$ | $CH_3$ | N | |
| 4-Cl | $OCH_3$ | $CH_3$ | N | |
| 4-Cl | $OCH_3$ | $OCH_3$ | N | |
| 4-Cl | $CH_3$ | $C_2H_5$ | N | |
| 4-Cl | $OCH_3$ | $C_2H_5$ | N | |
| 4-Cl | $CH_3$ | $OC_2H_5$ | N | |
| 4-Cl | $OCH_3$ | $OC_2H_5$ | N | |
| 4-Cl | $CH_3$ | $CH_2OCH_3$ | N | |
| 4-Cl | $OCH_3$ | $CH_2OCH_3$ | N | |
| 4-Cl | $OCH_3$ | $NH_2$ | N | |
| 4-Cl | $OCH_3$ | $NHCH_3$ | N | |
| 4-Cl | $OCH_3$ | $N(CH_3)_2$ | N | |
| 6-Cl | $CH_3$ | $CH_3$ | CH | |
| 6-Cl | $OCH_3$ | $CH_3$ | CH | |
| 6-Cl | $OCH_3$ | $OCH_3$ | CH | |
| 6-Cl | $CH_3$ | $C_2H_5$ | CH | |
| 6-Cl | $OCH_3$ | $C_2H_5$ | CH | |
| 6-Cl | $CH_3$ | $OC_2H_5$ | CH | |
| 6-Cl | $OCH_3$ | $OC_2H_5$ | CH | |
| 6-Cl | $CH_3$ | $CH_2OCH_3$ | CH | |
| 6-Cl | $OCH_3$ | $CH_2OCH_3$ | CH | |
| 6-Cl | $OCH_3$ | $NH_2$ | CH | |
| 6-Cl | $OCH_3$ | $NHCH_3$ | CH | |
| 6-Cl | $OCH_3$ | $N(CH_3)_2$ | CH | |
| 6-Cl | $CH_3$ | $CH_3$ | N | |
| 6-Cl | $OCH_3$ | $CH_3$ | N | |
| 6-Cl | $OCH_3$ | $OCH_3$ | N | |
| 6-Cl | $CH_3$ | $C_2H_5$ | N | |
| 6-Cl | $OCH_3$ | $C_2H_5$ | N | |
| 6-Cl | $CH_3$ | $OC_2H_5$ | N | |

TABLE Ib-continued

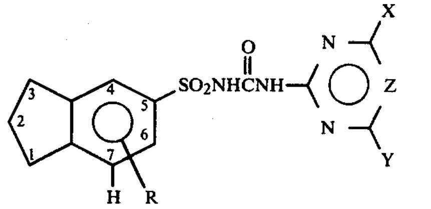

| R | X | Y | Z | m.p. (°C.) |
|---|---|---|---|---|
| 6-Cl | $OCH_3$ | $OC_2H_5$ | N | |
| 6-Cl | $CH_3$ | $CH_2OCH_3$ | N | |
| 6-Cl | $OCH_3$ | $CH_2OCH_3$ | N | |
| 6-Cl | $OCH_3$ | $NH_2$ | N | |
| 6-Cl | $OCH_3$ | $NHCH_3$ | N | |
| 6-Cl | $OCH_3$ | $N(CH_3)_2$ | N | |
| 4-$NO_2$ | $CH_3$ | $CH_3$ | CH | |
| 4-$NO_2$ | $OCH_3$ | $CH_3$ | CH | |
| 4-$NO_2$ | $OCH_3$ | $OCH_3$ | CH | |
| 4-$NO_2$ | $CH_3$ | $C_2H_5$ | CH | |
| 4-$NO_2$ | $OCH_3$ | $C_2H_5$ | CH | |
| 4-$NO_2$ | $CH_3$ | $OC_2H_5$ | CH | |
| 4-$NO_2$ | $OCH_3$ | $OC_2H_5$ | CH | |
| 4-$NO_2$ | $CH_3$ | $CH_2OCH_3$ | CH | |
| 4-$NO_2$ | $OCH_3$ | $CH_2OCH_3$ | CH | |
| 4-$NO_2$ | $OCH_3$ | $NH_2$ | CH | |
| 4-$NO_2$ | $OCH_3$ | $NHCH_3$ | CH | |
| 4-$NO_2$ | $OCH_3$ | $N(CH_3)_2$ | CH | |
| 4-$NO_2$ | $CH_3$ | $CH_3$ | N | |
| 4-$NO_2$ | $OCH_3$ | $CH_3$ | N | |
| 4-$NO_2$ | $OCH_3$ | $OCH_3$ | N | |
| 4-$NO_2$ | $CH_3$ | $C_2H_5$ | N | |
| 4-$NO_2$ | $OCH_3$ | $C_2H_5$ | N | |
| 4-$NO_2$ | $CH_3$ | $OC_2H_5$ | N | |
| 4-$NO_2$ | $OCH_3$ | $OC_2H_5$ | N | |
| 4-$NO_2$ | $CH_3$ | $CH_2OCH_3$ | N | |
| 4-$NO_2$ | $OCH_3$ | $CH_2OCH_3$ | N | |
| 4-$NO_2$ | $OCH_3$ | $NH_2$ | N | |
| 4-$NO_2$ | $OCH_3$ | $NHCH_3$ | N | |
| 4-$NO_2$ | $OCH_3$ | $N(CH_3)_2$ | N | |
| 6-$NO_2$ | $CH_3$ | $CH_3$ | CH | |
| 6-$NO_2$ | $OCH_3$ | $CH_3$ | CH | |
| 6-$NO_2$ | $OCH_3$ | $OCH_3$ | CH | |
| 6-$NO_2$ | $CH_3$ | $C_2H_5$ | CH | |
| 6-$NO_2$ | $OCH_3$ | $C_2H_5$ | CH | |
| 6-$NO_2$ | $CH_3$ | $OC_2H_5$ | CH | |
| 6-$NO_2$ | $OCH_3$ | $OC_2H_5$ | CH | |
| 6-$NO_2$ | $CH_3$ | $CH_2OCH_3$ | CH | |
| 6-$NO_2$ | $OCH_3$ | $CH_2OCH_3$ | CH | |
| 6-$NO_2$ | $OCH_3$ | $NH_2$ | CH | |
| 6-$NO_2$ | $OCH_3$ | $NHCH_3$ | CH | |
| 6-$NO_2$ | $OCH_3$ | $N(CH_3)_2$ | CH | |
| 6-$NO_2$ | $CH_3$ | $CH_3$ | N | |
| 6-$NO_2$ | $OCH_3$ | $CH_3$ | N | |
| 6-$NO_2$ | $OCH_3$ | $OCH_3$ | N | |
| 6-$NO_2$ | $CH_3$ | $C_2H_5$ | N | |
| 6-$NO_2$ | $OCH_3$ | $C_2H_5$ | N | |
| 6-$NO_2$ | $CH_3$ | $OC_2H_5$ | N | |
| 6-$NO_2$ | $OCH_3$ | $OC_2H_5$ | N | |
| 6-$NO_2$ | $CH_3$ | $CH_2OCH_3$ | N | |
| 6-$NO_2$ | $OCH_3$ | $CH_2OCH_3$ | N | |
| 6-$NO_2$ | $OCH_3$ | $NH_2$ | N | |
| 6-$NO_2$ | $OCH_3$ | $NHCH_3$ | N | |
| 6-$NO_2$ | $OCH_3$ | $N(CH_3)_2$ | N | |
| 6-Br | $CH_3$ | $CH_3$ | CH | |
| 6-Br | $CH_3$ | $OCH_3$ | CH | |
| 6-Br | $OCH_3$ | $OCH_3$ | CH | |
| 6-$OCH_3$ | $CH_3$ | $CH_3$ | CH | |
| 6-$OCH_3$ | $OCH_3$ | $CH_3$ | CH | |
| 6-$OCH_3$ | $OCH_3$ | $OCH_3$ | CH | |
| 6-$OC_2H_5$ | $CH_3$ | $CH_3$ | CH | |
| 6-$OC_2H_5$ | $CH_3$ | $OCH_3$ | CH | |
| 6-$OC_2H_5$ | $OCH_3$ | $OCH_3$ | CH | |
| 6-$OCH(CH_3)_2$ | $CH_3$ | $CH_3$ | CH | |
| 6-$OCH(CH_3)_2$ | $OCH_3$ | $CH_3$ | CH | |
| 6-$OCH(CH_3)_2$ | $OCH_3$ | $OCH_3$ | CH | |
| 6-$OCH_2CH_2CH_3$ | $CH_3$ | $CH_3$ | CH | |
| 6-$OCH_2CH_2CH_3$ | $OCH_3$ | $CH_3$ | CH | |
| 6-$OCH_2CH_2CH_3$ | $OCH_3$ | $OCH_3$ | CH | |
| 6-Br | $CH_3$ | $CH_3$ | N | |

TABLE Ib-continued

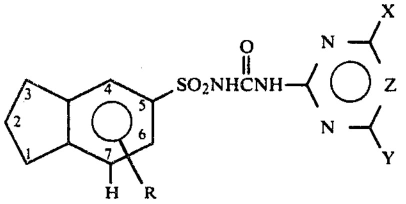

| R | X | Y | Z | m.p. (°C.) |
|---|---|---|---|---|
| 6-Br | $CH_3$ | $OCH_3$ | N | |
| 6-Br | $OCH_3$ | $OCH_3$ | N | |
| 6-$OCH_3$ | $CH_3$ | $CH_3$ | N | |
| 6-$OCH_3$ | $OCH_3$ | $CH_3$ | N | |
| 6-$OCH_3$ | $OCH_3$ | $OCH_3$ | N | |
| 6-$OC_2H_5$ | $CH_3$ | $CH_3$ | N | |
| 6-$OC_2H_5$ | $CH_3$ | $OCH_3$ | N | |
| 6-$OC_2H_5$ | $OCH_3$ | $OCH_3$ | N | |
| 6-$OCH(CH_3)_2$ | $CH_3$ | $CH_3$ | N | |
| 6-$OCH(CH_3)_2$ | $OCH_3$ | $CH_3$ | N | |
| 6-$OCH(CH_3)_2$ | $OCH_3$ | $OCH_3$ | N | |
| 6-$OCH_2CH_2CH_3$ | $CH_3$ | $CH_3$ | N | |
| 6-$OCH_2CH_2Ch_3$ | $OCH_3$ | $CH_3$ | N | |
| 6-$OCH_2CH_2CH_3$ | $OCH_3$ | $OCH_3$ | N | |
| 4-Br | $CH_3$ | $CH_3$ | CH | |
| 4-Br | $CH_3$ | $OCH_3$ | CH | |
| 4-Br | $OCH_3$ | $OCH_3$ | CH | |
| 4-$OCH_3$ | $CH_3$ | $CH_3$ | CH | |
| 4-$OCH_3$ | $OCH_3$ | $CH_3$ | CH | |
| 4-$OCH_3$ | $OCH_3$ | $OCH_3$ | CH | |
| 4-$OC_2H_5$ | $CH_3$ | $CH_3$ | CH | |
| 4-$OC_2H_5$ | $CH_3$ | $OCH_3$ | CH | |
| 4-$OC_2H_5$ | $OCH_3$ | $OCH_3$ | CH | |
| 4-$OCH(CH_3)_2$ | $CH_3$ | $CH_3$ | CH | |
| 4-$OCH(CH_3)_2$ | $OCH_3$ | $CH_3$ | CH | |
| 4-$OCH(CH_3)_2$ | $OCH_3$ | $OCH_3$ | CH | |
| 4-$OCH_2CH_2CH_3$ | $CH_3$ | $CH_3$ | CH | |
| 4-$OCH_2CH_2CH_3$ | $OCH_3$ | $CH_3$ | CH | |
| 4-$OCH_2CH_2CH_3$ | $OCH_3$ | $OCH_3$ | CH | |
| 4-Br | $CH_3$ | $CH_3$ | N | |
| 4-Br | $CH_3$ | $OCH_3$ | N | |
| 4-Br | $OCH_3$ | $OCH_3$ | N | |
| 4-$OCH_3$ | $CH_3$ | $CH_3$ | N | |
| 4-$OCH_3$ | $OCH_3$ | $CH_3$ | N | |
| 4-$OCH_3$ | $OCH_3$ | $OCH_3$ | N | |
| 4-$OC_2H_5$ | $CH_3$ | $CH_3$ | N | |
| 4-$OC_2H_5$ | $CH_3$ | $OCH_3$ | N | |
| 4-$OC_2H_5$ | $OCH_3$ | $OCH_3$ | N | |
| 4-$OCH(CH_3)_2$ | $CH_3$ | $CH_3$ | N | |
| 4-$OCH(CH_3)_2$ | $OCH_3$ | $CH_3$ | N | |
| 4-$OCH(CH_3)_2$ | $OCH_3$ | $OCH_3$ | N | |
| 4-$OCH_2CH_2CH_3$ | $CH_3$ | $CH_3$ | N | |
| 4-$OCH_2CH_2CH_3$ | $OCH_3$ | $CH_3$ | N | |
| 4-$OCH_2CH_2CH_3$ | $OCH_3$ | $OCH_3$ | N | |
| 4-$SO_2N(CH_3)_2$ | $CH_3$ | $CH_3$ | CH | |
| 4-$SO_2N(CH_3)_2$ | $CH_3$ | $OCH_3$ | CH | |
| 4-$SO_2N(CH_3)_2$ | $OCH_3$ | $OCH_3$ | CH | |
| 4-$SO_2N(C_2H_5)_2$ | $CH_3$ | $CH_3$ | CH | |
| 4-$SO_2N(C_2H_5)_2$ | $CH_3$ | $OCH_3$ | CH | |
| 4-$SO_2N(C_2H_5)_2$ | $OCH_3$ | $OCH_3$ | CH | |
| 4-$SO_2N(CH_3)C_2H_5$ | $CH_3$ | $CH_3$ | CH | |
| 4-$SO_2N(CH_3)C_2H_5$ | $CH_3$ | $OCH_3$ | CH | |
| 4-$SO_2N(CH_3)C_2H_5$ | $OCH_3$ | $OCH_3$ | CH | |
| 4-$SO_2N(CH_3)OCH_3$ | $CH_3$ | $CH_3$ | CH | |
| 4-$SO_2N(CH_3)OCH_3$ | $CH_3$ | $OCH_3$ | CH | |
| 4-$SO_2N(CH_3)OCH_3$ | $OCH_3$ | $OCH_3$ | CH | |
| 4-$OSO_2CF_3$ | $CH_3$ | $CH_3$ | CH | |
| 4-$OSO_2CF_3$ | $CH_3$ | $OCH_3$ | CH | |
| 4-$OSO_2CF_3$ | $OCH_3$ | $OCH_3$ | CH | |
| 4-$OSO_2CH_3$ | $CH_3$ | $CH_3$ | CH | |
| 4-$OSO_2CH_3$ | $CH_3$ | $OCH_3$ | CH | |
| 4-$OSO_2CH_3$ | $OCH_3$ | $OCH_3$ | CH | |
| 4-$OSO_2C_2H_5$ | $CH_3$ | $CH_3$ | CH | |
| 4-$OSO_2C_2H_5$ | $CH_3$ | $OCH_3$ | CH | |
| 4-$OSO_2C_2H_5$ | $OCH_3$ | $OCH_3$ | CH | |
| 4-$OSO_2$—n-$C_3H_7$ | $CH_3$ | $CH_3$ | CH | |
| 4-$OSO_2$—n-$C_3H_7$ | $CH_3$ | $OCH_3$ | CH | |
| 4-$OSO_2$—n-$C_3H_7$ | $OCH_3$ | $OCH_3$ | CH | |
| 4-$CO_2CH_3$ | $CH_3$ | $CH_3$ | CH | |
| 4-$CO_2CH_3$ | $CH_3$ | $OCH_3$ | CH | |

TABLE Ib-continued

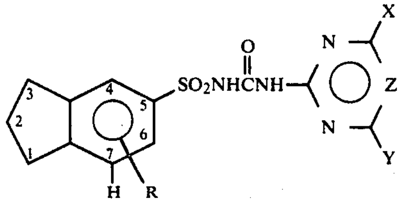

| R | X | Y | Z | m.p. (°C.) |
|---|---|---|---|---|
| 4-$CO_2CH_3$ | $OCH_3$ | $OCH_3$ | CH | |
| 4-$CO_2C_2H_5$ | $CH_3$ | $CH_3$ | CH | |
| 4-$CO_2C_2H_5$ | $CH_3$ | $OCH_3$ | CH | |
| 4-$CO_2C_2H_5$ | $OCH_3$ | $OCH_3$ | CH | |
| 4-$CO_2$—n-$C_3H_7$ | $CH_3$ | $CH_3$ | CH | |
| 4-$CO_2$—n-$C_3H_7$ | $CH_3$ | $OCH_3$ | CH | |
| 4-$CO_2$—n-$C_3H_7$ | $OCH_3$ | $OCH_3$ | CH | |
| 4-$CO_2$—i-$C_3H_7$ | $CH_3$ | $CH_3$ | CH | |
| 4-$CO_2$—i-$C_3H_7$ | $CH_3$ | $OCH_3$ | CH | |
| 4-$CO_2$—i-$C_3H_7$ | $OCH_3$ | $OCH_3$ | CH | |
| 4-$CO_2CH_2CH{=}CH_2$ | $CH_3$ | $CH_3$ | CH | |
| 4-$CO_2CH_2CH{=}CH_2$ | $CH_3$ | $OCH_3$ | CH | |
| 4-$CO_2CH_2CH{=}CH_2$ | $OCH_3$ | $OCH_3$ | CH | |
| 4-$CO_2CH_2CH_2OCH_3$ | $CH_3$ | $CH_3$ | CH | |
| 4-$CO_2CH_2CH_2OCH_3$ | $CH_3$ | $OCH_3$ | CH | |
| 4-$CO_2CH_2CH_2OCH_3$ | $OCH_3$ | $OCH_3$ | CH | |
| 4-$CO_2CH_2CH_2Cl$ | $CH_3$ | $CH_3$ | CH | |
| 4-$CO_2CH_2CH_2Cl$ | $CH_3$ | $OCH_3$ | CH | |
| 4-$CO_2CH_2CH_2Cl$ | $OCH_3$ | $OCH_3$ | CH | |
| 4-$SO_2CH_3$ | $CH_3$ | $CH_3$ | CH | |
| 4-$SO_2CH_3$ | $CH_3$ | $OCH_3$ | CH | |
| 4-$SO_2CH_3$ | $OCH_3$ | $OCH_3$ | CH | |
| 6-$SO_2N(CH_3)_2$ | $CH_3$ | $CH_3$ | CH | |
| 6-$SO_2N(CH_3)_2$ | $CH_3$ | $OCH_3$ | CH | |
| 6-$SO_2N(CH_3)_2$ | $OCH_3$ | $OCH_3$ | CH | |
| 6-$SO_2N(C_2H_5)_2$ | $CH_3$ | $CH_3$ | CH | |
| 6-$SO_2N(C_2H_5)_2$ | $CH_3$ | $OCH_3$ | CH | |
| 6-$SO_2N(C_2H_5)_2$ | $OCH_3$ | $OCH_3$ | CH | |
| 6-$SO_2N(CH_3)C_2H_5$ | $CH_3$ | $CH_3$ | CH | |
| 6-$SO_2N(CH_3)C_2H_5$ | $CH_3$ | $OCH_3$ | CH | |
| 6-$SO_2N(CH_3)C_2H_5$ | $OCH_3$ | $OCH_3$ | CH | |
| 6-$SO_2N(CH_3)OCH_3$ | $CH_3$ | $CH_3$ | CH | |
| 6-$SO_2N(CH_3)OCH_3$ | $CH_3$ | $OCH_3$ | CH | |
| 6-$SO_2N(CH_3)OCH_3$ | $OCH_3$ | $OCH_3$ | CH | |
| 6-$OSO_2CF_3$ | $CH_3$ | $CH_3$ | CH | |
| 6-$OSO_2CF_3$ | $CH_3$ | $OCH_3$ | CH | |
| 6-$OSO_2CF_3$ | $OCH_3$ | $OCH_3$ | CH | |
| 6-$OSO_2CH_3$ | $CH_3$ | $CH_3$ | CH | |
| 6-$OSO_2CH_3$ | $CH_3$ | $OCH_3$ | CH | |
| 6-$OSO_2CH_3$ | $OCH_3$ | $OCH_3$ | CH | |
| 6-$OSO_2C_2H_5$ | $CH_3$ | $CH_3$ | CH | |
| 6-$OSO_2C_2H_5$ | $CH_3$ | $OCH_3$ | CH | |
| 6-$OSO_2C_2H_5$ | $OCH_3$ | $OCH_3$ | CH | |
| 6-$OSO_2$—n-$C_3H_7$ | $CH_3$ | $CH_3$ | CH | |
| 6-$OSO_2$—n-$C_3H_7$ | $CH_3$ | $OCH_3$ | CH | |
| 6-$OSO_2$—n-$C_3H_7$ | $OCH_3$ | $OCH_3$ | CH | |
| 6-$CO_2CH_3$ | $CH_3$ | $CH_3$ | CH | |
| 6-$CO_2CH_3$ | $CH_3$ | $OCH_3$ | CH | |
| 6-$CO_2CH_3$ | $OCH_3$ | $OCH_3$ | CH | |
| 6-$CO_2C_2H_5$ | $CH_3$ | $CH_3$ | CH | |
| 6-$CO_2C_2H_5$ | $CH_3$ | $OCH_3$ | CH | |
| 6-$CO_2C_2H_5$ | $OCH_3$ | $OCH_3$ | CH | |
| 6-$CO_2$—n-$C_3H_7$ | $CH_3$ | $CH_3$ | CH | |
| 6-$CO_2$—n-$C_3H_7$ | $CH_3$ | $OCH_3$ | CH | |
| 6-$CO_2$—n-$C_3H_7$ | $OCH_3$ | $OCH_3$ | CH | |
| 6-$CO_2$—i-$C_3H_7$ | $CH_3$ | $CH_3$ | CH | |
| 6-$CO_2$—i-$C_3H_7$ | $CH_3$ | $OCH_3$ | CH | |
| 6-$CO_2$—i-$C_3H_7$ | $OCH_3$ | $OCH_3$ | CH | |
| 6-$CO_2CH_2CH{=}CH_2$ | $CH_3$ | $CH_3$ | CH | |
| 6-$CO_2CH_2CH{=}CH_2$ | $CH_3$ | $OCH_3$ | CH | |
| 6-$CO_2CH_2CH{=}CH_2$ | $OCH_3$ | $OCH_3$ | CH | |
| 6-$CO_2CH_2CH_2OCH_3$ | $CH_3$ | $CH_3$ | CH | |
| 6-$CO_2CH_2CH_2OCH_3$ | $CH_3$ | $OCH_3$ | CH | |
| 6-$CO_2CH_2CH_2OCH_3$ | $OCH_3$ | $OCH_3$ | CH | |
| 6-$CO_2CH_2CH_2Cl$ | $CH_3$ | $CH_3$ | CH | |
| 6-$CO_2CH_2CH_2Cl$ | $CH_3$ | $OCH_3$ | CH | |
| 6-$CO_2CH_2CH_2Cl$ | $OCH_3$ | $OCH_3$ | CH | |
| 6-$SO_2CH_3$ | $CH_3$ | $CH_3$ | CH | |
| 6-$SO_2CH_3$ | $CH_3$ | $OCH_3$ | CH | |
| 6-$SO_2CH_3$ | $OCH_3$ | $OCH_3$ | CH | |

TABLE Ib-continued

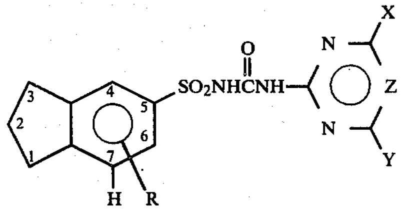

| R | X | Y | Z | m.p. (°C.) |
|---|---|---|---|---|
| 4-$SO_2N(CH_3)_2$ | $CH_3$ | $CH_3$ | N | |
| 4-$SO_2N(CH_3)_2$ | $CH_3$ | $OCH_3$ | N | |
| 4-$SO_2N(CH_3)_2$ | $OCH_3$ | $OCH_3$ | N | |
| 4-$SO_2N(C_2H_5)_2$ | $CH_3$ | $CH_3$ | N | |
| 4-$SO_2N(C_2H_5)_2$ | $CH_3$ | $OCH_3$ | N | |
| 4-$SO_2N(C_2H_5)_2$ | $OCH_3$ | $OCH_3$ | N | |
| 4-$SO_2N(CH_3)C_2H_5$ | $CH_3$ | $CH_3$ | N | |
| 4-$SO_2N(CH_3)C_2H_5$ | $CH_3$ | $OCH_3$ | N | |
| 4-$SO_2N(CH_3)C_2H_5$ | $OCH_3$ | $OCH_3$ | N | |
| 4-$SO_2N(CH_3)OCH_3$ | $CH_3$ | $CH_3$ | N | |
| 4-$SO_2N(CH_3)OCH_3$ | $CH_3$ | $OCH_3$ | N | |
| 4-$SO_2N(CH_3OCH_3$ | $OCH_3$ | $OCH_3$ | N | |
| 4-$OSO_2CF_3$ | $CH_3$ | $CH_3$ | N | |
| 4-$OSO_2CF_3$ | $CH_3$ | $OCH_3$ | N | |
| 4-$OSO_2CF_3$ | $OCH_3$ | $OCH_3$ | N | |
| 4-$OSO_2CH_3$ | $CH_3$ | $CH_3$ | N | |
| 4-$OSO_2CH_3$ | $CH_3$ | $OCH_3$ | N | |
| 4-$OSO_2CH_3$ | $OCH_3$ | $OCH_3$ | N | |
| 4-$OSO_2C_2H_5$ | $CH_3$ | $CH_3$ | N | |
| 4-$OSO_2C_2H_5$ | $CH_3$ | $OCH_3$ | N | |
| 4-$OSO_2C_2H_5$ | $OCH_3$ | $OCH_3$ | N | |
| 4-$OSO_2$—n-$C_3H_7$ | $CH_3$ | $CH_3$ | N | |
| 4-$OSO_2$—n-$C_3H_7$ | $CH_3$ | $OCH_3$ | N | |
| 4-$OSO_2$—n-$C_3H_7$ | $OCH_3$ | $OCH_3$ | N | |
| 4-$CO_2CH_3$ | $CH_3$ | $CH_3$ | N | |
| 4-$CO_2CH_3$ | $CH_3$ | $OCH_3$ | N | |
| 4-$CO_2CH_3$ | $OCH_3$ | $OCH_3$ | N | |
| 4-$CO_2C_2H_5$ | $CH_3$ | $CH_3$ | N | |
| 4-$CO_2C_2H_5$ | $CH_3$ | $OCH_3$ | N | |
| 4-$CO_2C_2H_5$ | $OCH_3$ | $OCH_3$ | N | |
| 4-$CO_2$—n-$C_3H_7$ | $CH_3$ | $CH_3$ | N | |
| 4-$CO_2$—n-$C_3H_7$ | $CH_3$ | $OCH_3$ | N | |
| 4-$CO_2$—n-$C_3H_7$ | $OCH_3$ | $OCH_3$ | N | |
| 4-$CO_2$—i-$C_3H_7$ | $CH_3$ | $CH_3$ | N | |
| 4-$CO_2$—i-$C_3H_7$ | $CH_3$ | $OCH_3$ | N | |
| 4-$CO_2$—i-$C_3H_7$ | $OCH_3$ | $OCH_3$ | N | |
| 4-$CO_2CH_2CH{=}CH_2$ | $CH_3$ | $CH_3$ | N | |
| 4-$CO_2CH_2CH{=}CH_2$ | $CH_3$ | $OCH_3$ | N | |
| 4-$CO_2CH_2CH{=}CH_2$ | $OCH_3$ | $OCH_3$ | N | |
| 4-$CO_2CH_2CH_2OCH_3$ | $CH_3$ | $CH_3$ | N | |
| 4-$CO_2CH_2CH_2OCH_3$ | $CH_3$ | $OCH_3$ | N | |
| 4-$CO_2CH_2CH_2OCH_3$ | $OCH_3$ | $OCH_3$ | N | |
| 4-$CO_2CH_2CH_2Cl$ | $CH_3$ | $CH_3$ | N | |
| 4-$CO_2CH_2CH_2Cl$ | $CH_3$ | $OCH_3$ | N | |
| 4-$CO_2CH_2CH_2Cl$ | $OCH_3$ | $OCH_3$ | N | |
| 4-$SO_2CH_3$ | $CH_3$ | $CH_3$ | N | |
| 4-$SO_2CH_3$ | $CH_3$ | $OCH_3$ | N | |
| 4-$SO_2CH_3$ | $OCH_3$ | $OCH_3$ | N | |
| 6-$SO_2N(CH_3)_2$ | $CH_3$ | $CH_3$ | N | |
| 6-$SO_2N(CH_3)_2$ | $CH_3$ | $OCH_3$ | N | |
| 6-$SO_2N(CH_3)_2$ | $OCH_3$ | $OCH_3$ | N | |
| 6-$SO_2N(C_2H_5)_2$ | $CH_3$ | $CH_3$ | N | |
| 6-$SO_2N(C_2H_5)_2$ | $CH_3$ | $OCH_3$ | N | |
| 6-$SO_2N(C_2H_5)_2$ | $OCH_3$ | $OCH_3$ | N | |
| 6-$SO_2N(CH_3)C_2H_5$ | $CH_3$ | $CH_3$ | N | |
| 6-$SO_2N(CH_3)C_2H_5$ | $CH_3$ | $OCH_3$ | N | |
| 6-$SO_2N(CH_3)C_2H_5$ | $OCH_3$ | $OCH_3$ | N | |
| 6-$SO_2N(CH_3)OCH_3$ | $CH_3$ | $CH_3$ | N | |
| 6-$SO_2N(CH_3)OCH_3$ | $CH_3$ | $OCH_3$ | N | |
| 6-$SO_2N(CH_3)OCH_3$ | $OCH_3$ | $OCH_3$ | N | |
| 6-$OSO_2CF_3$ | $CH_3$ | $CH_3$ | N | |
| 6-$OSO_2CF_3$ | $CH_3$ | $OCH_3$ | N | |
| 6-$OSO_2CF_3$ | $OCH_3$ | $OCH_3$ | N | |
| 6-$OSO_2CH_3$ | $CH_3$ | $CH_3$ | N | |
| 6-$OSO_2CH_3$ | $CH_3$ | $OCH_3$ | N | |
| 6-$OSO_2CH_3$ | $OCH_3$ | $OCH_3$ | N | |
| 6-$OSO_2C_2H_5$ | $CH_3$ | $CH_3$ | N | |
| 6-$OSO_2C_2H_5$ | $CH_3$ | $OCH_3$ | N | |
| 6-$OSO_2C_2H_5$ | $OCH_3$ | $OCH_3$ | N | |
| 6-$OSO_2$—n-$C_3H_7$ | $CH_3$ | $CH_3$ | N | |

TABLE Ib-continued

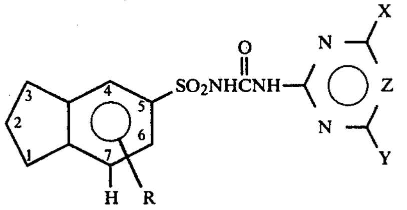

| R | X | Y | Z | m.p. (°C.) |
|---|---|---|---|---|
| 6-$OSO_2$—n-$C_3H_7$ | $CH_3$ | $OCH_3$ | N | |
| 6-$OSO_2$—n-$C_3H_7$ | $OCH_3$ | $OCH_3$ | N | |
| 6-$CO_2CH_3$ | $CH_3$ | $CH_3$ | N | |
| 6-$CO_2CH_3$ | $CH_3$ | $OCH_3$ | N | |
| 6-$CO_2CH_3$ | $OCH_3$ | $OCH_3$ | N | |
| 6-$CO_2C_2H_5$ | $CH_3$ | $CH_3$ | N | |
| 6-$CO_2C_2H_5$ | $CH_3$ | $OCH_3$ | N | |
| 6-$CO_2C_2H_5$ | $OCH_3$ | $OCH_3$ | N | |
| 6-$CO_2$—n-$C_3H_7$ | $CH_3$ | $CH_3$ | N | |
| 6-$CO_2$—n-$C_3H_7$ | $CH_3$ | $OCH_3$ | N | |
| 6-$CO_2$—n-$C_3H_7$ | $OCH_3$ | $OCH_3$ | N | |
| 6-$CO_2$—i-$C_3H_7$ | $CH_3$ | $CH_3$ | N | |
| 6-$CO_2$—i-$C_3H_7$ | $CH_3$ | $OCH_3$ | N | |
| 6-$CO_2$—i-$C_3H_7$ | $OCH_3$ | $OCH_3$ | N | |
| 6-$CO_2CH_2CH{=}CH_2$ | $CH_3$ | $CH_3$ | N | |
| 6-$CO_2CH_2CH{=}CH_2$ | $CH_3$ | $OCH_3$ | N | |
| 6-$CO_2CH_2CH{=}CH_2$ | $OCH_3$ | $OCH_3$ | N | |
| 6-$CO_2CH_2CH_2OCH_3$ | $CH_3$ | $CH_3$ | N | |
| 6-$CO_2CH_2CH_2OCH_3$ | $CH_3$ | $OCH_3$ | N | |
| 6-$CO_2CH_2CH_2OCH_3$ | $OCH_3$ | $OCH_3$ | N | |
| 6-$CO_2CH_2CH_2Cl$ | $CH_3$ | $CH_3$ | N | |
| 6-$CO_2CH_2CH_2Cl$ | $CH_3$ | $OCH_3$ | N | |
| 6-$CO_2CH_2CH_2Cl$ | $OCH_3$ | $OCH_3$ | N | |
| 6-$SO_2CH_3$ | $CH_3$ | $CH_3$ | N | |
| 6-$SO_2CH_3$ | $CH_3$ | $OCH_3$ | N | |
| 6-$SO_2CH_3$ | $OCH_3$ | $OCH_3$ | N | |
| H | $CH_3$ | $CH(OCH_3)_2$ | N | |
| H | $OCH_3$ | $CH(OCH_3)_2$ | N | |
| H | $CH_3$ | 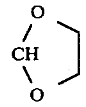 | N | |
| H | $OCH_3$ | 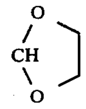 | N | |
| H | Cl | $OCH_3$ | CH | |
| H | Cl | $NH_2$ | CH | |
| H | Cl | $NHCH_3$ | CH | |
| H | Cl | $N(CH_3)_2$ | CH | |
| 4-Cl | $CH_3$ | $CH(OCH_3)_2$ | CH | |
| 4-Cl | $CH_3$ | $CH(OCH_3)_2$ | N | |
| 4-Cl | $OCH_3$ | $CH(OCH_3)_2$ | CH | |
| 4-Cl | $OCH_3$ | $CH(OCH_3)_2$ | N | |
| 4-Cl | $CH_3$ | 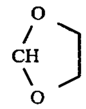 | CH | |
| 4-Cl | $CH_3$ | 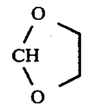 | N | |
| 4-Cl | $OCH_3$ | 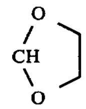 | CH | |

TABLE Ib-continued

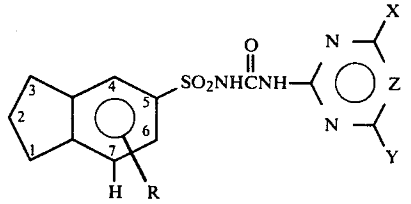

| R | X | Y | Z | m.p. (°C.) |
|---|---|---|---|---|
| 4-Cl | $OCH_3$ | 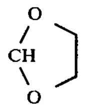 | N | |
| 4-Cl | Cl | $OCH_3$ | CH | |
| 6-Cl | $CH_3$ | $CH(OCH_3)_2$ | CH | |
| 6-Cl | Cl | $OCH_3$ | CH | |
| 6-Cl | $OCH_3$ | $CH(OCH_3)_2$ | N | |
| 4-$NO_2$ | $CH_3$ | $CH(OCH_3)_2$ | N | |
| 4-$NO_2$ | $CH_3$ | $CH(OCH_3)_2$ | CH | |
| 4-$NO_2$ | $OCH_3$ | $CH(OCH_3)_2$ | N | |
| 4-$NO_2$ | $OCH_3$ | $CH(OCH_3)_2$ | CH | |
| 4-$NO_2$ | Cl | $OCH_3$ | CH | |
| 4-Br | $CH_3$ | $CH(OCH_3)_2$ | CH | |
| 4-Br | $CH_3$ | $CH(OCH_3)_2$ | N | |
| 4-Br | $OCH_3$ | $CH(OCH_3)_2$ | CH | |
| 4-Br | $OCH_3$ | $CH(OCH_3)_2$ | N | |
| 4-Br | Cl | $OCH_3$ | CH | |
| 4-$OCH_3$ | Cl | $OCH_3$ | CH | |
| 4-$OC_2H_5$ | Cl | $OCH_3$ | CH | |
| 4-$OCH(CH_3)_2$ | Cl | $OCH_3$ | CH | |
| 4-$SO_2N(CH_3)_2$ | Cl | $OCH_3$ | CH | |
| 4-$SO_2N(C_2H_5)_2$ | Cl | $OCH_3$ | CH | |
| 4-$OSO_2CH_3$ | Cl | $OCH_3$ | CH | |
| 4-$OSO_2CF_3$ | Cl | $OCH_3$ | CH | |
| 4-$SO_2CH_3$ | Cl | $OCH_3$ | CH | |
| 4-$SO_2C_2H_5$ | Cl | $OCH_3$ | CH | |
| 4-$SO_2CH_2CH_2CH_3$ | Cl | $OCH_3$ | CH | |
| 4-$OSO_2CH_2CH_2CH_3$ | Cl | $OCH_3$ | CH | |
| 4-$CO_2CH_3$ | Cl | $OCH_3$ | CH | |
| 4-$CO_2C_2H_5$ | Cl | $OCH_3$ | CH | |
| 4-$CO_2CH(CH_3)_2$ | Cl | $OCH_3$ | CH | |
| 4-$CO_2CH_2CH_2OCH_3$ | Cl | $OCH_3$ | CH | |
| 4-$OCF_2CF_2H$ | Cl | $OCH_3$ | CH | |
| 4-$C_2H_5$ | Cl | $OCH_3$ | CH | |
| 4-$CH(CH_3)_2$ | Cl | $OCH_3$ | CH | |
| 4-$CH_2CH_2CH_3$ | Cl | $OCH_3$ | CH | |
| 4-$SCH_3$ | Cl | $OCH_3$ | CH | |
| 4-$SC_2H_5$ | Cl | $OCH_3$ | CH | |
| 4-$SCH_2CH_2CH_3$ | Cl | $OCH_3$ | CH | |
| 6-Br | Cl | $OCH_3$ | CH | |
| 6-$OCH_3$ | Cl | $OCH_3$ | CH | |
| 6-$OC_2H_5$ | Cl | $OCH_3$ | CH | |
| 6-$OCH(CH_3)_2$ | Cl | $OCH_3$ | CH | |
| 6-$SO_2N(CH_3)_2$ | Cl | $OCH_3$ | CH | |
| 6-$SO_2N(C_2H_5)_2$ | Cl | $OCH_3$ | CH | |
| 6-$OSO_2CH_3$ | Cl | $OCH_3$ | CH | |
| 6-$OSO_2CF_3$ | Cl | $OCH_3$ | CH | |
| 6-$SO_2CH_3$ | Cl | $OCH_3$ | CH | |
| 6-$SO_2C_2H_5$ | Cl | $OCH_3$ | CH | |
| 6-$SO_2CH_2CH_2CH_3$ | Cl | $OCH_3$ | CH | |
| 6-$OSO_2CH_2CH_2CH_3$ | Cl | $OCH_3$ | CH | |
| 6-$CO_2CH_3$ | Cl | $OCH_3$ | CH | |
| 6-$CO_2C_2H_5$ | Cl | $OCH_3$ | CH | |
| 6-$CO_2CH(CH_3)_2$ | Cl | $OCH_3$ | CH | |
| 6-$CO_2CH_2CH_2OCH_3$ | Cl | $OCH_3$ | CH | |
| 6-$OCF_2CF_2H$ | Cl | $OCH_3$ | CH | |
| 6-$SCF_2H$ | Cl | $OCH_3$ | CH | |
| 6-$OCF_2H$ | Cl | $OCH_3$ | CH | |
| 6-$OCF_3$ | Cl | $OCH_3$ | CH | |
| 6-$C_2H_5$ | Cl | $OCH_3$ | CH | |
| 6-$CH(CH_3)_2$ | Cl | $OCH_3$ | CH | |
| 6-$SCH_3$ | Cl | $OCH_3$ | CH | |
| 6-$SC_2H_5$ | Cl | $OCH_3$ | CH | |
| 4-$SCF_2H$ | Cl | $OCH_3$ | CH | |
| 4-$OCF_2H$ | Cl | $OCH_3$ | CH | |

TABLE Ib-continued

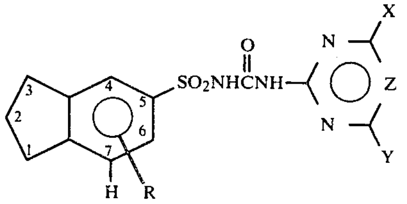

| R | X | Y | Z | m.p. (°C.) |
|---|---|---|---|---|
| 4-$OCF_3$ | Cl | $OCH_3$ | CH | |

TABLE Ic

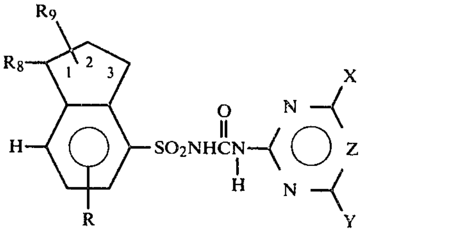

| R | $R_9$ | $R_8$ | X | Y | Z | m.p.(°C.) |
|---|---|---|---|---|---|---|
| H | 1-$CH_3$ | H | $CH_3$ | $CH_3$ | CH | |
| H | 1-$CH_3$ | H | $OCH_3$ | $OCH_3$ | CH | |
| H | 1-$CH_3$ | H | $OCH_3$ | $CH_3$ | CH | |
| H | 1-$CH_3$ | H | $OCH_3$ | $SCH_3$ | CH | |
| H | 2-$CH_3$ | $CH_3$ | $OCH_3$ | $CH_3$ | CH | |
| H | 2-$CH_3$ | $CH_3$ | $OCH_3$ | $OCH_3$ | CH | |
| H | 2-$CH_3$ | H | $CH_3$ | $CH_3$ | CH | |
| H | 3-$CH_3$ | $CH_3$ | $CH_3$ | $CH_3$ | CH | |
| H | 3-$CH_3$ | H | $OCH_3$ | $CH_3$ | CH | |
| H | 3-$CH_3$ | H | $OCH_3$ | $OCH_3$ | CH | |
| 5-Cl | 1-$CH_3$ | H | $CH_3$ | $CH_3$ | CH | |
| 5-Cl | 1-$CH_3$ | H | $OCH_3$ | $OCH_3$ | CH | |
| 5-Cl | 1-$CH_3$ | H | $OCH_3$ | $CH_3$ | CH | |
| 6-Cl | 1-$CH_3$ | H | $CH_3$ | $CH_3$ | CH | |
| 6-Cl | 1-$CH_3$ | H | $OCH_3$ | $OCH_3$ | CH | |
| 6-Cl | 1-$CH_3$ | H | $OCH_3$ | $CH_3$ | CH | |
| 5-$NO_2$ | 1-$CH_3$ | H | $CH_3$ | $CH_3$ | CH | |
| 5-$NO_2$ | 1-$CH_3$ | H | $OCH_3$ | $OCH_3$ | CH | |
| 5-$NO_2$ | 1-$CH_3$ | H | $OCH_3$ | $CH_3$ | CH | |
| 5-Br | 1-$CH_3$ | H | $CH_3$ | $CH_3$ | CH | |
| 5-Br | 1-$CH_3$ | H | $OCH_3$ | $OCH_3$ | CH | |
| 5-Br | 1-$CH_3$ | H | $OCH_3$ | $CH_3$ | CH | |
| 5-$OCH_3$ | 1-$CH_3$ | H | $CH_3$ | $CH_3$ | CH | |
| 5-$OCH_3$ | 1-$CH_3$ | H | $OCH_3$ | $OCH_3$ | CH | |
| 5-$OCH_3$ | 1-$CH_3$ | H | $OCH_3$ | $CH_3$ | CH | |
| H | 1-$CH_3$ | H | $OCH_3$ | $SCH_3$ | N | |
| 5-$CO_2CH_3$ | 1-$CH_3$ | H | $CH_3$ | $CH_3$ | CH | |
| 5-$CO_2CH_3$ | 1-$CH_3$ | H | $OCH_3$ | $CH_3$ | CH | |
| 5-$CO_2CH_3$ | 1-$CH_3$ | H | $OCH_3$ | $OCH_3$ | CH | |
| 5-$CO_2CH_3$ | 1-$CH_3$ | H | Cl | $OCH_3$ | CH | |
| 5-$CO_2CH_3$ | 1-$CH_3$ | H | Cl | $N(CH_3)_2$ | CH | |
| 5-$CO_2C_2H_5$ | 1-$CH_3$ | H | Cl | $OCH_3$ | CH | |
| 5-$CO_2C_2H_5$ | 1-$CH_3$ | H | $CH_3$ | $OCH_3$ | N | |
| 5-$CO_2C_2H_5$ | 1-$CH_3$ | H | $OCH_3$ | $CH_3$ | N | |
| 5-$CO_2C_2H_5$ | 1-$CH_3$ | H | $OCH_3$ | $OCH_3$ | N | |
| 5-$SO_2CH_3$ | 1-$CH_3$ | H | $OCH_3$ | $CH_3$ | CH | |
| 5-$SO_2CH_3$ | 1-$CH_3$ | H | $OCH_3$ | $CH_3$ | N | |
| 5-$SO_2CH_3$ | 1-$CH_3$ | H | $OCH_3$ | $OCH_3$ | CH | |
| 5-$SO_2CH_3$ | 1-$CH_3$ | $CH_3$ | $OCH_3$ | $OCH_3$ | N | |
| 5-$SO_2CH_3$ | 1-$CH_3$ | H | Cl | $OCH_3$ | CH | |
| 5-$OSO_2CF_3$ | 1-$CH_3$ | $CH_3$ | $OCH_3$ | $OCH_3$ | CH | |
| 5-$OSO_2CF_3$ | 1-$CH_3$ | H | $OCH_3$ | $CH_3$ | N | |
| 5-$OSO_2CH_3$ | 1-$CH_3$ | $CH_3$ | Cl | $OCH_3$ | CH | |
| 5-$SO_2N(CH_3)_2$ | 1-$CH_3$ | $CH_3$ | Cl | $OCH_3$ | CH | |
| 5-$SCH_3$ | 1-$CH_3$ | $CH_3$ | $CH_3$ | $OCH_3$ | CH | |
| 5-$SCH_3$ | 1-$CH_3$ | $CH_3$ | $CH_3$ | $CH_3$ | CH | |
| 5-$SCH_3$ | 1-$CH_3$ | $CH_3$ | $OCH_3$ | $OCH_3$ | CH | |
| 5-$SO_2CH_3$ | 3-$CH_3$ | $CH_3$ | $OCH_3$ | $OCH_3$ | CH | |
| 5-$SO_2CH_3$ | 3-$CH_3$ | $CH_3$ | $OCH_3$ | $CH_3$ | CH | |
| 5-$SO_2CH_3$ | 3-$CH_3$ | $CH_3$ | $CH_3$ | $CH_3$ | CH | |
| 5-$SCF_2H$ | 3-$CH_3$ | H | $CH_3$ | $CH_3$ | CH | |
| 5-$SCF_2H$ | 3-$CH_3$ | H | $OCH_3$ | $CH_3$ | CH | |

TABLE Ic-continued

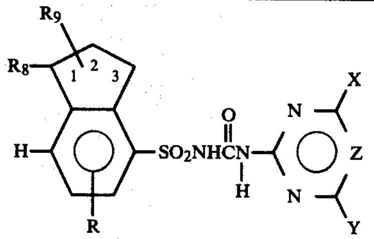

| R | R9 | R8 | X | Y | Z m.p.(°C.) |
|---|---|---|---|---|---|
| 5-SCF2H | 3-CH3 | H | OCH3 | OCH3 | CH |
| 5-CO2CH3 | 2-CH3 | CH3 | OCH3 | CH3 | CH |
| 5-CO2CH3 | 2-CH3 | CH3 | Cl | OCH3 | CH |
| 5-CO2CH3 | 2-CH3 | CH3 | OCH3 | OCH3 | CH |
| 5-CO2CH3 | 2-CH3 | CH3 | CH3 | OCH3 | N |
| 5-CO2CH3 | 2-CH3 | CH3 | OCH3 | OCH3 | N |

TABLE Id

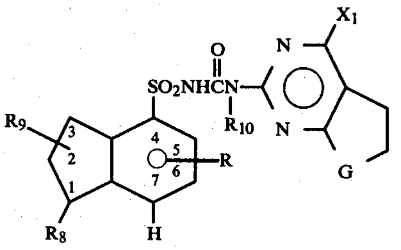

| R | R8 | R9 | R10 | G | X1 m.p.(°C.) |
|---|---|---|---|---|---|
| H | H | H | H | O | CH3 |
| 5-Cl | H | H | H | O | CH3 |
| 5-Br | H | H | H | O | CH3 |
| 5-OCH3 | H | H | H | O | CH3 |
| 5-SO2CH3 | H | H | H | O | CH3 |
| 5-SCH3 | H | H | H | O | CH3 |
| 5-CO2CH3 | H | H | H | O | CH3 |
| 5-SO2N(CH3)2 | H | H | H | O | CH3 |
| 5-SO2N(OCH3)CH3 | H | H | H | O | CH3 |
| 5-OSO2CH3 | H | H | H | O | CH3 |
| 5-OSO2CF3 | H | H | H | O | CH3 |
| 5-CH3 | CH3 | H | H | O | CH3 |
| 6-Cl | CH3 | H | H | O | CH3 |
| 6-CH3 | CH3 | H | H | O | CH3 |
| 6-OCH3 | CH3 | H | H | O | CH3 |
| 6-NO2 | CH3 | H | H | O | CH3 |
| 6-Br | CH3 | H | H | O | CH3 |
| H | CH3 | H | H | O | OCH3 |
| 5-Cl | Cl | H | H | O | OCH3 |
| 5-Br | Cl | H | H | O | OCH3 |
| 5-CO2CH3 | Cl | H | H | O | OCH3 |
| 5-SO2CH3 | CH3 | H | H | O | OCH3 |
| 5-SCH3 | CH3 | H | H | O | OCH3 |
| 5-OCH3 | Cl | H | H | O | OCH3 |
| 5-SO2N(CH3)2 | CH3 | H | H | O | OCH3 |
| 5-OSO2CH3 | CH3 | H | H | O | OCH3 |
| 5-OSO2CF3 | Cl | H | H | O | OCH3 |
| 6-Cl | CH3 | H | H | O | OCH3 |
| 6-CH3 | H | H | H | O | OCH3 |
| 6-OCH3 | H | H | H | O | OCH3 |
| 6-NO2 | H | H | H | O | OCH3 |
| 6-Br | H | H | H | O | OCH3 |
| H | H | H | H | CH2 | CH3 |
| 5-Cl | H | H | H | CH2 | CH3 |
| 5-Br | H | H | H | CH2 | CH3 |
| 5-OCH3 | H | H | H | CH2 | CH3 |
| 5-SO2CH3 | H | H | H | CH2 | CH3 |
| 5-SCH3 | H | H | H | CH2 | CH3 |
| 5-SO2N(CH3)2 | H | H | H | CH2 | CH3 |
| 5-SO2N(OCH3)CH3 | H | H | H | CH2 | CH3 |
| 5-OSO2CH3 | H | H | H | CH2 | CH3 |
| 5-OSO2CF3 | H | H | H | CH2 | CH3 |
| 5-CH3 | H | H | H | CH2 | CH3 |
| 6-Cl | CH3 | H | H | CH2 | CH3 |
| 6-CH3 | CH3 | H | H | CH2 | CH3 |

TABLE Id-continued

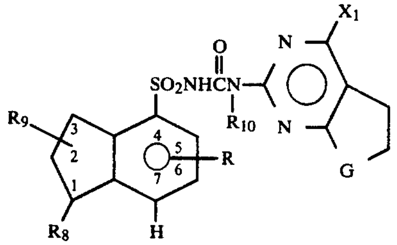

| R | R8 | R9 | R10 | G | X1 m.p.(°C.) |
|---|---|---|---|---|---|
| 6-OCH3 | CH3 | H | H | CH2 | CH3 |
| 6-NO2 | CH3 | H | H | CH2 | CH3 |
| 6-Br | H | H | H | CH2 | CH3 |
| H | H | H | H | CH2 | OCH3 |
| 5-Cl | H | H | H | CH2 | OCH3 |
| 5-Br | H | H | H | CH2 | OCH3 |
| 5-OCH3 | H | H | H | CH2 | OCH3 |
| 5-SO2CH3 | H | H | H | CH2 | OCH3 |
| 5-SCH3 | H | H | H | CH2 | OCH3 |
| 5-CO2CH3 | H | H | H | CH2 | OCH3 |
| 5-OSO2CH3 | H | H | H | CH2 | OCH3 |
| 5-CH3 | H | H | H | CH2 | OCH3 |
| 6-Cl | H | H | H | CH2 | OCH3 |
| 6-CH3 | H | H | H | CH2 | OCH3 |
| 6-OCH3 | H | H | H | CH2 | OCH3 |
| 6-NO2 | H | H | H | CH2 | OCH3 |
| 6-Br | H | H | H | CH2 | OCH3 |
| H | H | 1-CH3 | H | O | CH3 |
| H | H | 1-CH3 | H | O | OCH3 |
| H | H | 1-CH3 | H | CH2 | CH3 |
| H | H | 1-CH3 | H | CH2 | OCH3 |
| H | H | 2-CH3 | H | O | CH3 |
| H | H | 2-CH3 | H | O | OCH3 |
| H | H | 2-CH3 | H | CH2 | CH3 |
| H | H | 2-CH3 | H | CH2 | OCH3 |
| H | H | 3-CH3 | H | O | CH3 |
| H | H | 3-CH3 | H | O | OCH3 |
| H | H | 3-CH3 | H | CH2 | CH3 |
| H | H | 3-CH3 | H | CH2 | OCH3 |
| H | H | H | CH3 | O | CH3 |
| H | H | H | CH3 | O | OCH3 |
| H | H | H | CH3 | CH2 | CH3 |
| H | H | H | CH3 | CH2 | OCH3 |

TABLE Ie

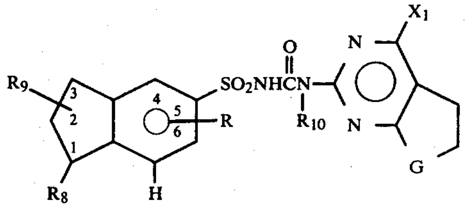

| R | R8 | R9 | R10 | G | X1 m.p.(°C.) |
|---|---|---|---|---|---|
| H | H | H | H | O | CH3 |
| 4-Cl | H | H | H | O | CH3 |
| 4-Br | H | H | H | O | CH3 |
| 4-NO2 | H | H | H | O | CH3 |
| 4-OCH3 | H | H | H | O | CH3 |
| 4-SCH3 | H | H | H | O | CH3 |
| 4-SO2CH3 | H | H | H | O | CH3 |
| 4-CO2CH3 | H | H | H | O | CH3 |
| 4-SO2N(CH3)2 | H | H | H | O | CH3 |
| 4-OSO2CH3 | H | H | H | O | CH3 |
| 6-Cl | H | H | H | O | CH3 |
| 6-Br | H | H | H | O | CH3 |
| 6-NO2 | H | H | H | O | CH3 |
| 6-OCH3 | H | H | H | O | CH3 |
| 6-SCH3 | H | H | H | O | CH3 |
| 6-SO2CH3 | H | H | H | O | CH3 |
| 6-CO2CH3 | H | H | H | O | CH3 |
| 6-SO2N(CH3)2 | H | H | H | O | CH3 |
| 6-OSO2CH3 | H | H | H | O | CH3 |

TABLE Ie-continued

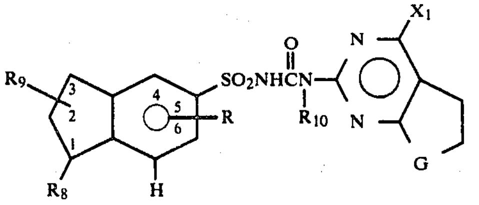

| R | $R_8$ | $R_9$ | $R_{10}$ | G | $X_1$ m.p.(°C.) |
|---|---|---|---|---|---|
| H | H | H | H | O | $OCH_3$ |
| 4-Cl | H | H | H | O | $OCH_3$ |
| 4-Br | H | H | H | O | $OCH_3$ |
| 4-$NO_2$ | H | H | H | O | $OCH_3$ |
| 4-$OCH_3$ | H | H | H | O | $OCH_3$ |
| 4-$SCH_3$ | H | H | H | O | $OCH_3$ |
| 4-$SO_2CH_3$ | H | H | H | O | $OCH_3$ |
| 4-$CO_2CH_3$ | $CH_3$ | H | H | O | $OCH_3$ |
| 4-$SO_2N(CH_3)_2$ | $CH_3$ | H | H | O | $OCH_3$ |
| 4-$OSO_2CH_3$ | $CH_3$ | H | H | O | $OCH_3$ |
| 6-Cl | $CH_3$ | H | H | O | $OCH_3$ |
| 6-Br | $CH_3$ | H | H | O | $OCH_3$ |
| 6-$NO_2$ | $CH_3$ | H | H | O | $OCH_3$ |
| 6-$OCH_3$ | H | H | H | O | $OCH_3$ |
| 6-$SCH_3$ | H | H | H | O | $OCH_3$ |
| 6-$SO_2CH_3$ | H | H | H | O | $OCH_3$ |
| 6-$CO_2CH_3$ | H | H | H | O | $OCH_3$ |
| 6-$SO_2N(CH_3)_2$ | H | H | H | O | $OCH_3$ |
| 6-$OSO_2CH_3$ | H | H | H | O | $OCH_3$ |
| H | H | H | H | $CH_2$ | $CH_3$ |
| 4-Cl | H | H | H | $CH_2$ | $CH_3$ |
| 4-Br | H | H | H | $CH_2$ | $CH_3$ |
| 4-$NO_2$ | H | H | H | $CH_2$ | $CH_3$ |
| 4-$OCH_3$ | H | H | H | $CH_2$ | $CH_3$ |
| 4-$SCH_3$ | H | H | H | $CH_2$ | $CH_3$ |
| 4-$SO_2CH_3$ | H | H | H | $CH_2$ | $CH_3$ |
| 4-$CO_2CH_3$ | H | H | H | $CH_2$ | $CH_3$ |
| 4-$SO_2N(CH_3)_2$ | H | H | H | $CH_2$ | $CH_3$ |
| 4-$OSO_2CH_3$ | H | H | H | $CH_2$ | $CH_3$ |
| 6-Cl | H | H | H | $CH_2$ | $CH_3$ |
| 6-Br | H | H | H | $CH_2$ | $CH_3$ |
| 6-$NO_2$ | H | H | H | $CH_2$ | $CH_3$ |
| 6-$OCH_3$ | H | H | H | $CH_2$ | $CH_3$ |
| 6-$SCH_3$ | H | H | H | $CH_2$ | $CH_3$ |
| 6-$SO_2CH_3$ | H | H | H | $CH_2$ | $CH_3$ |
| 6-$CO_2CH_3$ | H | H | H | $CH_2$ | $CH_3$ |
| 6-$SO_2N(CH_3)_2$ | H | H | H | $CH_2$ | $CH_3$ |
| 6-$OSO_2CH_3$ | H | H | H | $CH_2$ | $CH_3$ |
| H | H | H | H | $CH_2$ | $OCH_3$ |
| 4-Cl | H | H | H | $CH_2$ | $OCH_3$ |
| 4-Br | H | H | H | $CH_2$ | $OCH_3$ |
| 4-$NO_2$ | H | H | H | $CH_2$ | $OCH_3$ |
| 4-$OCH_3$ | H | H | H | $CH_2$ | $OCH_3$ |
| 4-$SCH_3$ | H | H | H | $CH_2$ | $OCH_3$ |
| 4-$SO_2CH_3$ | H | H | H | $CH_2$ | $OCH_3$ |
| 4-$CO_2CH_3$ | H | H | H | $CH_2$ | $OCH_3$ |
| 4-$SO_2N(CH_3)_2$ | H | H | H | $CH_2$ | $OCH_3$ |
| 4-$OSO_2CH_3$ | H | H | H | $CH_2$ | $OCH_3$ |
| 6-Cl | H | H | H | $CH_2$ | $OCH_3$ |
| 6-Br | H | H | H | $CH_2$ | $OCH_3$ |
| 6-$NO_2$ | H | H | H | $CH_2$ | $OCH_3$ |
| 6-$OCH_3$ | H | H | H | $CH_2$ | $OCH_3$ |
| 6-$SCH_3$ | H | H | H | $CH_2$ | $OCH_3$ |
| 6-$SO_2CH_3$ | H | H | H | $CH_2$ | $OCH_3$ |
| 6-$CO_2CH_3$ | H | H | H | $CH_2$ | $OCH_3$ |
| 6-$SO_2N(CH_3)_2$ | H | H | H | $CH_2$ | $OCH_3$ |
| 6-$OSO_2CH_3$ | H | H | H | $CH_2$ | $OCH_3$ |
| H | H | 1-$CH_3$ | H | O | $CH_3$ |
| H | H | 1-$CH_3$ | H | O | $OCH_3$ |
| H | H | 1-$CH_3$ | H | $CH_2$ | $CH_3$ |
| H | H | 1-$CH_3$ | H | $CH_2$ | $OCH_3$ |
| H | H | 2-$CH_3$ | H | O | $CH_3$ |
| H | H | 2-$CH_3$ | H | O | $OCH_3$ |
| H | H | 2-$CH_3$ | H | $CH_2$ | $CH_3$ |
| H | H | 2-$CH_3$ | H | $CH_2$ | $OCH_3$ |
| H | H | 3-$CH_3$ | H | O | $CH_3$ |
| H | H | 3-$CH_3$ | H | O | $OCH_3$ |
| H | H | 3-$CH_3$ | H | $CH_2$ | $CH_3$ |
| H | H | 3-$CH_3$ | H | $CH_2$ | $OCH_3$ |
| H | H | H | $CH_3$ | O | $CH_3$ |

TABLE Ie-continued

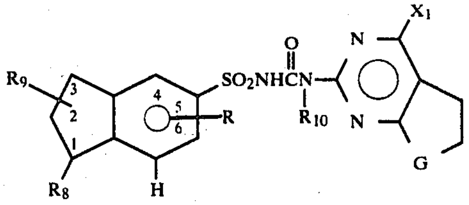

| R | $R_8$ | $R_9$ | $R_{10}$ | G | $X_1$ m.p.(°C.) |
|---|---|---|---|---|---|
| H | H | H | $CH_3$ | O | $OCH_3$ |
| H | H | H | $CH_3$ | $CH_2$ | $CH_3$ |
| H | H | H | $CH_3$ | $CH_2$ | $OCH_3$ |

TABLE If

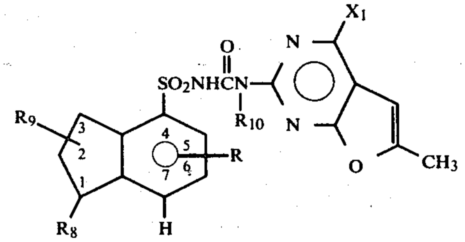

| R | $R_8$ | $R_9$ | $R_{10}$ | $X_1$ m.p.(°C.) |
|---|---|---|---|---|
| H | H | H | H | $CH_3$ |
| 5-Cl | H | H | H | $CH_3$ |
| 5-Br | H | H | H | $CH_3$ |
| 5-$NO_2$ | H | H | H | $CH_3$ |
| 5-$OCH_3$ | H | H | H | $CH_3$ |
| 5-$SCH_3$ | H | H | H | $CH_3$ |
| 5-$SO_2CH_3$ | H | H | H | $CH_3$ |
| 5-$CO_2CH_3$ | H | H | H | $CH_3$ |
| 5-$SO_2N(CH_3)_2$ | H | H | H | $CH_3$ |
| 5-$SO_2N(OCH_3)CH_3$ | H | H | H | $CH_3$ |
| 5-$OSO_2CH_3$ | H | H | H | $CH_3$ |
| 5-$CH_3$ | H | H | H | $CH_3$ |
| 6-Cl | H | H | H | $CH_3$ |
| 6-Br | H | H | H | $CH_3$ |
| 6-$NO_2$ | H | H | H | $CH_3$ |
| 6-$CH_3$ | H | H | H | $CH_3$ |
| 6-$OCH_3$ | H | H | H | $CH_3$ |
| H | H | H | H | $OCH_3$ |
| 5-Cl | H | H | H | $OCH_3$ |
| 5-Br | H | H | H | $OCH_3$ |
| 5-$NO_2$ | H | H | H | $OCH_3$ |
| 5-$OCH_3$ | H | H | H | $OCH_3$ |
| 5-$SCH_3$ | H | H | H | $OCH_3$ |
| 5-$SO_2CH_3$ | H | H | H | $OCH_3$ |
| 5-$CO_2CH_3$ | H | H | H | $OCH_3$ |
| 5-$SO_2N(CH_3)_2$ | H | H | H | $OCH_3$ |
| 5-$SO_2N(OCH_3)CH_3$ | H | H | H | $OCH_3$ |
| 5-$OSO_2CH_3$ | H | H | H | $OCH_3$ |
| 5-$CH_3$ | H | H | H | $OCH_3$ |
| 6-Cl | H | H | H | $OCH_3$ |
| 6-Br | H | H | H | $OCH_3$ |
| 6-$NO_2$ | H | H | H | $OCH_3$ |
| 6-$CH_3$ | H | H | H | $OCH_3$ |
| 6-$OCH_3$ | H | H | H | $OCH_3$ |
| H | H | 1-$CH_3$ | H | $CH_3$ |
| H | H | 2-$CH_3$ | H | $CH_3$ |
| H | H | 3-$CH_3$ | H | $CH_3$ |
| H | H | 1-$CH_3$ | H | $OCH_3$ |
| H | $CH_3$ | 2-$CH_3$ | H | $OCH_3$ |
| H | $CH_3$ | 3-$CH_3$ | H | $OCH_3$ |
| H | H | H | $CH_3$ | $CH_3$ |
| H | H | H | $CH_3$ | $OCH_3$ |

TABLE Ig

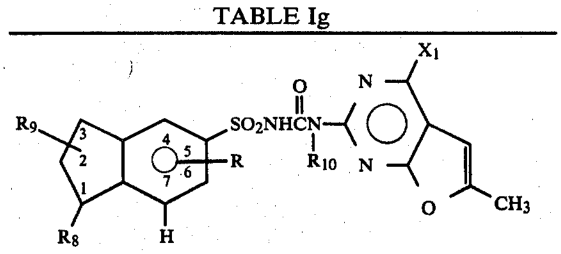

| R | $R_9$ | $R_{10}$ | $X_1$ m.p.(°C.) |
|---|---|---|---|
| H | H | H | $CH_3$ |
| 4-Cl | H | H | $CH_3$ |
| 4-Br | H | H | $CH_3$ |
| 4-$NO_2$ | H | H | $CH_3$ |
| 4-$OCH_3$ | H | H | $CH_3$ |
| 4-$SCH_3$ | H | H | $CH_3$ |
| 4-$SO_2CH_3$ | H | H | $CH_3$ |
| 4-$CO_2CH_3$ | H | H | $CH_3$ |
| 4-$SO_2N(CH_3)_2$ | H | H | $CH_3$ |
| 4-$SO_2N(OCH_3)CH_3$ | H | H | $CH_3$ |
| 4-$OSO_2CH_3$ | H | H | $CH_3$ |
| 6-Cl | H | H | $CH_3$ |
| 6-Br | H | H | $CH_3$ |
| 6-$NO_2$ | H | H | $CH_3$ |
| 6-$OCH_3$ | H | H | $CH_3$ |
| 6-$SCH_3$ | H | H | $CH_3$ |
| 6-$SO_2CH_3$ | H | H | $CH_3$ |
| 6-$CO_2CH_3$ | H | H | $CH_3$ |
| 6-$SO_2N(CH_3)_2$ | H | H | $CH_3$ |
| 6-$OSO_2CH_3$ | H | H | $CH_3$ |
| H | H | H | $OCH_3$ |
| 4-Cl | H | H | $OCH_3$ |
| 4-Br | H | H | $OCH_3$ |
| 4-$NO_2$ | H | H | $OCH_3$ |
| 4-$OCH_3$ | H | H | $OCH_3$ |
| 4-$SCH_3$ | H | H | $OCH_3$ |
| 4-$SO_2CH_3$ | H | H | $OCH_3$ |
| 4-$CO_2CH_3$ | H | H | $OCH_3$ |
| 4-$SO_2N(CH_3)_2$ | H | H | $OCH_3$ |
| 3-$OSO_2CH_3$ | H | H | $OCH_3$ |
| 6-Cl | H | H | $OCH_3$ |
| 6-Br | H | H | $OCH_3$ |
| 6-$NO_2$ | H | H | $OCH_3$ |
| 6-$OCH_3$ | H | H | $OCH_3$ |
| 6-$SCH_3$ | H | H | $OCH_3$ |
| 6-$SO_2CH_3$ | H | H | $OCH_3$ |
| 6-$CO_2CH_3$ | H | H | $OCH_3$ |
| 6-$SO_2N(CH_3)_2$ | H | H | $OCH_3$ |
| 6-$OSO_2CH_3$ | H | H | $OCH_3$ |
| H | 1-$CH_3$ | H | $CH_3$ |
| H | 1-$CH_3$ | H | $OCH_3$ |
| H | 2-$CH_3$ | H | $CH_3$ |
| H | 2-$CH_3$ | H | $OCH_3$ |
| H | 3-$CH_3$ | H | $CH_3$ |
| H | 3-$CH_3$ | H | $OCH_3$ |
| H | H | $CH_3$ | $CH_3$ |
| H | H | $CH_3$ | $OCH_3$ |

TABLE 1h

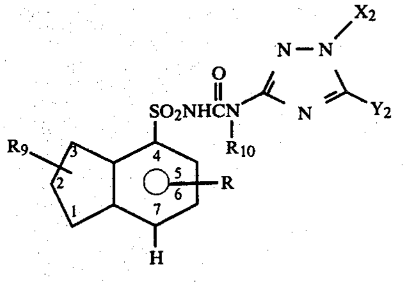

| $R_9$ | $R_{10}$ | $X_2$ | $Y_2$ |
|---|---|---|---|
| H | H | $CH_3$ | $SCH_3$ |
| H | H | $CH_3$ | $SC_2H_5$ |
| H | H | $CH_3$ | $OCH_3$ |

TABLE 1h-continued

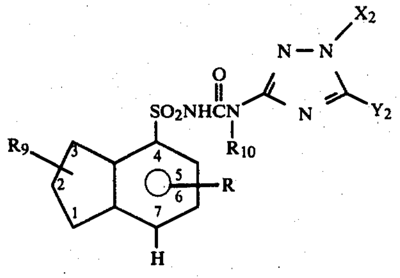

| R | $R_9$ | $R_{10}$ | $X_2$ | $Y_2$ |
|---|---|---|---|---|
| H | H | H | $CH_3$ | $OC_2H_5$ |
| H | H | H | $C_2H_5$ | $SCH_3$ |
| H | H | H | $C_2H_5$ | $SC_2H_5$ |
| H | H | H | $C_2H_5$ | $OCH_3$ |
| H | H | H | $C_2H_5$ | $OC_2H_5$ |
| H | H | H | n-$C_3H_7$ | $SCH_3$ |
| H | H | H | n-$C_3H_7$ | $SC_2H_5$ |
| H | H | H | n-$C_3H_7$ | $OCH_3$ |
| H | H | H | n-$C_3H_7$ | $OC_2H_5$ |
| H | H | H | $CH_2CF_3$ | $SCH_3$ |
| H | H | H | $CH_2CF_3$ | $SC_2H_5$ |
| H | H | H | $CH_2CF_3$ | $OCH_3$ |
| H | H | H | $CH_2CF_3$ | $OC_2H_5$ |
| 5-$CO_2CH_3$ | H | H | $CH_3$ | $OCH_3$ |
| 5-$SO_2N(CH_3)_2$ | H | H | $CH_3$ | $OCH_3$ |
| 5-$SCH_3$ | H | H | $CH_3$ | $OCH_3$ |
| 5-$SO_2CH_3$ | H | H | $CH_3$ | $OCH_3$ |
| 5-$OSO_2CH_3$ | H | H | $CH_3$ | $OCH_3$ |
| 5-$SO_2N(OCH_3)CH_3$ | H | H | $CH_3$ | $OCH_3$ |
| 5-$OCH_3$ | H | H | $CH_3$ | $OCH_3$ |
| 6-Cl | H | H | $CH_3$ | $OCH_3$ |
| 6-Br | H | H | $CH_3$ | $OCH_3$ |
| 6-$CH_3$ | H | H | $CH_3$ | $OCH_3$ |
| 6-$NO_2$ | H | H | $CH_3$ | $OCH_3$ |
| 6-$OCH_3$ | H | H | $CH_3$ | $OCH_3$ |
| H | 1-$CH_3$ | H | $CH_3$ | $OCH_3$ |
| H | 2-$CH_3$ | H | $C_2H_5$ | $SCH_3$ |
| H | 3-$CH_3$ | H | $CH_2CF_3$ | $OC_2H_5$ |
| H | H | $CH_3$ | $CH_3$ | $OCH_3$ |
| H | H | $CH_3$ | $CH_3$ | $SCH_3$ |

TABLE 1i

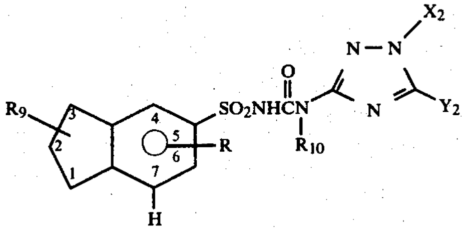

| R | $R_9$ | $R_{10}$ | $X_2$ | $Y_2$ |
|---|---|---|---|---|
| H | H | H | $CH_3$ | $SCH_3$ |
| H | H | H | $CH_3$ | $SC_2H_5$ |
| H | H | H | $CH_3$ | $OCH_3$ |
| H | H | H | $CH_3$ | $OC_2H_5$ |
| H | H | H | $C_2H_5$ | $SCH_3$ |
| H | H | H | $C_2H_5$ | $SC_2H_5$ |
| H | H | H | $C_2H_5$ | $OCH_3$ |
| H | H | H | $C_2H_5$ | $OC_2H_5$ |
| H | H | H | n-$C_3H_7$ | $OCH_3$ |
| H | H | H | $CH_2CF_3$ | $OCH_3$ |
| 4-$CO_2CH_3$ | H | H | $CH_3$ | $OCH_3$ |
| 4-$SO_2N(CH_3)_2$ | H | H | $CH_3$ | $OCH_3$ |
| 4-$OCH_3$ | H | H | $CH_3$ | $OCH_3$ |
| 4-$SO_2CH_3$ | H | H | $CH_3$ | $OCH_3$ |
| 6-$CO_2CH_3$ | H | H | $CH_3$ | $OCH_3$ |
| 6-$SO_2N(CH_3)_2$ | H | H | $CH_3$ | $OCH_3$ |
| 6-$OCH_3$ | H | H | $CH_3$ | $OCH_3$ |
| 6-$SO_2CH_3$ | H | H | $CH_3$ | $OCH_3$ |
| H | 1-$CH_3$ | H | $CH_3$ | $OCH_3$ |
| H | 2-$CH_3$ | H | $CH_3$ | $OCH_3$ |

TABLE 1i-continued

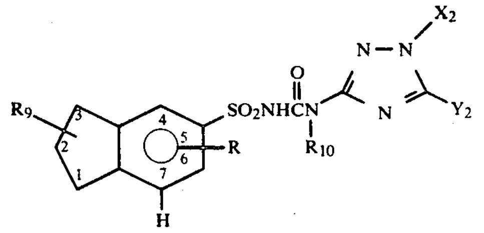

| R | $R_9$ | $R_{10}$ | $X_2$ | $Y_2$ |
|---|---|---|---|---|
| H | 3-$CH_3$ | H | $CH_3$ | $OCH_3$ |
| H | H | $CH_3$ | $CH_3$ | $OCH_3$ |

TABLE IIa

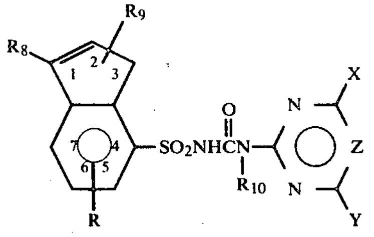

| $R_8$ | $R_9$ | R | $R_{10}$ | X | Y | Z | m.p. (°C.) |
|---|---|---|---|---|---|---|---|
| Cl | H | H | H | $CH_3$ | $CH_3$ | CH | 78-80° |
| Cl | H | H | H | $OCH_3$ | $CH_3$ | CH | 168-172° |
| Cl | H | H | H | $OCH_3$ | $OCH_3$ | CH | 88-91° |
| Cl | H | H | H | $CH_3$ | $C_2H_5$ | CH | |
| Cl | H | H | H | $OCH_3$ | $C_2H_5$ | CH | |
| Cl | H | H | H | $CH_3$ | $OC_2H_5$ | CH | |
| Cl | H | H | H | $OCH_3$ | $OC_2H_5$ | CH | |
| Cl | H | H | H | $CH_3$ | $CH_2OCH_3$ | CH | |
| Cl | H | H | H | $OCH_3$ | $CH_2OCH_3$ | CH | |
| Cl | H | H | H | $OCH_3$ | $NH_2$ | CH | |
| Cl | H | H | H | $OCH_3$ | $NHCH_3$ | CH | |
| Cl | H | H | H | $OCH_3$ | $N(CH_3)_2$ | CH | |
| Cl | H | H | H | $CH_3$ | $CH_3$ | N | |
| Cl | H | H | H | $OCH_3$ | $CH_3$ | N | 168-170° |
| Cl | H | H | H | $OCH_3$ | $OCH_3$ | N | |
| Cl | H | H | H | $CH_3$ | $C_2H_5$ | N | |
| Cl | H | H | H | $OCH_3$ | $C_2H_5$ | N | |
| Cl | H | H | H | $CH_3$ | $OC_2H_5$ | N | |
| Cl | H | H | H | $OCH_3$ | $OC_2H_5$ | N | |
| Cl | H | H | H | $CH_3$ | $CH_2OCH_3$ | N | |
| Cl | H | H | H | $OCH_3$ | $CH_2OCH_3$ | N | |
| Cl | H | H | H | $OCH_3$ | $NH_2$ | N | |
| Cl | H | H | H | $OCH_3$ | $NHCH_3$ | N | |
| Cl | H | H | H | $OCH_3$ | $N(CH_3)_2$ | N | |
| Cl | H | 5-Cl | H | $CH_3$ | $CH_3$ | CH | |
| Cl | H | 5-Cl | H | $CH_3$ | $OCH_3$ | CH | |
| Cl | H | 5-Cl | H | $OCH_3$ | $OCH_3$ | CH | |
| Cl | H | 5-$NO_2$ | H | $CH_3$ | $CH_3$ | CH | |
| Cl | H | 5-$NO_2$ | H | $CH_3$ | $OCH_3$ | CH | |
| Cl | H | 5-$NO_2$ | H | $OCH_3$ | $OCH_3$ | CH | |
| Cl | H | 5-$CO_2CH_3$ | H | $CH_3$ | $CH_3$ | CH | |
| Cl | H | 5-$CO_2CH_3$ | H | $CH_3$ | $OCH_3$ | CH | |
| Cl | H | 5-$CO_2CH_3$ | H | $OCH_3$ | $OCH_3$ | CH | |
| Cl | H | 5-$SO_2CH_3$ | H | $CH_3$ | $CH_3$ | CH | |
| Cl | H | 5-$SO_2CH_3$ | H | $CH_3$ | $OCH_3$ | CH | |
| Cl | H | 5-$SO_2CH_3$ | H | $OCH_3$ | $OCH_3$ | CH | |
| Cl | H | 5-$SO_2N(CH_3)_2$ | H | $CH_3$ | $CH_3$ | CH | |
| Cl | H | 5-$SO_2N(CH_3)_2$ | H | $CH_3$ | $OCH_3$ | CH | |
| Cl | H | 5-$SO_2N(CH_3)_2$ | H | $OCH_3$ | $OCH_3$ | CH | |
| Cl | H | 5-$OSO_2CF_3$ | H | $CH_3$ | $CH_3$ | CH | |
| Cl | H | 5-$OSO_2CF_3$ | H | $CH_3$ | $OCH_3$ | CH | |
| Cl | H | 5-$OSO_2CF_3$ | H | $OCH_3$ | $OCH_3$ | CH | |
| Cl | H | 5-$OCH_3$ | H | $CH_3$ | $CH_3$ | CH | |
| Cl | H | 5-$OCH_3$ | H | $CH_3$ | $OCH_3$ | CH | |
| Cl | H | 5-$OCH_3$ | H | $OCH_3$ | $OCH_3$ | CH | |
| Cl | H | 5-$OC_2H_5$ | H | $CH_3$ | $CH_3$ | CH | |
| Cl | H | 5-$OC_2H_5$ | H | $CH_3$ | $OCH_3$ | CH | |
| Cl | H | 5-$OC_2H_5$ | H | $OCH_3$ | $OCH_3$ | CH | |
| Cl | H | 5-Br | H | $CH_3$ | $CH_3$ | CH | |
| Cl | H | 5-Br | H | $CH_3$ | $OCH_3$ | CH | |
| Cl | H | 5-Br | H | $OCH_3$ | $OCH_3$ | CH | |
| Cl | H | 5-$OSO_2CH_3$ | H | $CH_3$ | $CH_3$ | CH | |
| Cl | H | 5-$OSO_2CH_3$ | H | $CH_3$ | $OCH_3$ | CH | |
| Cl | H | 5-$OSO_2CH_3$ | H | $OCH_3$ | $OCH_3$ | CH | |
| Cl | H | 5-Cl | H | $CH_3$ | $CH_3$ | N | |
| Cl | H | 5-Cl | H | $CH_3$ | $OCH_3$ | N | |
| Cl | H | 5-Cl | H | $OCH_3$ | $OCH_3$ | N | |
| Cl | H | 5-$NO_2$ | H | $CH_3$ | $CH_3$ | N | |
| Cl | H | 5-$NO_2$ | H | $CH_3$ | $OCH_3$ | N | |

TABLE IIa-continued

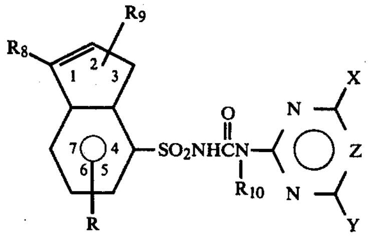

| $R_8$ | $R_9$ | R | $R_{10}$ | X | Y | Z | m.p. (°C.) |
|---|---|---|---|---|---|---|---|
| Cl | H | 5-$NO_2$ | H | $OCH_3$ | $OCH_3$ | N | |
| Cl | H | 5-$CO_2CH_3$ | H | $CH_3$ | $CH_3$ | N | |
| Cl | H | 5-$CO_2CH_3$ | H | $CH_3$ | $OCH_3$ | N | |
| Cl | H | 5-$CO_2CH_3$ | H | $OCH_3$ | $OCH_3$ | N | |
| Cl | H | 5-$SO_2CH_3$ | H | $CH_3$ | $CH_3$ | N | |
| Cl | H | 5-$SO_2CH_3$ | H | $CH_3$ | $OCH_3$ | N | |
| Cl | H | 5-$SO_2CH_3$ | H | $OCH_3$ | $OCH_3$ | N | |
| Cl | H | 5-$SO_2N(CH_3)_2$ | H | $CH_3$ | $CH_3$ | N | |
| Cl | H | 5-$SO_2N(CH_3)_2$ | H | $CH_3$ | $OCH_3$ | N | |
| Cl | H | 5-$SO_2N(CH_3)_2$ | H | $OCH_3$ | $OCH_3$ | N | |
| Cl | H | 5-$OSO_2CF_3$ | H | $CH_3$ | $CH_3$ | N | |
| Cl | H | 5-$OSO_2CF_3$ | H | $CH_3$ | $OCH_3$ | N | |
| Cl | H | 5-$OSO_2CF_3$ | H | $OCH_3$ | $OCH_3$ | N | |
| Cl | H | 6-Cl | H | $CH_3$ | $CH_3$ | CH | |
| Cl | H | 6-Cl | H | $CH_3$ | $OCH_3$ | CH | |
| Cl | H | 6-Cl | H | $OCH_3$ | $OCH_3$ | CH | |
| Cl | H | 6-$OCH_3$ | H | $CH_3$ | $CH_3$ | CH | |
| Cl | H | 6-$OCH_3$ | H | $CH_3$ | $OCH_3$ | CH | |
| Cl | H | 6-$OCH_3$ | H | $OCH_3$ | $OCH_3$ | CH | |
| Cl | H | 6-$NO_2$ | H | $CH_3$ | $CH_3$ | CH | |
| Cl | H | 6-$NO_2$ | H | $CH_3$ | $OCH_3$ | CH | |
| Cl | H | 6-$NO_2$ | H | $OCH_3$ | $OCH_3$ | CH | |
| Cl | H | 6-$SO_2CH_3$ | H | $CH_3$ | $CH_3$ | CH | |
| Cl | H | 6-$SO_2CH_3$ | H | $CH_3$ | $OCH_3$ | CH | |
| Cl | H | 6-$SO_2CH_3$ | H | $OCH_3$ | $OCH_3$ | CH | |
| Cl | H | 6-$CO_2CH_3$ | H | $CH_3$ | $CH_3$ | CH | |
| Cl | H | 6-$CO_2CH_3$ | H | $CH_3$ | $OCH_3$ | CH | |
| Cl | H | 6-$CO_2CH_3$ | H | $OCH_3$ | $OCH_3$ | CH | |
| Cl | H | 6-$SO_2N(CH_3)_2$ | H | $CH_3$ | $CH_3$ | CH | |
| Cl | H | 6-$SO_2N(CH_3)_2$ | H | $CH_3$ | $OCH_3$ | CH | |
| Cl | H | 6-$SO_2N(CH_3)_2$ | H | $OCH_3$ | $OCH_3$ | CH | |
| Cl | H | 6-Cl | H | $CH_3$ | $CH_3$ | N | |
| Cl | H | 6-Cl | H | $CH_3$ | $OCH_3$ | N | |
| Cl | H | 6-Cl | H | $OCH_3$ | $OCH_3$ | N | |
| Cl | H | 6-$OCH_3$ | H | $CH_3$ | $CH_3$ | N | |
| Cl | H | 6-$OCH_3$ | H | $CH_3$ | $OCH_3$ | N | |
| Cl | H | 6-$OCH_3$ | H | $OCH_3$ | $OCH_3$ | N | |
| Cl | H | 6-$NO_2$ | H | $CH_3$ | $CH_3$ | N | |
| Cl | H | 6-$NO_2$ | H | $CH_3$ | $OCH_3$ | N | |
| Cl | H | 6-$NO_2$ | H | $OCH_3$ | $OCH_3$ | N | |
| Cl | H | 6-$SO_2CH_3$ | H | $CH_3$ | $CH_3$ | N | |
| Cl | H | 6-$SO_2CH_3$ | H | $CH_3$ | $OCH_3$ | N | |
| Cl | H | 6-$SO_2CH_3$ | H | $OCH_3$ | $OCH_3$ | N | |
| Cl | H | 6-$CO_2CH_3$ | H | $CH_3$ | $CH_3$ | N | |
| Cl | H | 6-$CO_2CH_3$ | H | $CH_3$ | $OCH_3$ | N | |
| Cl | H | 6-$CO_2CH_3$ | H | $OCH_3$ | $OCH_3$ | N | |
| Cl | H | 6-$SO_2N(CH_3)_2$ | H | $CH_3$ | $CH_3$ | N | |
| Cl | H | 6-$SO_2N(CH_3)_2$ | H | $CH_3$ | $OCH_3$ | N | |
| Cl | H | 6-$SO_2N(CH_3)_2$ | H | $OCH_3$ | $OCH_3$ | N | |
| $CH_3$ | H | H | H | $CH_3$ | $CH_3$ | CH | |
| $CH_3$ | H | H | H | $CH_3$ | $OCH_3$ | CH | |
| $CH_3$ | H | H | H | $OCH_3$ | $OCH_3$ | CH | |
| $CH_3$ | H | 5-Cl | H | $CH_3$ | $CH_3$ | CH | |
| $CH_3$ | H | 5-Cl | H | $CH_3$ | $OCH_3$ | CH | |
| $CH_3$ | H | 5-Cl | H | $OCH_3$ | $OCH_3$ | CH | |
| $CH_3$ | H | 5-Br | H | $CH_3$ | $CH_3$ | CH | |
| $CH_3$ | H | 5-Br | H | $CH_3$ | $OCH_3$ | CH | |
| $CH_3$ | H | 5-Br | H | $OCH_3$ | $OCH_3$ | CH | |
| $CH_3$ | H | 5-$NO_2$ | H | $CH_3$ | $CH_3$ | CH | |
| $CH_3$ | H | 5-$NO_2$ | H | $CH_3$ | $OCH_3$ | CH | |
| $CH_3$ | H | 5-$NO_2$ | H | $OCH_3$ | $OCH_3$ | CH | |
| $CH_3$ | H | 5-$SO_2CH_3$ | H | $CH_3$ | $CH_3$ | CH | |
| $CH_3$ | H | 5-$SO_2CH_3$ | H | $CH_3$ | $OCH_3$ | CH | |
| $CH_3$ | H | 5-$SO_2CH_3$ | H | $OCH_3$ | $OCH_3$ | CH | |
| H | H | 5-$CH_3$ | H | $CH_3$ | $CH_3$ | CH | |
| H | H | 5-$CH_3$ | H | $CH_3$ | $OCH_3$ | CH | |
| H | H | 5-$CH_3$ | H | $OCH_3$ | $OCH_3$ | CH | |
| H | H | 5-Cl | H | $CH_3$ | $CH_3$ | CH | |
| H | H | 5-Cl | H | $CH_3$ | $OCH_3$ | CH | |

TABLE IIa-continued

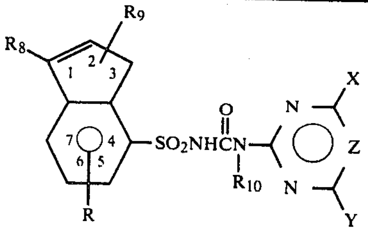

| R8 | R9 | R | R10 | X | Y | Z | m.p. (°C.) |
|---|---|---|---|---|---|---|---|
| H | H | 5-Cl | H | $OCH_3$ | $OCH_3$ | CH | |
| H | H | 6-$CH_3$ | H | $CH_3$ | $CH_3$ | CH | |
| H | H | 6-$CH_3$ | H | $CH_3$ | $OCH_3$ | CH | |
| H | H | 6-$CH_3$ | H | $OCH_3$ | $OCH_3$ | CH | |
| H | H | 5-$NO_2$ | H | $CH_3$ | $CH_3$ | CH | |
| H | H | 5-$NO_2$ | H | $CH_3$ | $OCH_3$ | CH | |
| H | H | 5-$NO_2$ | H | $OCH_3$ | $OCH_3$ | CH | |
| H | H | 5-$CO_2CH_3$ | H | $CH_3$ | $CH_3$ | CH | |
| H | H | 5-$CO_2CH_3$ | H | $CH_3$ | $OCH_3$ | CH | |
| H | H | 5-$CO_2CH_3$ | H | $OCH_3$ | $OCH_3$ | CH | |
| H | H | 5-$OC_2H_5$ | H | $CH_3$ | $OCH_3$ | CH | |
| H | H | 6-O—n-$C_3H_7$ | H | $OCH_3$ | $OCH_3$ | N | |
| H | H | 5-$OCF_2H$ | H | $CH_3$ | $CH_3$ | CH | |
| H | H | 6-$OCF_3$ | H | $OCH_3$ | $OCH_3$ | CH | |
| H | H | 5-$OCF_2CF_2H$ | H | $CH_3$ | $OCH_3$ | N | |
| H | H | 5-$SO_2N(CH_3)C_2H_5$ | H | $OCH_3$ | $OCH_3$ | N | |
| H | H | 6-$SO_2N(C_2H_5)_2$ | H | $CH_3$ | $CH_3$ | CH | |
| H | H | 6-$SO_2N(OCH_3)CH_3$ | H | $CH_3$ | $OCH_3$ | CH | |
| H | H | 5-$CO_2C_2H_5$ | H | $CH_3$ | $OCH_3$ | CH | |
| H | H | 6-$CO_2$—n-$C_3H_7$ | H | $OCH_3$ | $OCH_3$ | N | |
| H | H | 5-$CO_2CH_2CH{=}CH_2$ | H | $CH_3$ | $CH_3$ | CH | |
| H | H | 6-$CO_2CH_2CH_2OCH_3$ | H | $OCH_3$ | $OCH_3$ | N | |
| H | H | 5-$CO_2CH_2CH_2CH_2Cl$ | H | $OCH_3$ | $CH_3$ | CH | |
| H | H | 5-$OSO_2C_2H_5$ | H | $OCH_3$ | $OCH_3$ | N | |
| H | H | 5-$OSO_2$—n-$C_3H_7$ | H | $CH_3$ | $OCH_3$ | N | |
| H | H | 5-$C_2H_5$ | H | $CH_3$ | $CH_3$ | N | |
| H | H | 6-n-$C_3H_7$ | H | $CH_3$ | $OCH_3$ | N | |
| Cl | H | H | H | Cl | $OCH_3$ | CH | |
| Cl | H | H | H | Cl | $NH_2$ | CH | |
| Cl | H | H | H | Cl | $NCH_3$ | CH | |
| Cl | H | H | H | Cl | $N(CH_3)_2$ | CH | |
| Cl | H | H | H | $OCH_3$ | $SCH_3$ | CH | |
| Cl | H | H | H | $CH_3$ | $CH(OCH_3)_2$ | N | |
| Cl | H | H | H | $CH_3$ | 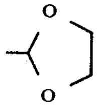 | CH | |
| H | 1-$CH_3$ | H | H | $CH_3$ | $OCH_3$ | CH | |
| H | 2-$CH_3$ | H | H | $OCH_3$ | $OCH_3$ | N | |
| H | 3-$CH_3$ | H | H | $CH_3$ | $OCH_3$ | N | |
| H | H | H | $CH_3$ | $OCH_3$ | $OCH_3$ | N | |

TABLE IIb

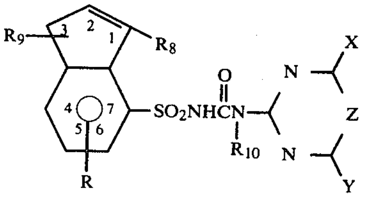

| R8 | R9 | R | R10 | X | Y | Z | m.p. (°C.) |
|---|---|---|---|---|---|---|---|
| Cl | H | H | H | $CH_3$ | $CH_3$ | CH | |
| Cl | H | H | H | $OCH_3$ | $CH_3$ | CH | |
| Cl | H | H | H | $OCH_3$ | $OCH_3$ | CH | |
| Cl | H | H | H | $CH_3$ | $C_2H_5$ | CH | |
| Cl | H | H | H | $OCH_3$ | $C_2H_5$ | CH | |
| Cl | H | H | H | $CH_3$ | $OC_2H_5$ | CH | |
| Cl | H | H | H | $OCH_3$ | $OC_2H_5$ | CH | |
| Cl | H | H | H | $CH_3$ | $CH_2OCH_3$ | CH | |

TABLE IIb-continued

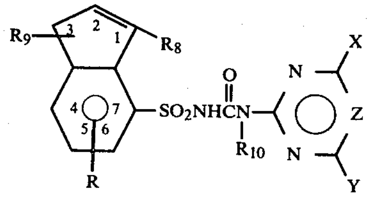

| R8 | R9 | R | R10 | X | Y | Z | m.p. (°C.) |
|---|---|---|---|---|---|---|---|
| Cl | H | H | H | $OCH_3$ | $CH_2OCH_3$ | CH | |
| Cl | H | H | H | $OCH_3$ | $NH_2$ | CH | |
| Cl | H | H | H | $OCH_3$ | $NHCH_3$ | CH | |
| Cl | H | H | H | $OCH_3$ | $N(CH_3)_2$ | CH | |
| Cl | H | H | H | $CH_3$ | $CH_3$ | N | |
| Cl | H | H | H | $OCH_3$ | $CH_3$ | N | |
| Cl | H | H | H | $OCH_3$ | $OCH_3$ | N | |
| Cl | H | H | H | $CH_3$ | $C_2H_5$ | N | |

TABLE IIb-continued

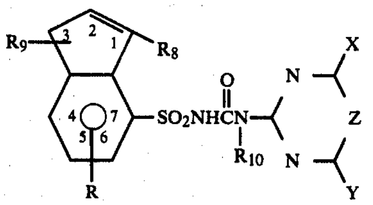

| R8 | R9 | R | R10 | X | Y | Z | m.p. (°C.) |
|---|---|---|---|---|---|---|---|
| Cl | H | H | H | $OCH_3$ | $C_2H_5$ | N | |
| Cl | H | H | H | $CH_3$ | $OC_2H_5$ | N | |
| Cl | H | H | H | $OCH_3$ | $OC_2H_5$ | N | |
| Cl | H | H | H | $CH_3$ | $CH_2OCH_3$ | N | |
| Cl | H | H | H | $OCH_3$ | $CH_2OCH_3$ | N | |
| Cl | H | H | H | $OCH_3$ | $NH_2$ | N | |
| Cl | H | H | H | $OCH_3$ | $NHCH_3$ | N | |
| Cl | H | H | H | $OCH_3$ | $N(CH_3)_2$ | N | |
| Cl | H | H | H | Cl | $OCH_3$ | CH | |
| H | 2-$CH_3$ | H | H | $OCH_3$ | $OCH_3$ | CH | |
| H | H | H | $CH_3$ | $OCH_3$ | $OCH_3$ | N | |
| $CH_3$ | H | H | H | $CH_3$ | $OCH_3$ | CH | |

TABLE IIc

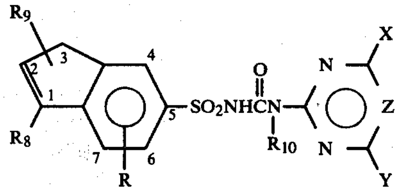

| R8 | R9 | R | R10 | X | Y | Z | m.p. (°C.) |
|---|---|---|---|---|---|---|---|
| Cl | H | H | H | $CH_3$ | $CH_3$ | CH | |
| Cl | H | H | H | $OCH_3$ | $CH_3$ | CH | |
| Cl | H | H | H | $OCH_3$ | $OCH_3$ | CH | |
| Cl | H | H | H | $CH_3$ | $C_2H_5$ | CH | |
| Cl | H | H | H | $OCH_3$ | $C_2H_5$ | CH | |
| Cl | H | H | H | $CH_3$ | $OC_2H_5$ | CH | |
| Cl | H | H | H | $OCH_3$ | $OC_2H_5$ | CH | |
| Cl | H | H | H | $CH_3$ | $CH_2OCH_3$ | CH | |
| Cl | H | H | H | $OCH_3$ | $CH_2OCH_3$ | CH | |
| Cl | H | H | H | $OCH_3$ | $NH_2$ | CH | |
| Cl | H | H | H | $OCH_3$ | $NHCH_3$ | CH | |
| Cl | H | H | H | $OCH_3$ | $N(CH_3)_2$ | CH | |
| Cl | H | H | H | $CH_3$ | $CH_3$ | N | |
| Cl | H | H | H | $OCH_3$ | $CH_3$ | N | |
| Cl | H | H | H | $OCH_3$ | $OCH_3$ | N | |
| Cl | H | H | H | $CH_3$ | $C_2H_5$ | N | |
| Cl | H | H | H | $OCH_3$ | $C_2H_5$ | N | |
| Cl | H | H | H | $CH_3$ | $OC_2H_5$ | N | |
| Cl | H | H | H | $OCH_3$ | $OC_2H_5$ | N | |
| Cl | H | H | H | $CH_3$ | $CH_2OCH_3$ | N | |
| Cl | H | H | H | $OCH_3$ | $CH_2OCH_3$ | N | |
| Cl | H | H | H | $OCH_3$ | $NH_2$ | N | |
| Cl | H | H | H | $OCH_3$ | $NHCH_3$ | N | |
| Cl | H | H | H | $OCH_3$ | $N(CH_3)_2$ | N | |
| Cl | H | H | H | Cl | $OCH_3$ | CH | |
| H | H | H | H | $OCH_3$ | $CH_3$ | N | |
| H | H | H | $CH_3$ | $OCH_3$ | $OCH_3$ | N | |
| H | 3-$CH_3$ | H | H | $CH_3$ | $OCH_3$ | CH | |
| H | H | H | H | $CH_3$ | 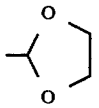 | CH | |

TABLE IId

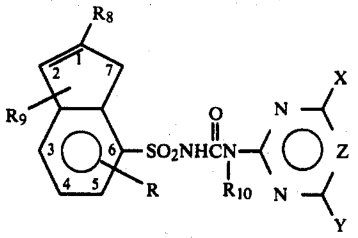

| R8 | R9 | R | R10 | X | Y | Z | m.p.(°C.) |
|---|---|---|---|---|---|---|---|
| Cl | H | H | H | $CH_3$ | $CH_3$ | CH | |
| Cl | H | H | H | $OCH_3$ | $CH_3$ | CH | |
| Cl | H | H | H | $OCH_3$ | $OCH_3$ | CH | |
| Cl | H | H | H | $CH_3$ | $C_2H_5$ | CH | |
| Cl | H | H | H | $OCH_3$ | $C_2H_5$ | CH | |
| Cl | H | H | H | $CH_3$ | $OC_2H_5$ | CH | |
| Cl | H | H | H | $OCH_3$ | $OC_2H_5$ | CH | |
| Cl | H | H | H | $CH_3$ | $CH_2OCH_3$ | CH | |
| Cl | H | H | H | $OCH_3$ | $CH_2OCH_3$ | CH | |
| Cl | H | H | H | $OCH_3$ | $NH_2$ | CH | |
| Cl | H | H | H | $OCH_3$ | $NHCH_3$ | CH | |
| Cl | H | H | H | $OCH_3$ | $N(CH_3)_2$ | CH | |
| Cl | H | H | H | $CH_3$ | $CH_3$ | N | |
| Cl | H | H | H | $OCH_3$ | $CH_3$ | N | |
| Cl | H | H | H | $OCH_3$ | $OCH_3$ | N | |
| Cl | H | H | H | $CH_3$ | $C_2H_5$ | N | |
| Cl | H | H | H | $OCH_3$ | $C_2H_5$ | N | |
| Cl | H | H | H | $CH_3$ | $OC_2H_5$ | N | |
| Cl | H | H | H | $OCH_3$ | $OC_2H_5$ | N | |
| Cl | H | H | H | $CH_3$ | $CH_2OCH_3$ | N | |
| Cl | H | H | H | $OCH_3$ | $CH_2OCH_3$ | N | |
| Cl | H | H | H | $OCH_3$ | $NH_2$ | N | |
| Cl | H | H | H | $OCH_3$ | $NHCH_3$ | N | |
| Cl | H | H | H | $OCH_3$ | $N(CH_3)_2$ | N | |
| H | H | H | H | Cl | $OCH_3$ | CH | |
| H | H | H | H | $OCH_3$ | $CH_3$ | N | |
| H | H | H | $CH_3$ | $OCH_3$ | $OCH_3$ | CH | |
| H | H | 7-$CH_3$ | H | $CH_3$ | $OCH_3$ | CH | |
| H | H | H | H | $CH_3$ | 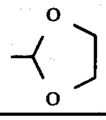 | CH | |

TABLE IIe

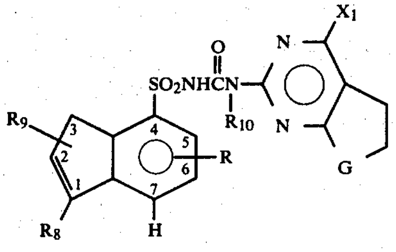

| R | R8 | R9 | R10 | G | X1 | m.p.(°C.) |
|---|---|---|---|---|---|---|
| H | Cl | H | H | O | $CH_3$ | |
| H | Cl | H | H | O | $OCH_3$ | |
| H | Cl | H | H | $CH_2$ | $CH_3$ | |
| H | Cl | H | H | $CH_2$ | $OCH_3$ | |
| H | H | H | H | O | $OCH_3$ | |
| H | H | H | H | O | $CH_3$ | |
| H | H | H | H | $CH_2$ | $OCH_3$ | |
| H | H | H | H | $CH_2$ | $CH_3$ | |
| 6-$NO_2$ | H | H | H | O | $OCH_3$ | |
| 5-Cl | H | H | H | O | $CH_3$ | |
| H | $CH_3$ | H | H | $CH_2$ | $OCH_3$ | |
| H | H | 2-$CH_3$ | H | O | $OCH_3$ | |
| H | H | H | $CH_3$ | O | $CH_3$ | |

TABLE IIf

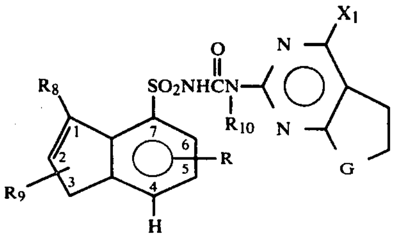

| R | R8 | R9 | R10 | G | X1 | m.p.(°C.) |
|---|---|---|---|---|---|---|
| H | Cl | H | H | O | $CH_3$ | |
| H | Cl | H | H | O | $OCH_3$ | |
| H | Cl | H | H | $CH_2$ | $CH_3$ | |
| H | Cl | H | H | $CH_2$ | $OCH_3$ | |
| H | H | H | H | O | $OCH_3$ | |
| H | H | H | H | O | $CH_3$ | |
| H | H | H | H | $CH_2$ | $OCH_3$ | |
| H | H | H | H | $CH_2$ | $CH_3$ | |
| 6-$CH_3$ | H | H | H | O | $CH_3$ | |
| H | $CH_3$ | H | H | $CH_2$ | $OCH_3$ | |
| H | H | 3-$CH_3$ | H | O | $CH_3$ | |
| H | H | H | $CH_3$ | O | $CH_3$ | |

TABLE IIg

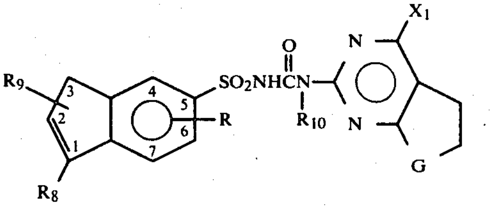

| R | R8 | R9 | R10 | G | X1 | m.p.(°C.) |
|---|---|---|---|---|---|---|
| H | Cl | H | H | O | $CH_3$ | |
| H | Cl | H | H | O | $OCH_3$ | |
| H | Cl | H | H | $CH_2$ | $CH_3$ | |
| H | Cl | H | H | $CH_2$ | $OCH_3$ | |
| H | H | H | H | O | $OCH_3$ | |
| H | H | H | H | O | $CH_3$ | |
| H | H | H | H | $CH_2$ | $OCH_3$ | |
| H | H | H | H | $CH_2$ | $CH_3$ | |
| 6-$CH_3$ | H | H | H | O | $CH_3$ | |
| H | $CH_3$ | H | H | $CH_2$ | $OCH_3$ | |
| H | H | 3-$CH_3$ | H | O | $OCH_3$ | |
| H | H | H | $CH_3$ | O | $CH_3$ | |

TABLE IIh

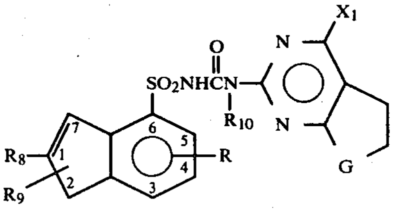

| R | R8 | R9 | R10 | G | X1 | m.p.(°C.) |
|---|---|---|---|---|---|---|
| H | Cl | H | H | O | $CH_3$ | |
| H | Cl | H | H | O | $OCH_3$ | |
| H | Cl | H | H | $CH_2$ | $CH_3$ | |
| H | Cl | H | H | $CH_2$ | $OCH_3$ | |
| H | H | H | H | O | $OCH_3$ | |
| H | H | H | H | O | $CH_3$ | |
| H | H | H | H | $CH_2$ | $OCH_3$ | |
| H | H | H | H | $CH_2$ | $CH_3$ | |
| 5-$CH_3$ | H | H | H | O | $CH_3$ | |
| H | $CH_3$ | H | H | $CH_2$ | $OCH_3$ | |
| H | H | 2-$CH_3$ | H | O | $CH_3$ | |

TABLE IIh-continued

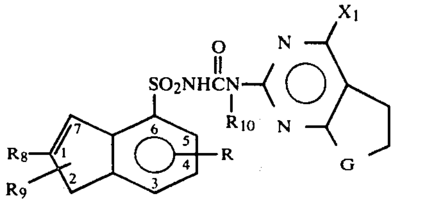

| R | R8 | R9 | R10 | G | X1 | m.p.(°C.) |
|---|---|---|---|---|---|---|
| H | H | H | $CH_3$ | O | $OCH_3$ | |

TABLE IIi

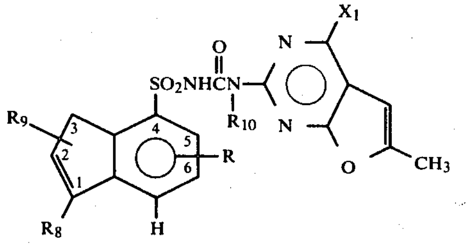

| R | R8 | R9 | R10 | X1 | m.p.(°C.) |
|---|---|---|---|---|---|
| H | Cl | H | H | $CH_3$ | |
| H | Cl | H | H | $OCH_3$ | |
| H | H | H | H | $CH_3$ | |
| H | H | H | H | $OCH_3$ | |
| H | $CH_3$ | H | H | $CH_3$ | |
| H | $CH_3$ | H | H | $OCH_3$ | |
| 5-$CH_3$ | H | H | H | $CH_3$ | |
| H | H | 2-$CH_3$ | H | $OCH_3$ | |
| H | Cl | H | $CH_3$ | $OCH_3$ | |

TABLE IIj

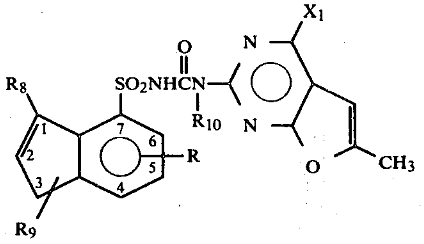

| R | R8 | R9 | R10 | X1 | m.p.(°C.) |
|---|---|---|---|---|---|
| H | Cl | H | H | $CH_3$ | |
| H | Cl | H | H | $OCH_3$ | |
| H | H | H | H | $CH_3$ | |
| H | H | H | H | $OCH_3$ | |
| H | $CH_3$ | H | H | $CH_3$ | |
| H | $CH_3$ | H | H | $OCH_3$ | |
| 6-$CH_3$ | H | H | H | $CH_3$ | |
| H | H | 2-$CH_3$ | H | $OCH_3$ | |
| H | Cl | H | $CH_3$ | $OCH_3$ | |

TABLE IIk

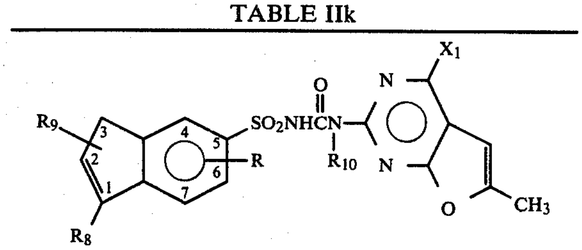

| R | $R_8$ | $R_9$ | $R_{10}$ | $X_1$ | m.p.(°C.) |
|---|---|---|---|---|---|
| H | Cl | H | H | $CH_3$ | |
| H | Cl | H | H | $OCH_3$ | |
| H | H | H | H | $CH_3$ | |
| H | H | H | H | $OCH_3$ | |
| H | $CH_3$ | H | H | $CH_3$ | |
| H | $CH_3$ | H | H | $OCH_3$ | |
| 6-$CH_3$ | H | H | H | $CH_3$ | |
| H | H | 2-$CH_3$ | H | $OCH_3$ | |
| H | Cl | H | $CH_3$ | $OCH_3$ | |

TABLE III

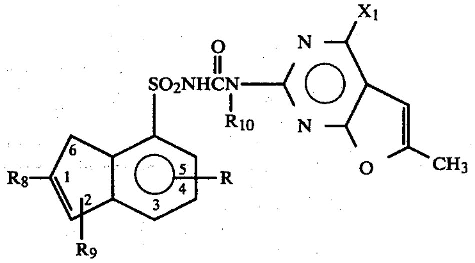

| R | $R_8$ | $R_9$ | $R_{10}$ | $X_1$ | m.p. (°C.) |
|---|---|---|---|---|---|
| H | Cl | H | H | $CH_3$ | |
| H | Cl | H | H | $OCH_3$ | |
| H | H | H | H | $CH_3$ | |
| H | H | H | H | $OCH_3$ | |
| H | $CH_3$ | H | H | $CH_3$ | |
| H | $CH_3$ | H | H | $OCH_3$ | |
| 5-$CH_3$ | H | H | H | $CH_3$ | |
| H | H | 2-$CH_3$ | H | $OCH_3$ | |
| H | Cl | H | $CH_3$ | $OCH_3$ | |

TABLE IIm

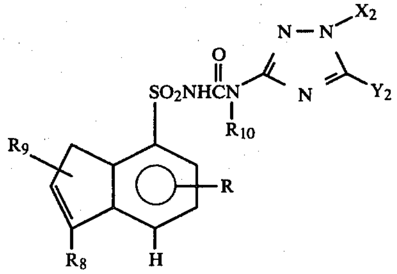

| R | $R_8$ | | $R_{10}$ | $X_2$ | $Y_2$ | m.p. (°C.) |
|---|---|---|---|---|---|---|
| H | Cl | H | H | $CH_3$ | $SCH_3$ | |
| H | Cl | H | H | $CH_3$ | $OCH_3$ | |
| H | Cl | H | H | $CH_3$ | $OC_2H_5$ | |
| H | Cl | H | H | $CH_3$ | $SC_2H_5$ | |
| H | Cl | H | H | $C_2H_5$ | $OCH_3$ | |
| H | Cl | H | H | n-$C_3H_7$ | $OCH_3$ | |
| H | Cl | H | H | $CH_2CF_3$ | $OCH_3$ | |
| H | H | H | H | $CH_3$ | $SCH_3$ | |
| H | H | H | H | $CH_3$ | $OCH_3$ | |
| H | H | H | H | $CH_3$ | $OC_2H_5$ | |
| H | H | H | H | $CH_3$ | $SC_2H_5$ | |
| H | $CH_3$ | H | H | $CH_3$ | $OCH_3$ | |
| $CH_3$ | H | H | H | $CH_3$ | $SCH_3$ | |

TABLE IIm-continued

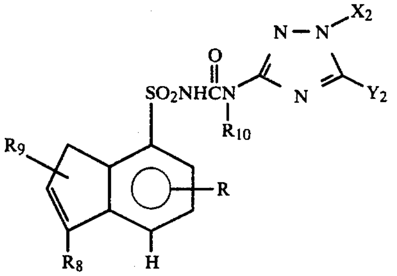

| R | | $R_8$ | $R_{10}$ | $X_2$ | $Y_2$ | m.p. (°C.) |
|---|---|---|---|---|---|---|
| H | H | 2-$CH_3$ | H | $CH_3$ | $OCH_3$ | |
| H | H | H | $CH_3$ | $CH_3$ | $OCH_3$ | |

TABLE IIn

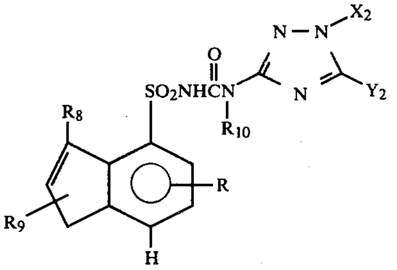

| R | $R_8$ | $R_9$ | $R_{10}$ | $X_2$ | $Y_2$ | m.p. (°C.) |
|---|---|---|---|---|---|---|
| H | Cl | H | H | $CH_3$ | $SCH_2$ | |
| H | Cl | H | H | $CH_3$ | $OCH_3$ | |
| H | Cl | H | H | $CH_3$ | $OC_2H_5$ | |
| H | Cl | H | H | $CH_3$ | $SC_2H_5$ | |
| H | Cl | H | H | $C_2H_5$ | $OCH_3$ | |
| H | Cl | H | H | n-$C_3H_7$ | $OCH_3$ | |
| H | Cl | H | H | $CH_2CF_3$ | $OCH_3$ | |
| H | H | H | H | $CH_3$ | $SCH_3$ | |
| H | H | H | H | $CH_3$ | $OCH_3$ | |
| H | H | H | H | $CH_3$ | $OC_2H_5$ | |
| H | H | H | H | $CH_3$ | $SC_2H_5$ | |
| H | $CH_3$ | H | H | $CH_3$ | $OCH_3$ | |
| $CH_3$ | H | H | H | $CH_3$ | $SCH_3$ | |
| H | H | 2-$CH_3$ | H | $CH_3$ | $OCH_3$ | |
| H | H | H | $CH_3$ | $CH_3$ | $OCH_3$ | |

TABLE IIo

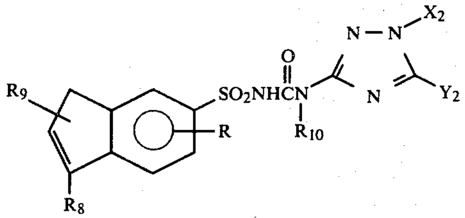

| R | $R_8$ | $R_9$ | $R_{10}$ | $X_2$ | $Y_2$ | m.p. (°C.) |
|---|---|---|---|---|---|---|
| H | Cl | H | H | $CH_3$ | $SCH_3$ | |
| H | Cl | H | H | $CH_3$ | $OCH_3$ | |
| H | Cl | H | H | $CH_3$ | $OC_2H_5$ | |
| H | Cl | H | H | $CH_3$ | $SC_2H_5$ | |
| H | Cl | H | H | $C_2H_5$ | $OCH_3$ | |
| H | Cl | H | H | n-$C_3H_7$ | $OCH_3$ | |
| H | Cl | H | H | $CH_2CF_3$ | $OCH_3$ | |
| H | H | H | H | $CH_3$ | $SCH_3$ | |
| H | H | H | H | $CH_3$ | $OCH_3$ | |
| H | H | H | H | $CH_3$ | $OC_2H_5$ | |
| H | H | H | H | $CH_3$ | $SC_2H_5$ | |
| H | $CH_3$ | H | H | $CH_3$ | $OCH_3$ | |
| $CH_3$ | H | H | H | $CH_3$ | $SCH_3$ | |
| H | H | 2-$CH_3$ | H | $CH_3$ | $OCH_3$ | |

TABLE IIo-continued

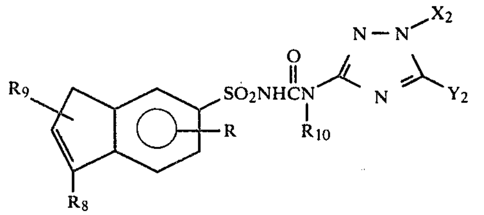

| R | $R_8$ | $R_9$ | $R_{10}$ | $X_2$ | $Y_2$ | m.p. (°C.) |
|---|---|---|---|---|---|---|
| H | H | H | $CH_3$ | $CH_3$ | $OCH_3$ | |

TABLE IIp

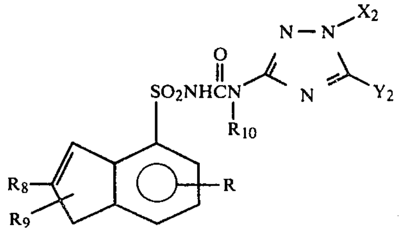

| R | $R_8$ | $R_9$ | $R_{10}$ | $X_2$ | $Y_2$ | m.p. (°C.) |
|---|---|---|---|---|---|---|
| H | Cl | H | H | $CH_3$ | $SCH_3$ | |
| H | Cl | H | H | $CH_3$ | $OCH_3$ | |
| H | Cl | H | H | $CH_3$ | $OC_2H_5$ | |
| H | Cl | H | H | $CH_3$ | $SC_2H_5$ | |
| H | Cl | H | H | $C_2H_5$ | $OCH_3$ | |
| H | Cl | H | H | n-$C_3H_7$ | $OCH_3$ | |
| H | Cl | H | H | $CH_2CF_3$ | $OCH_3$ | |
| H | H | H | H | $CH_3$ | $SCH_3$ | |
| H | H | H | H | $CH_3$ | $OCH_3$ | |
| H | H | H | H | $CH_3$ | $OC_2H_5$ | |
| H | H | H | H | $CH_3$ | $SC_2H_5$ | |
| H | $CH_3$ | H | H | $CH_3$ | $OCH_3$ | |
| $CH_3$ | H | H | H | $CH_3$ | $SCH_3$ | |
| H | H | 2-$CH_3$ | H | $CH_3$ | $OCH_3$ | |
| H | H | H | $CH_3$ | $CH_3$ | $OCH_3$ | |

TABLE IIIa

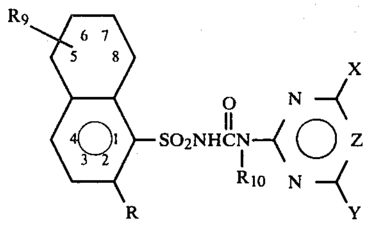

| $R_9$ | R | $R_{10}$ | X | Y | Z | m.p. (°C.) |
|---|---|---|---|---|---|---|
| H | H | H | $CH_3$ | $CH_3$ | CH | 152–155° |
| H | H | H | $OCH_3$ | $CH_3$ | CH | 155–157° |
| H | H | H | $OCH_3$ | $OCH_3$ | CH | 145–147° |
| H | H | H | $CH_3$ | $C_2H_5$ | CH | |
| H | H | H | $OCH_3$ | $C_2H_5$ | CH | |
| H | H | H | $CH_3$ | $OC_2H_5$ | CH | |
| H | H | H | $OCH_3$ | $OC_2H_5$ | CH | |
| H | H | H | $CH_3$ | $CH_2OCH_3$ | CH | |
| H | H | H | $OCH_3$ | $CH_2OCH_3$ | CH | |
| H | H | H | $OCH_3$ | $NH_2$ | CH | |
| H | H | H | $OCH_3$ | $NHCH_3$ | CH | |
| H | H | H | $OCH_3$ | $N(CH_3)_2$ | CH | |
| H | H | H | $CH_3$ | $CH_3$ | N | 150–152° |
| H | H | H | $OCH_3$ | $CH_3$ | N | |
| H | H | H | $OCH_3$ | $OCH_3$ | N | 171–173° |
| H | H | H | $CH_3$ | $C_2H_5$ | N | |
| H | H | H | $OCH_3$ | $C_2H_5$ | N | |
| H | H | H | $CH_3$ | $OC_2H_5$ | N | |
| H | H | H | $OCH_3$ | $OC_2H_5$ | N | |
| H | H | H | $CH_3$ | $CH_2OCH_3$ | N | |
| H | H | H | $OCH_3$ | $CH_2OCH_3$ | N | |
| H | H | H | $OCH_3$ | $NH_2$ | N | |
| H | H | H | $OCH_3$ | $NHCH_3$ | N | |
| H | H | H | $OCH_3$ | $N(CH_3)_2$ | N | |
| H | H | H | Cl | $OCH_3$ | CH | |
| H | H | H | $OCH_3$ | $SCH_3$ | N | |
| H | H | H | $CH_3$ | $CH(OCH_3)_2$ | CH | |
| H | H | H | $CH_3$ | 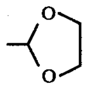 | CH | |
| H | Cl | H | $CH_3$ | $CH_3$ | CH | |
| H | Cl | H | $OCH_3$ | $CH_3$ | CH | |
| H | Cl | H | $OCH_3$ | $OCH_3$ | CH | |

TABLE IIIa-continued

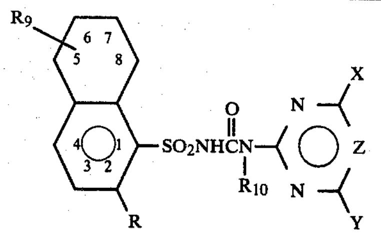

| R9 | R | R10 | X | Y | Z | m.p. (°C.) |
|---|---|---|---|---|---|---|
| H | Cl | H | $CH_3$ | $C_2H_5$ | CH | |
| H | Cl | H | $OCH_3$ | $C_2H_5$ | CH | |
| H | Cl | H | $CH_3$ | $OC_2H_5$ | CH | |
| H | Cl | H | $OCH_3$ | $OC_2H_5$ | CH | |
| H | Cl | H | $CH_3$ | $CH_2OCH_3$ | CH | |
| H | Cl | H | $OCH_3$ | $CH_2OCH_3$ | CH | |
| H | Cl | H | $OCH_3$ | $NH_2$ | CH | |
| H | Cl | H | $OCH_3$ | $NHCH_3$ | CH | |
| H | Cl | H | $OCH_3$ | $N(CH_3)_2$ | CH | |
| H | Cl | H | $CH_3$ | $CH_3$ | N | |
| H | Cl | H | $OCH_3$ | $CH_3$ | N | |
| H | Cl | H | $OCH_3$ | $OCH_3$ | N | |
| H | Cl | H | $CH_3$ | $C_2H_5$ | N | |
| H | Cl | H | $OCH_3$ | $C_2H_5$ | N | |
| H | Cl | H | $CH_3$ | $OC_2H_5$ | N | |
| H | Cl | H | $OCH_3$ | $OC_2H_5$ | N | |
| H | Cl | H | $CH_3$ | $CH_2OCH_3$ | N | |
| H | Cl | H | $OCH_3$ | $CH_2OCH_3$ | N | |
| H | Cl | H | $OCH_3$ | $NH_2$ | N | |
| H | Cl | H | $OCH_3$ | $NHCH_3$ | N | |
| H | Cl | H | $OCH_3$ | $N(CH_3)_2$ | N | |
| H | Br | H | $CH_3$ | $CH_3$ | CH | |
| H | Br | H | $OCH_3$ | $CH_3$ | CH | |
| H | Br | H | $OCH_3$ | $OCH_3$ | CH | |
| H | Br | H | $CH_3$ | $C_2H_5$ | CH | |
| H | Br | H | $OCH_3$ | $C_2H_5$ | CH | |
| H | Br | H | $CH_3$ | $OC_2H_5$ | CH | |
| H | Br | H | $OCH_3$ | $OC_2H_5$ | CH | |
| H | Br | H | $CH_3$ | $CH_2OCH_3$ | CH | |
| H | Br | H | $OCH_3$ | $CH_2OCH_3$ | CH | |
| H | Br | H | $OCH_3$ | $NH_2$ | CH | |
| H | Br | H | $OCH_3$ | $NHCH_3$ | CH | |
| H | Br | H | $OCH_3$ | $N(CH_3)_2$ | CH | |
| H | Br | H | $CH_3$ | $CH_3$ | N | |
| H | Br | H | $OCH_3$ | $CH_3$ | N | |
| H | Br | H | $OCH_3$ | $OCH_3$ | N | |
| H | Br | H | $CH_3$ | $C_2H_5$ | N | |
| H | Br | H | $OCH_3$ | $C_2H_5$ | N | |
| H | Br | H | $CH_3$ | $OC_2H_5$ | N | |
| H | Br | H | $OCH_3$ | $OC_2H_5$ | N | |
| H | Br | H | $CH_3$ | $CH_2OCH_3$ | N | |
| H | Br | H | $OCH_3$ | $CH_2OCH_3$ | N | |
| H | Br | H | $OCH_3$ | $NH_2$ | N | |
| H | Br | H | $OCH_3$ | $NHCH_3$ | N | |
| H | Br | H | $OCH_3$ | $N(CH_3)_2$ | N | |
| H | $NO_2$ | H | $CH_3$ | $CH_3$ | CH | |
| H | $NO_2$ | H | $OCH_3$ | $CH_3$ | CH | |
| H | $NO_2$ | H | $OCH_3$ | $OCH_3$ | CH | |
| H | $NO_2$ | H | $CH_3$ | $C_2H_5$ | CH | |
| H | $NO_2$ | H | $OCH_3$ | $C_2H_5$ | CH | |
| H | $NO_2$ | H | $CH_3$ | $OC_2H_5$ | CH | |
| H | $NO_2$ | H | $OCH_3$ | $OC_2H_5$ | CH | |
| H | $NO_2$ | H | $CH_3$ | $CH_2OCH_3$ | CH | |
| H | $NO_2$ | H | $OCH_3$ | $CH_2OCH_3$ | CH | |
| H | $NO_2$ | H | $OCH_3$ | $NH_2$ | CH | |
| H | $NO_2$ | H | $OCH_3$ | $NHCH_3$ | CH | |
| H | $NO_2$ | H | $OCH_3$ | $N(CH_3)_2$ | CH | |
| H | $NO_2$ | H | $CH_3$ | $CH_3$ | N | |
| H | $NO_2$ | H | $OCH_3$ | $CH_3$ | N | |
| H | $NO_2$ | H | $OCH_3$ | $OCH_3$ | N | |
| H | $NO_2$ | H | $CH_3$ | $C_2H_5$ | N | |
| H | $NO_2$ | H | $OCH_3$ | $C_2H_5$ | N | |
| H | $NO_2$ | H | $CH_3$ | $OC_2H_5$ | N | |
| H | $NO_2$ | H | $OCH_3$ | $OC_2H_5$ | N | |
| H | $NO_2$ | H | $CH_3$ | $CH_2OCH_3$ | N | |
| H | $NO_2$ | H | $OCH_3$ | $CH_2OCH_3$ | N | |
| H | $NO_2$ | H | $OCH_3$ | $NH_2$ | N | |
| H | $NO_2$ | H | $OCH_3$ | $NHCH_3$ | N | |
| H | $NO_2$ | H | $OCH_3$ | $N(CH_3)_2$ | N | |

TABLE IIIa-continued

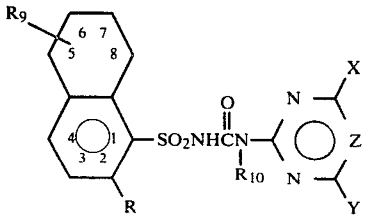

| R9 | R | R10 | X | Y | Z | m.p. (°C.) |
|---|---|---|---|---|---|---|
| H | $OCH_3$ | H | $CH_3$ | $CH_3$ | CH | |
| H | $OCH_3$ | H | $OCH_3$ | $CH_3$ | CH | |
| H | $OCH_3$ | H | $OCH_3$ | OCH | CH | |
| H | $OCH_3$ | H | $CH_3$ | $C_2H_5$ | CH | |
| H | $OCH_3$ | H | $OCH_3$ | $C_2H_5$ | CH | |
| H | $OCH_3$ | H | $CH_3$ | $OC_2H_5$ | CH | |
| H | $OCH_3$ | H | $OCH_3$ | $OC_2H_5$ | CH | |
| H | $OCH_3$ | H | $CH_3$ | $CH_2OCH_3$ | CH | |
| H | $OCH_3$ | H | $OCH_3$ | $CH_2OCH_3$ | CH | |
| H | $OCH_3$ | H | $OCH_3$ | $NH_2$ | CH | |
| H | $OCH_3$ | H | $OCH_3$ | $NHCH_3$ | CH | |
| H | $OCH_3$ | H | $OCH_3$ | $N(CH_3)_2$ | CH | |
| H | $OCH_3$ | H | $CH_3$ | $CH_3$ | N | |
| H | $OCH_3$ | H | $OCH_3$ | $CH_3$ | N | |
| H | $OCH_3$ | H | $OCH_3$ | $OCH_3$ | N | |
| H | $OCH_3$ | H | $CH_3$ | $C_2H_5$ | N | |
| H | $OCH_3$ | H | $OCH_3$ | $C_2H_5$ | N | |
| H | $OCH_3$ | H | $CH_3$ | $OC_2H_5$ | N | |
| H | $OCH_3$ | H | $OCH_3$ | $OC_2H_5$ | N | |
| H | $OCH_3$ | H | $CH_3$ | $CH_2OCH_3$ | N | |
| H | $OCH_3$ | H | $OCH_3$ | $CH_2OCH_3$ | N | |
| H | $OCH_3$ | H | $OCH_3$ | $NH_2$ | N | |
| H | $OCH_3$ | H | $OCH_3$ | $NHCH_3$ | N | |
| H | $OCH_3$ | H | $OCH_3$ | $N(CH_3)_2$ | N | |
| H | $OC_2H_5$ | H | $CH_3$ | $CH_3$ | CH | |
| H | $OCH(CH_3)_2$ | H | $OCH_3$ | $CH_3$ | CH | |
| H | $OCH_2CH_2CH_3$ | H | $OCH_3$ | $OCH_3$ | CH | |
| H | $OC_2H_5$ | H | $CH_3$ | $C_2H_5$ | CH | |
| H | $OC_2H_5$ | H | $OCH_3$ | $C_2H_5$ | CH | |
| H | $OCH(CH_3)_2$ | H | $CH_3$ | $OC_2H_5$ | CH | |
| H | $OC_2H_5$ | H | $OCH_3$ | $OC_2H_5$ | N | |
| H | $OC_2H_5$ | H | $CH_3$ | $CH_2OCH_3$ | N | |
| H | $OCH_2CH_2CH_3$ | H | $OCH_3$ | $CH_2OCH_3$ | N | |
| H | $OCH_2CH_2CH_3$ | H | $OCH_3$ | $NH_2$ | N | |
| H | $OC_2H_5$ | H | $OCH_3$ | $NHCH_3$ | N | |
| H | $OC_2H_5$ | H | $OCH_3$ | $N(CH_3)_2$ | N | |
| H | $SO_2N(CH_3)_2$ | H | $CH_3$ | $CH_3$ | CH | |
| H | $SO_2N(CH_3)_2$ | H | $CH_3$ | $OCH_3$ | CH | |
| H | $SO_2N(CH_3)_2$ | H | $OCH_3$ | $OCH_3$ | CH | |
| H | $SO_2N(C_2H_5)_2$ | H | $CH_3$ | $CH_3$ | CH | |
| H | $SO_2N(C_2H_5)_2$ | H | $CH_3$ | $OCH_3$ | CH | |
| H | $SO_2N(C_2H_5)_2$ | H | $OCH_3$ | $OCH_3$ | CH | |
| H | $SO_2N(CH_3)C_2H_5$ | H | $CH_3$ | $CH_3$ | CH | |
| H | $SO_2N(CH_3)C_2H_5$ | H | $CH_3$ | $OCH_3$ | CH | |
| H | $SO_2N(CH_3)C_2H_5$ | H | $OCH_3$ | $OCH_3$ | CH | |
| H | $SO_2N(CH_3)OCH_3$ | H | $CH_3$ | $CH_3$ | CH | |
| H | $SO_2N(CH_3)OCH_3$ | H | $CH_3$ | $OCH_3$ | CH | |
| H | $SO_2N(CH_3)OCH_3$ | H | $OCH_3$ | $OCH_3$ | CH | |
| H | $OSO_2CF_3$ | H | $CH_3$ | $CH_3$ | CH | |
| H | $OSO_2CF_3$ | H | $CH_3$ | $OCH_3$ | CH | |
| H | $OSO_2CF_3$ | H | $OCH_3$ | $OCH_3$ | CH | |
| H | $OSO_2CH_3$ | H | $CH_3$ | $CH_3$ | CH | |
| H | $OSO_2CH_3$ | H | $CH_3$ | $OCH_3$ | CH | |
| H | $OSO_2CH_3$ | H | $OCH_3$ | $OCH_3$ | CH | |
| H | $OSO_2C_2H_5$ | H | $CH_3$ | $CH_3$ | CH | |
| H | $OSO_2C_2H_5$ | H | $CH_3$ | $OCH_3$ | CH | |
| H | $OSO_2C_2H_5$ | H | $OCH_3$ | $OCH_3$ | CH | |
| H | $SO_2N(OCH_3)CH_3$ | H | $CH_3$ | $OCH_3$ | CH | |
| H | $OSO_2$—n-$C_3H_7$ | H | $CH_3$ | $CH_3$ | CH | |
| H | $OSO_2$—n-$C_3H_7$ | H | $CH_3$ | $OCH_3$ | CH | |
| H | $OSO_2$—n-$C_3H_7$ | H | $OCH_3$ | $OCH_3$ | CH | |
| H | $CO_2CH_3$ | H | $CH_3$ | $CH_3$ | CH | |
| H | $CO_2CH_3$ | H | $CH_3$ | $OCH_3$ | CH | |
| H | $CO_2CH_3$ | H | $OCH_3$ | $OCH_3$ | CH | |
| H | $CO_2C_2H_5$ | H | $CH_3$ | $CH_3$ | CH | |
| H | $CO_2C_2H_5$ | H | $CH_3$ | $OCH_3$ | CH | |
| H | $CO_2C_2H_5$ | H | $OCH_3$ | $OCH_3$ | CH | |
| H | $CO_2$—n-$C_3H_7$ | H | $CH_3$ | $CH_3$ | CH | |
| H | $CO_2$—n-$C_3H_7$ | H | $CH_3$ | $OCH_3$ | CH | |

TABLE IIIa-continued

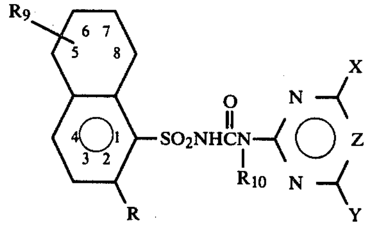

| R9 | R | R10 | X | Y | Z | m.p. (°C.) |
|---|---|---|---|---|---|---|
| H | $CO_2$—n-$C_3H_7$ | H | $OCH_3$ | $OCH_3$ | CH | |
| H | $CO_2$—i-$C_3H_7$ | H | $CH_3$ | $CH_3$ | CH | |
| H | $CO_2$—i-$C_3H_7$ | H | $CH_3$ | $OCH_3$ | CH | |
| H | $CO_2$—i-$C_3H_7$ | H | $OCH_3$ | $OCH_3$ | CH | |
| H | $CO_2CH_2CH{=}CH_2$ | H | $CH_3$ | $CH_3$ | CH | |
| H | $CO_2CH_2CH{=}CH_2$ | H | $CH_3$ | $OCH_3$ | CH | |
| H | $CO_2CH_2CH{=}CH_2$ | H | $OCH_3$ | $OCH_3$ | CH | |
| H | $CO_2CH_2CH_2OCH_3$ | H | $CH_3$ | $CH_3$ | CH | |
| H | $CO_2CH_2CH_2OCH_3$ | H | $CH_3$ | $OCH_3$ | CH | |
| H | $CO_2CH_2CH_2OCH_3$ | H | $OCH_3$ | $OCH_3$ | CH | |
| H | $CO_2CH_2CH_2Cl$ | H | $CH_3$ | $CH_3$ | CH | |
| H | $CO_2CH_2CH_2Cl$ | H | $CH_3$ | $OCH_3$ | CH | |
| H | $CO_2CH_2CH_2Cl$ | H | $OCH_3$ | $OCH_3$ | CH | |
| H | $SO_2CH_3$ | H | $CH_3$ | $CH_3$ | CH | |
| H | $SO_2CH_3$ | H | $CH_3$ | $OCH_3$ | CH | |
| H | $SO_2CH_3$ | H | $OCH_3$ | $OCH_3$ | CH | |
| H | $CH_3$ | H | $OCH_3$ | $OCH_3$ | N | |
| H | $C_2H_5$ | H | $OCH_3$ | $OCH_3$ | N | |
| H | n-$C_3H_7$ | H | $OCH_3$ | $OCH_3$ | N | |
| H | $OCF_2H$ | H | $OCH_3$ | $OCH_3$ | N | |
| H | $OCF_3$ | H | $OCH_3$ | $OCH_3$ | N | |
| H | $OCF_2CF_2H$ | H | $OCH_3$ | $OCH_3$ | N | |
| H | $SCH_3$ | H | $OCH_3$ | $OCH_3$ | N | |
| H | S—n-$C_3H_7$ | H | $OCH_3$ | $OCH_3$ | N | |
| H | $OSO_2CF_3$ | H | $OCH_3$ | $OCH_3$ | N | |
| 5-$CH_3$ | H | H | $CH_3$ | $OCH_3$ | CH | |
| 6-$CH_3$ | H | H | $OCH_3$ | $OCH_3$ | CH | |
| 7-$CH_3$ | H | H | $CH_3$ | $OCH_3$ | N | |
| 8-$CH_3$ | H | H | $OCH_3$ | $OCH_3$ | N | |
| H | H | $CH_3$ | $OCH_3$ | $OCH_3$ | CH | |
| H | H | $CH_3$ | $CH_3$ | $OCH_3$ | CH | |
| H | H | $CH_3$ | $CH_3$ | $OCH_3$ | N | |
| H | H | $CH_3$ | $OCH_3$ | $OCH_3$ | N | |

TABLE IIIb

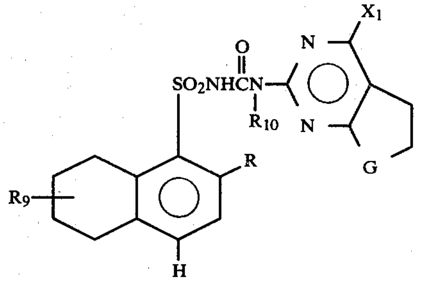

| R9 | R | R10 | G | X1 | m.p.(°C) |
|---|---|---|---|---|---|
| H | H | H | O | $CH_3$ | |
| H | H | H | O | $OCH_3$ | |
| H | H | H | $CH_2$ | $CH_3$ | |
| H | H | H | $CH_2$ | $OCH_3$ | |
| 5-$CH_3$ | H | H | O | $OCH_3$ | |
| H | Cl | H | $CH_2$ | $CH_3$ | |
| H | $CH_3$ | H | O | $CH_3$ | |
| H | H | $CH_3$ | O | $OCH_3$ | |

TABLE IIIc

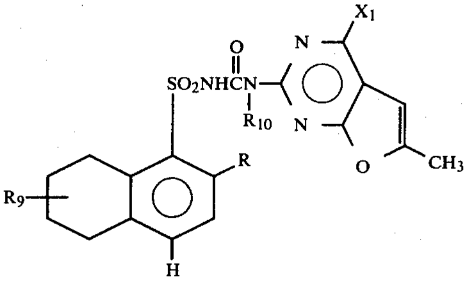

| R9 | R | R10 | X1 | m.p.(°C) |
|---|---|---|---|---|
| H | H | H | $CH_3$ | |
| H | H | H | $OCH_3$ | |
| 5-$CH_3$ | H | H | $CH_3$ | |
| H | Cl | H | $OCH_3$ | |
| H | $CH_3$ | H | $OCH_3$ | |
| H | H | $CH_3$ | $CH_3$ | |

TABLE IIId

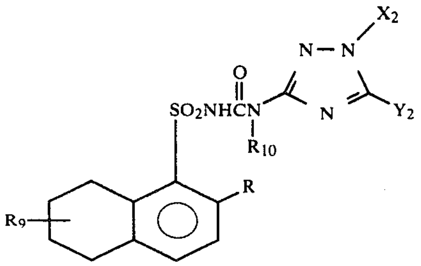

| $R_9$ | R | $R_{10}$ | $X_2$ | $Y_2$ | m.p.(°C.) |
|---|---|---|---|---|---|
| H | H | H | $CH_3$ | $SCH_3$ | |
| H | H | H | $CH_3$ | $OCH_3$ | |
| H | H | H | $CH_3$ | $OC_2H_5$ | |
| H | H | H | $CH_3$ | $SC_2H_5$ | |
| H | H | H | $C_2H_5$ | $OCH_3$ | |
| H | H | H | $C_2H_5$ | $OC_2H_5$ | |
| H | H | H | $C_2H_5$ | $SCH_3$ | |
| H | H | H | n-$C_3H_7$ | $OCH_3$ | |
| H | H | H | $CH_2CF_3$ | $OCH_3$ | |
| H | H | H | $CH_2CF_3$ | $SCH_3$ | |
| 5-$CH_3$ | H | H | $CH_3$ | $OCH_3$ | |
| H | Cl | H | $CH_3$ | $OCH_3$ | |
| H | $CH_3$ | H | $CH_3$ | $OCH_3$ | |
| H | H | $CH_3$ | $CH_3$ | $OCH_3$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE IV

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley & Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 14

Wettable Powder 2,3-dihydro-N-[(4,6-dimethoxypyrimidin-2-yl)aminocarbonyl]-1H-indene-4-sulfonamide 80%
sodium alkylnaphthalenesulfonate 2%
sodium ligninsulfonate 2%
synthetic amorphous silica 3%
kaolinite 13%

The ingredients are blended, hammer-milled until all the solids are essentially under 50 microns, reblended, and packaged.

EXAMPLE 15

Wettable Powder 2,3-dihydro-N-[(4-methoxy-6-methylpyrimidin-2-yl)aminocarbonyl]-1H-indene-4-sulfonamide 50%
sodium alkylnaphthalenesulfonate 2%
low viscosity methyl cellulose 2%
diatomaceous earth 46%

The ingredients are blended, coarsely hammer-milled and then air-milled to produce particles essentially all below 10 microns in diameter. The product is reblended before packaging.

EXAMPLE 16

Granule

Wettable Powder of Example 15 5%
attapulgite granules 95%
(U.S.S. 20–20 mesh; 0.84–0.42 mm)

A slurry of wettable powder containing ≈25% solids is sprayed on the surface of attapulgite granules in a double-cone blender. The granules are dried and packaged.

EXAMPLE 17

Extruded Pellet 2,3-dihydro-N-[(4-methoxy-6-methyl-1,3,5-triazin-2-yl)aminocarbonyl]-1H-indene-4-sulfonamide 25%
anhydrous sodium sulfate 10%
crude calcium ligninsulfonate 5%
sodium alkylnaphthalenesulfonate 1%
calcium/magnesium bentonite 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 18

Oil Suspension 2,3-dihydro-N-[(4,6-dimethoxy-1,3,5-triazin-2-yl)aminocarbonyl]-1H-indene-4-sulfonamide 25%
polyoxyethylene sorbitol hexaoleate 5%
highly aliphatic hydrocarbon oil 70%

The ingredients are ground together in a sand mill until the solid particles have been reduced to under about 5 microns. The resulting thick suspension may be applied directly, but preferably after being extended with oils or emulsified in water.

EXAMPLE 19

Wettable Powder 2,3-dihydro-N-[(4,6-dimethyl-1,3,5-triazin-2-yl)aminocarbonyl]-1H-indene-4-sulfonamide 20%
sodium alkylnaphthalenesulfonate 4%
sodium ligninsulfonate 4%
low viscosity methyl cellulose 3%
attapulgite 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 20

Low Strength Granule 2,3-dihydro-N-[(4,6-dimethylpyrimidin-2-yl)aminocarbonyl]-1H-indene-4-sulfonamide 1%
N,N-dimethylformamide 9%
attapulgite granules 90%
(U.S.S. 20–40 sieve)

The active ingredient is dissolved in the solvent and the solution is sprayed upon dedusted granules in a double cone blender. After spraying of the solution has been completed, the blender is allowed to run for a short period and then the granules are packaged.

EXAMPLE 21

Aqueous Suspension 2,3-dihydro-N-[(4,6-dimethoxypyrimidin-2-yl)aminocarbonyl]-5-nitro-1H-indene-4-sulfonamide 40%
polyacrylic acid thickener 0.3%
dodecylphenol polyethylene glycol ether 0.5%
disodium phosphate 1%
monosodium phosphate 0.5%
polyvinyl alcohol 1.0%
water 56.7%

The ingredients are blended and ground together in a sand mill to produce particles essentially all under 5 microns in size.

EXAMPLE 22

Solution

N-[(4,6-dimethoxypyrimidin-2-yl)aminocarbonyl]-5,6,7,8-tetrahydro-1-naphthalenesulfonamide, sodium salt 5%
water 95%

The salt is added directly to the water with stirring to produce the solution, which may then be packaged for use.

EXAMPLE 23

Low Strength Granule 2,3-dihydro-N-[(4-methoxy-6-methylpyrimidin-2-yl)aminocarbonyl]-5-nitro-1H-indene-4-sulfonamide 0.1%
attapulgite granules 99.9%
(U.S.S. 20–40 mesh)

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 24

Granule 2,3-dihydro-N-[(4,6-dimethoxypyrimidin-2-yl)aminocarbonyl]-5-nitro-1H-indene-4-sulfonamide 80%
wetting agent 1%
crude ligninsulfonate salt (containing 5–20% of the natural sugars) 10%
attapulgite clay 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 25

High Strength Concentrate 2,3-dihydro-N-[(4,6-dimethoxy-1,3,5-triazin-2-yl)aminocarbonyl]-5-nitro-1H-indene-4-sulfonamide 99%
silica aerogel 0.5%
synthetic amorphous silica 0.5%

The ingredients are blended and ground in a hammer-mill to produce a material essentially all passing a U.S.S. No. 50 screen (0.3 mm opening). The concentrate may be formulated further if necessary.

EXAMPLE 26

Wettable Powder 2,3-dihydro-N-[(4-methoxy-6-methyl-1,3,5-triazin-2-yl)aminocarbonyl]-5-nitro-1H-indene-4-sulfonamide 90%
dioctyl sodium sulfosuccinate 0.1%
synthetic fine silica 9.9%

The ingredients are blended and ground in a hammer-mill to produce particles essentially all below 100 microns. The material is sifted through a U.S.S. No. 50 screen and then packaged.

EXAMPLE 27

Wettable Powder

N-[(4,6-dimethoxy-1,3,5-triazin-2-yl)aminocarbonyl]-5,6,7,8-tetrahydro-1-naphthalenesulfonamide 40%
sodium ligninsulfonate 20%
montmorillonite clay 40%

The ingredients are thoroughly blended, coarsely hammer-milled and then air-milled to produce particles essentially all below 10 microns in size. The material is reblended and then packaged.

EXAMPLE 28

Oil Suspension 1-chloro-N-[(4-methoxy-6-methylpyrimidin-2-yl)aminocarbonyl]-3H-indene-4-sulfonamide 35%
blend of polyalcohol carboxylic esters and oil soluble petroleum sulfonates 6%
xylene 59%

The ingredients are combined and ground together in a sand mill to produce particles essentially all below 5 microns. The product can be used directly, extended with oils, or emulsified in water.

EXAMPLE 29

Dust 1-chloro-N-[(4-methoxy-6-methyl-1,3,5-triazin-2-yl)aminocarbonyl]-3H-indene-4-sulfonamide 10%
attapulgite 10%
Pyrophyllite 80%

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- and/or post-emergence weed control in crops, such as cotton, wheat, and barley.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate, acetanilide, dinitroaniline, phenolic and bipyridylium types.

The herbicidal properties of the subject compounds were discovered in a number of greenhouse tests. The test procedures and results follow.

Test A

Seeds of crabgrass (Digitaria sp.), barnyard-grass (*Echinochloa crusgalli*), wild oats (*Avena fatua*), sicklepod (*Cassia obtusifolia*), morningglory (Ipomoea sp.), cockelbur (Xanthium sp.), sorghum, corn, soybean, rice, wheat and nutsedge tubers (*Cyperus rotundus*) were planted in a growth medium and treated pre-emergence with the chemicals dissolved in a non-phytotoxic solvent solution of the compounds of Table A. At the same time, cotton having five leaves (including cotyledonary ones), bush beans with the third trifoliolate leaf expanding, crabgrass, barnyardgrass and wild oats with two leaves, sicklepod with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed with a non-phytotoxic solvent solution of the compounds of Table A. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0=no effect;
10=maximum effect;
A=accelerated growth;
C=chlorosis and/or necrosis;
D=defoliation;
E=emergence inhibition;
G=growth retardation;
H=formative effects;
S=albinism;
U=unusual pigmentation;
X=axillary stimulation;
6Y=abscised buds or flowers; and
6F=delayed flowering.

The data show that the compounds tested are highly active pre- and post-emergence herbicides.
-continued
Table A Structures
Compound 1
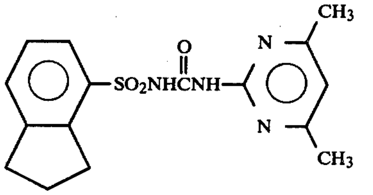
Compound 2
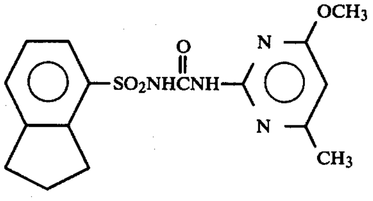
Compound 3
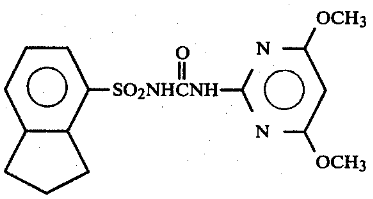
Compound 4
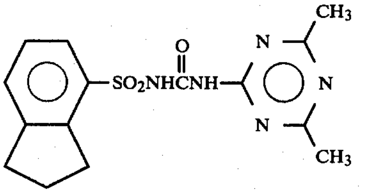
Compound 5
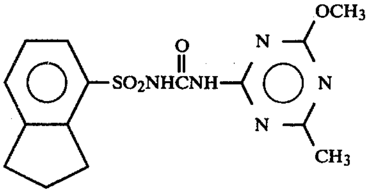
Compound 6
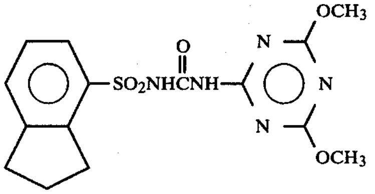
Compound 7
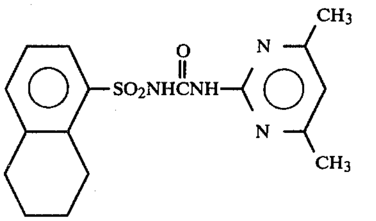
Compound 8
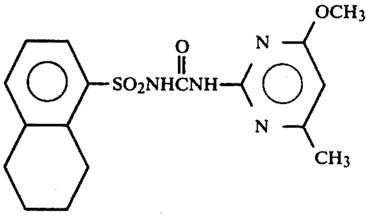
Compound 9
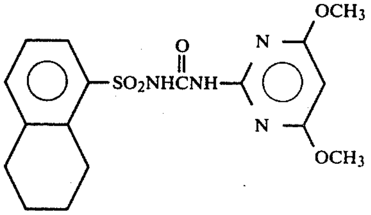
Compound 10
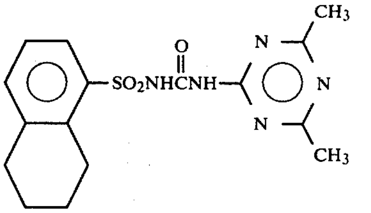
Compound 11
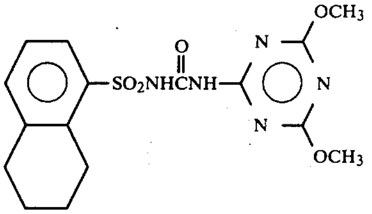
Compound 12
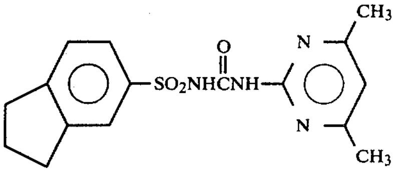
Compound 13
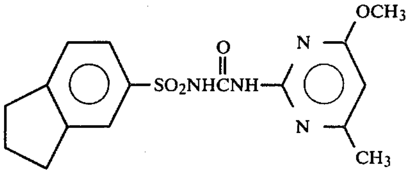
Compound 14
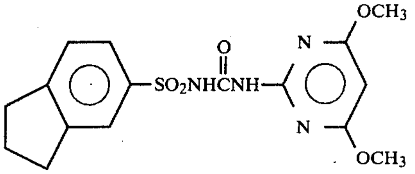

-continued
Table A Structures
Compound 15
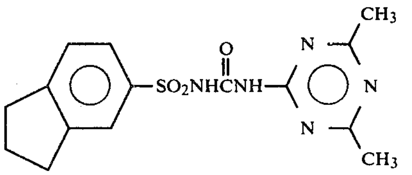
Compound 16
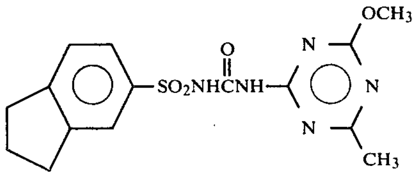
Compound 17
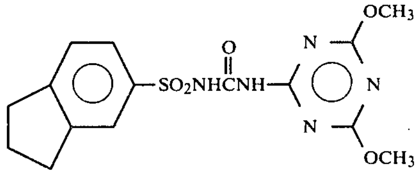
Compound 18
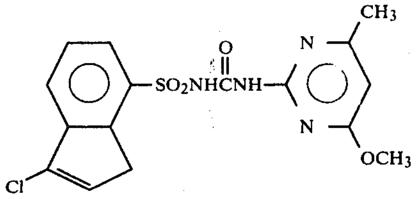
Compound 19
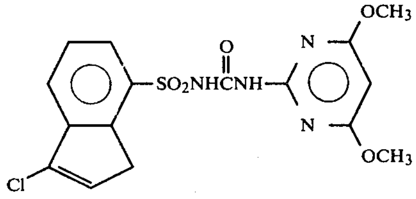
Compound 20
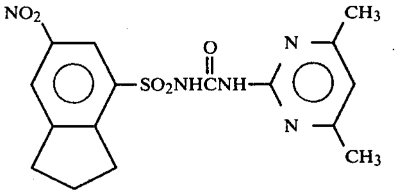
Compound 21
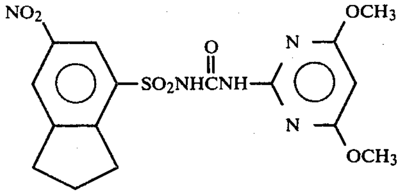
-continued
Table A Structures
Compound 22
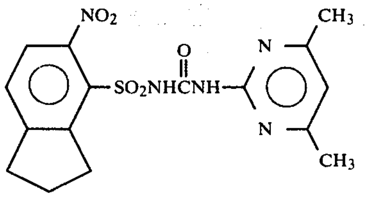
Compound 23
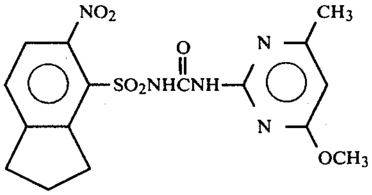
Compound 24
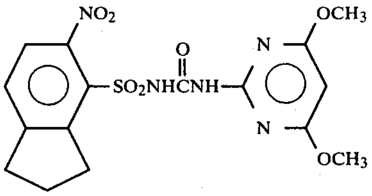
Compound 25
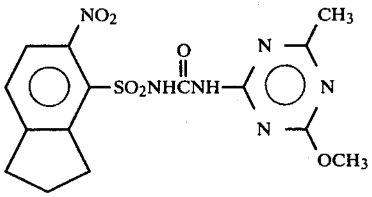
Compound 26
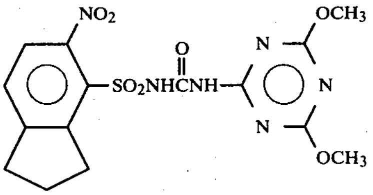
Compound 27
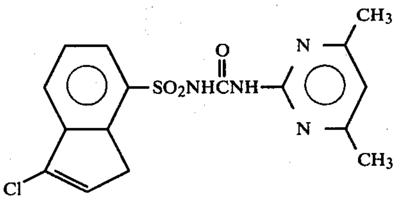
Compound 28
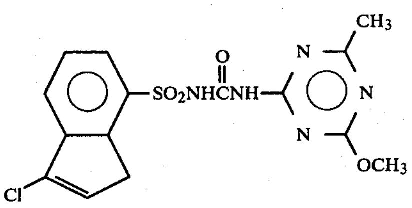

-continued

Table A Structures ompound 29 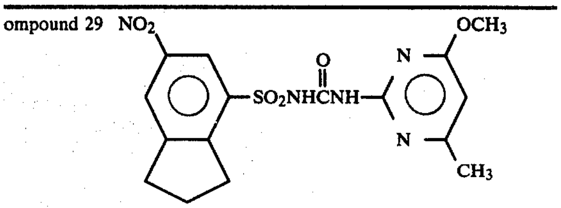

ompound 30 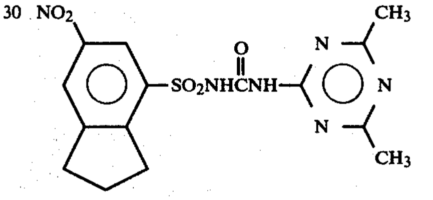

Compound 31 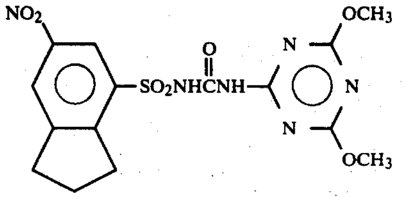

TABLE A

| Rate kg/ha | Cmpd. 1 .05 | Cmpd. 2 .05 | Cmpd. 3 .05 | Cmpd. 4 .05 | Cmpd. 5 .05 | Cmpd. 6 .05 | Cmpd. 7 .05 | Cmpd. 8 .05 | Cmpd. 9 .05 | Cmpd. 10 .05 |
|---|---|---|---|---|---|---|---|---|---|---|
| | | | | | POST-EMERGENCE | | | | | |
| Bush bean | 1C | 6C,8G,6Y | 4S,7G,6Y | 3C,6G,6Y | 5C,7G,6Y | 5C,9G,6Y | 0 | 2C,4G | 3C,7G,6F | 2C |
| Cotton | 1C | 4C,5H,8G | 4C,4H,6G | 1C | 5C,6G | 2C,2H | 0 | 2C | 2C,3G | 0 |
| Morningglory | 0 | 3C,5G | 4C,5G | 1C | 2C,5G | 3C,9G | 0 | 2C | 2C | 0 |
| Cocklebur | 1H | 3C,8G | 4C,9G | 0 | 2C,7G | 2C,6G | 0 | 3G,6F | 3G,6F | 0 |
| Sicklepod | 1C | 3C,8G | 3C,6G | 0 | 2C,3H | 3C,6G | 0 | 1C,1H | 1C,1H | 0 |
| Nutsedge | 5G | 2C,8G | 2C,9G | 0 | 2C | 3G | 0 | 0 | 2G | 0 |
| Crabgrass | 1C,5G | 3C,8G | 1C,5G | 0 | 2G | 3G | 0 | 2G | 2G | 2G |
| Barnyardgrass | 2G | 3C,9H | 2C,7H | 0 | 9H | 3C,7H | 0 | 3C,6H | 2C,6H | 0 |
| Wild Oats | 0 | 2C,5G | 2C | 0 | 0 | 0 | 0 | 1C | 0 | 0 |
| Wheat | 0 | 2C,4G | 0 | 0 | 0 | 0 | 0 | 0 | 0 | 0 |
| Corn | 2C,4G | 2C,9G | 1C,5G | 1C,3G | 5U,9G | 2C,9H | 0 | 3G | 1C,5G | 0 |
| Soybean | 1C | 5C,9G | 2C,4H,9G | 0 | 5C,9G | 5C,9G | 0 | 1C,5H | 2C,8H | 0 |
| Rice | 1C,6G | 5C,9G | 9G | 5G | 6C,9G | 5C,9G | 0 | 4G | 2C,5G | 0 |
| Sorghum | 6G | 3C,9H | 1C,7G | 3G | 3U,9G | 2U,9H | 0 | 2H | 1C,5H | 0 |

| Rate kg/ha | Cmpd. 11 .05 | Cmpd. 12 .05 | Cmpd. 13 .05 | Cmpd. 14 .05 | Cmpd. 15 .05 | Cmpd. 16 .05 | Cmpd. 17 .05 | Cmpd. 18 .05 | Cmpd. 19 .05 | Cmpd. 20 .05 | Cmpd. 21 .05 | Cmpd. 22 .05 |
|---|---|---|---|---|---|---|---|---|---|---|---|---|
| | | | | | | POST-EMERGENCE | | | | | | |
| Bush bean | 5C,9G,6Y | 1C | 1C,2G | 2C,2H | 0 | 1C,6G | 2C,5G,6Y | 2C | 3C,6Y | 5G,6Y | 2C,4H,6Y | 7C,9G, 6Y |
| Cotton | 1C | 0 | 2C | 2C,2H | 0 | 1C | 0 | 0 | 0 | 2G | 1C,3G | 4C,8G |
| Morningglory | 2C,7G | 1H | 2C,3G | 1H | 0 | 1H | 1C | 1C | 2C,5G | 3G | 2C,7G | 3G |
| Cocklebur | 3H,9G | 0 | 3H | 3G,6F | 0 | 1H | 1H | 0 | 5G | 5G | 2C,8G | 9H |
| Sicklepod | 1C,3G | 2A | 2C | 2C,3H | 0 | 2C | 0 | 3C | 3C,6H | 2C | 3C,5G | 2C,4G |
| Nutsedge | 2G | 0 | 2G | 0 | 0 | 0 | 0 | 3G | 3G | 0 | 5G | 5C,9G |
| Crabgrass | 0 | 0 | 2G | 0 | 0 | 0 | 0 | 3G | 2G | 0 | 4G | 2C,7G |
| Barnyardgrass | 1H | 0 | 2G | 1H | 0 | 1C,5H | 2H | 7H | 3C,8H | 3H | 3C,9H | 3C,6H |
| Wild Oats | 0 | 0 | 0 | 0 | 0 | 0 | 0 | 0 | 1C | 0 | 3G | 3C,8G |
| Wheat | 0 | 0 | 0 | 0 | 0 | 0 | 0 | 0 | 0 | 0 | 3G | 3C,8G |
| Corn | 2C,5G 1H | 2H | 3G | 0 | 8H | 4H | 2C | 9H | 2C,5G | 3U,9G | 5U,9G | |
| Soybean | 3C,9G,5X | 2G | 0 | 1C,4G | 0 | 2C,7G | 2C,6G | 2C | 2C,2H | 3G | 2H,5G | 3C,9G |
| Rice | 9G,5I | 2G | 4G | 2G | 0 | 6G | 4G | 1C | 2C,8G | 4G | 2C,8G | 2C,9G |
| Sorghum | 1C,9H | 0 | 1C,5H | 2G | 0 | 2C,9H | 7H | 3C | 3C,7H | 4G | 2C,8H | 3U,9G |

| Rate kg/ha | Cmpd. 23 .05 | Cmpd. 15 Cmpd. 24 .05 | Cmpd. 25 .05 | Cmpd. 26 .05 | Cmpd. 27 .05 | Cmpd. 28 .05 | Cmpd. 45 .05 | Cmpd. 30 .05 | Cmpd. 31 .05 |
|---|---|---|---|---|---|---|---|---|---|
| | | | | POST-EMERGENCE | | | | | |
| Bush bean | 4C,6G,6Y | 4C,7G,6Y | 7C,9G,6Y | 8C,9G,6Y | 2G | 2C,4G | 4C,9G,6Y | 1C,8G,6Y | 1C,8G,6Y |
| Cotton | 3C,9G | 3C,9G | 4C,9G | 3C,9G | 0 | 1C | 3C,7G | 1C,5G | 4B,5D,5G |
| Morningglory | 1C,3G | 2C,7G | 2C,8G | 3C,8G | 1C | 2C,7H | 3C,7G | 1C,3G | 3C,6G |
| Cocklebur | 9C | 10C | 9C | 9C | 0 | 3G | 3C,9G | 1C,8H | 10C |
| Sicklepod | 2C,7G | 5C,9G | 5C,9G | 2C,9G | 1C | 3C | 4C,8G | 1C,3G | 2C,6G |
| Nutsedge | 3C,9G | 9C | 6C,9G | 1C,6G | 0 | 0 | 1C,9G | 3G | 1C,5G |
| Crabgrass | 2C,6H | 2C,7G | 2C,6G | 0 | 0 | 0 | 2C,7G | 1H | 2G |

TABLE A-continued

| | | | | | | | | | |
|---|---|---|---|---|---|---|---|---|---|
| Barnyardgrass | 5C,9H | 9C | 3C,7H | 1C | 1H | 1H | 2C,9H | 0 | 3C,9H |
| Wild Oats | 3C,8G | 2C | 3C,8G | 2G | 0 | 0 | 2C,9G | 0 | 2C,8G |
| Wheat | 3C,9G | 2C,5G | 3C,9G | 3G | 0 | 0 | 2C,9G | 0 | 2C,9G |
| Corn | 9C | 6U,9C | 5U,9C | 2C,8H | 0 | 2C,9H | 3U,9G | 4H | 5U,9H |
| Soybean | 9C | 9C | 4C,9G | 9C | 2G | 2C,5H | 9C | 1C,8G | 9C |
| Rice | 2U,9G | 2C,9G | 5C,9G | 4C,9G | 0 | 9G | 2C,9G | 8G | 6C,9G |
| Sorghum | 9G | 6U,9G | 2U,9G | 2C,7H | 0 | 3C,9H | 1C,9H | 4G | 2C,9H |

| Rate kg/ha | Cmpd. 1 .05 | Cmpd. 2 .05 | Cmpd. 3 .05 | Cmpd. 4 .05 | Cmpd. 5 .05 | Cmpd. 6 .05 | Cmpd. 7 .05 | Cmpd. 8 .05 | Cmpd. 9 .05 | Cmpd. 10 .05 | Cmpd. 10 .05 |
|---|---|---|---|---|---|---|---|---|---|---|---|
| | | | | | PRE-EMERGENCE | | | | | | |
| Morningglory | 5G | 9H | 9G | 5G | 9H | 9G | 0 | 8G | 7G | 2C | 9G |
| Cocklebur | 5G | 8H | 9H | 2H | 9H | 9H | 4H | 9H | 8H | 0 | 9H |
| Sicklepod | 3G | 9G | 8G | 1C | 2C,8G | 2C,8G | 0 | 1C,5G | 2C | 0 | 2C,7G |
| Nutsedge | 0 | 5G | 10E | 5G | 4C,6G | 5G | 0 | 3G | 3G | 0 | 5G |
| Crabgrass | 1C | 2C,5G | 1C,4G | 0 | 1C | 4C | 0 | 2C | 2C,7G | 0 | 2C,4G |
| Barnyardgrass | 2C,6G | 2C,9H | 2C,9H | 2C | 9H | 9H | 0 | 2C,9H | 3C,9H | 1C | 3C,9H |
| Wild Oats | 3C,8G | 2C,9G | 8G | 0 | 2C,6G | 2C,8H | 0 | 2C,8H | 3C,7G | 0 | 2C,9G |
| Wheat | 3C,8G | 2C,9G | 9G | 3G | 8G | 2C,9G | 0 | 2C,9G | 3C,8G | 0 | 2C,9G |
| Corn | 2C,7G | 1C,9G | 2C,8G | 2C | 2C,8G | 2C,8G | 0 | 1C,8G | 2C,8G | 0 | 1C,8G |
| Soybean | 0 | 2C,5H | 3G | 0 | 2C,5H | 2C,7H | 0 | 1C | 1C,1H | 0 | 2C,5H |
| Rice | 2C,6G | 9H | 10E | 5G | 9H | 10E | 0 | 3C,7H | 2C,8H | 1C | 10E |
| Sorghum | 2C,5G | 5C,9H | 3C,9H | 2C,6G | 2U,9G | 2C,9H | 0 | 2C,9G | 9G | 1C | 9G |

| Rate kg/ha | Cmpd. 12 .05 | Cmpd. 13 .05 | Cmpd. 14 .05 | Cmpd. 15 .05 | Cmpd. 16 .05 | Cmpd. 17 .05 | Cmpd. 18 .05 | Cmpd. 19 .05 | Cmpd. 20 .05 | Cmpd.21 .05 | Cmpd. 22 .05 |
|---|---|---|---|---|---|---|---|---|---|---|---|
| | | | | | PRE-EMERGENCE | | | | | | |
| Morningglory | 1C | 2G | 8G | 0 | 6G | 2C,7H | 2C,3H | 8G | 2C | 2C | 6G |
| Cocklebur | 1H | 8G | — | 4G | 8H | 4H | — | 9H | 8H | 9H | 9H |
| Sicklepod | 0 | 2C | 3G | 0 | 6G | 4G | 5C,8H | 8H,2C | 4G | 3G | 7H |
| Nutsedge | 0 | 2G | 5G | 0 | 0 | 0 | 2C,8G | 2C,7G | 0 | 3G | 10E |
| Crabgrass | 0 | 1C,3G | 1C | 0 | 1C | 0 | 2C,6G | 2C,5G | 0 | 4G | 2C |
| Barnyardgrass | 0 | 9H,5C | 8H,3C | 0 | 6G,2C | 2C | 5C,9H | 5C,9H | 0 | 2C,8H | 2C,9H |
| Wild Oats | 0 | 2C,6G | 2C,9H | 0 | 1C | 0 | 3C,9G | 9G | 4G | 2C,5H | 2C,9H |
| Wheat | 0 | 3G | 2C,9H | 0 | 2C,6G | 0 | 2C,8G | 9G | 4G | 3G | 2C,9G |
| Corn | 2G | 3C | 3C,6G | 0 | 4C,8G | 2C,6G | 2C,8G | 2C,8G | 2C,6G | 3C,7G | 3C,9G |
| Soybean | 0 | 0 | 2C,2H | 0 | 2C,3H | 2C | 2C | 1C | 0 | 1H | 9H |
| Rice | 0 | 2C,6H | 2C,8H | 1C | 2C,7H | 2C,9G | 5C,8H | 5C,9H | 2C | 2C,6G | 10E |
| Sorghum | 0 | 2C,6G | 2C,8H | 3G | 2C,8H | 2C,7H | 2C,8H | 3C,8H | 1C,3G | 2C,6G | 10H |

| Rate kg/ha | Cmpd. 23 .05 | Cmpd. 24 .05 | Cmpd. 25 .05 | Cmpd. 26 .05 | Cmpd. 27 .05 | Cmpd. 28 .05 | Cmpd. 29 .05 | Cmpd. 30 .05 | Cmpd. 31 .05 |
|---|---|---|---|---|---|---|---|---|---|
| | | | | PRE-EMERGENCE | | | | | |
| Morningglory | 2C,7G | 8G | 9G | 2C,9G | 2H | 2C,8H | 7G | 1C,5H | 2C,7G |
| Cocklebur | — | 9H | 9H | 9H | 5G | 2C,5G | 9H | 9H | 8H |
| Sicklepod | 2C,8G | 9G | 3C,9G | 2C,9G | 1C | 6H,4C | 7G | 2G | 2C,7G |
| Nutsedge | 10E | 10E | 9G | 10E | 0 | 0 | 9G | 0 | 5G |
| Crabgrass | 2C,6G | 2C,6G | 1C | 0 | 0 | 1C | 2C | 0 | 1C |
| Barnyardgrass | 5C,9H | 5C,9H | 5C,7G | 2C | 0 | 3C,7H | 5C,9H | 0 | 2C,8H |
| Wild Oats | 3C,9H | 2C,8G | 2C,9G | 2C,9H | 0 | 2G | 2C,9G | 1C,5G | 2C,9G |
| Wheat | 6C,9H | 3C,9G | 1C,9G | 3G | 0 | 2C,8G | 2C,8G | 1C | 7G |
| Corn | 10H | 3C,9H | 3C,9G | 1C,8G | 0 | 9G | 9H | 1C,5G | 3C,8G |
| Soybean | 8H | 8H | 3C,8H | 2C,8H | 1H | 1C,1H | 8H | 3C,4H | 2C,9H |
| Rice | 10E | 10E | 10E | 3C,9H | 1C | 4C,9H | 10E | 2C,9H | 6C,9H |
| Sorghum | 9H | 5C,9H | 2C,9H | 2C,6G | 0 | 9H | 4C,9H | 2C,7H | 1C,8H |

In the above tests, certain compounds listed, e.g. compounds 10, 12, show weak activity at 0.05 kg/ha; it is thought they would demonstrate better activity at higher rates of application.

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. It may be seen that several of the compounds tested have utility for selective weed control in cotton and wheat.

TABLE B

PRE-EMERGENCE ON
FALLINGTON SILT LOAM SOIL

| | Compound 2 | | | Compound 3 | | Compound 4 | | Compound 5 | | Compound 6 | | Compound 18 | |
|---|---|---|---|---|---|---|---|---|---|---|---|---|---|
| Rate kg/ha | 0.03 | 0.12 | 0.5 | 0.03 | 0.12 | 0.03 | 0.12 | 0.03 | 0.12 | 0.03 | 0.12 | 0.03 | 0.12 |
| Crabgrass | 3G | 5G,2H | 7G,3H | 4G | 6G,3H | 0 | 0 | 0 | 0 | 0 | 2G | 0 | 0 |
| Barnyardgrass | 5G | 7G | 9G,8C | 5G | 6G | 0 | 2G | 5G | 7G | 2H | 9G,5C | 0 | 4G |
| Sorghum | 6G,2H | 6G,3H | 10C | 3G | 6G | 0 | 5G | 7G,5H | 9G,9C | 9G,9C | 10C | 0 | 5G |
| Wild Oats | 5G | 6G | 4G | 4G | 5G | 0 | 0 | 0 | 5G | 0 | 3G | 0 | 0 |
| Johnsongrass | 5G | 7G,3H | 7G,5H | 4G | 7G | 0 | 0 | 5G | 9G,9C | 3G | 9G,8C | 0 | 0 |
| Dallisgrass | 4G | 6G | 6G,3H | 3G | 3G | 0 | 0 | 0 | 0 | 0 | 0 | 0 | 0 |
| Giant foxtail | 0 | 5G,3H | 7G,3H | 0 | 3G | 0 | 0 | 0 | 0 | 0 | 0 | 0 | 3G,3H |
| Ky. bluegrass | 7G,3H | 9G,9C | 10E | 6G,3H | 9G,9C | 0 | 0 | 5G | 8G,8C | 6G,5C | 8G,7C | 0 | 0 |
| Cheatgrass | 4G | 7G | 7G,3H | 2G | 8G | 0 | 0 | 3G | 7G | 0 | 4G | 0 | 0 |
| Sugar beets | 5G | 9G,9C | 10C | 3G | 7G,5C | 0 | 3G | 6G,6C | 10C | 0 | 6G,5C | 2G | 4G,3H |
| Corn | 3G | 5G | 8G,5H | 0 | 4G | 0 | 2G | 4G | 4G,3H | 4G | 6G,3H | 0 | 0 |
| Mustard | 9G,8C | 9G,9C | 10C | 7G,4C | 9G,9C | 0 | 2G | 8G,7C | 9G,9C | 7G | 8G,5C | 5G,3H | 10C |
| Cocklebur | 2G | 4G | 3G | 0 | 4G | 0 | 0 | 3G | 7G,3C | 0 | 0 | 0 | 0 |
| Pigweed | 5G | 10E | 10C | 5G | 10E | 0 | 0 | 5G | 10E | 0 | 5G | 0 | 8C |
| Nutsedge | 3G | 5G | 0 | 3G | 4G | 0 | 0 | 0 | 4G | 0 | 0 | 0 | 0 |
| Cotton | 0 | 0 | 4G,2H | 3G | 0 | 0 | 0 | 2G | 4G | 0 | 0 | 0 | 0 |
| Morningglory | 3G | 3G | 6G,3H | 0 | 2G | 0 | 0 | 4G | 9G,8C | 2C | 5G,5H | 0 | 3G |
| Sicklepod | 0 | 4G | 5G | 0 | 3G | 0 | 0 | 4G | 8G,3C | 0 | 4G | 0 | 0 |
| Teaweed | 0 | 4G | 5G,3H | 0 | 0 | 0 | 0 | 0 | 7G,3H | 0 | 4G | 0 | 0 |
| Velvetleaf | 3G | 4G | 7G,3H | 3G | 5G,2H | 0 | 0 | 3G | 9G,8C | 4G | 8G,5H | 0 | 0 |
| Jimsonweed | 3G | 8G,3C | 9G,3C | 0 | 6G | 0 | 0 | 6G | 9G,9C | 0 | 4G | 0 | 3G |
| Soybean | 0 | 2G | 6G,5H | 0 | 0 | 0 | 0 | 3G | 7G,5H | 3G | 6G | 0 | 0 |
| Rice | 6G | 8G | 8G,8C | 6G | 7G | 0 | 5G | 7G,3H | 10E | 8G,5H | 9G,9C | 4G,4C | 6G,4C |
| Wheat | 4G | 4G | 5G,3C | 2G | 3G | 0 | 0 | 3G | 5G | 0 | 0 | 0 | 0 |

| | Compound 19 | | Compound 29 | | Compound 8 | | Compound 11 | | Compound 28 | | Compound 31 | | Cmpd. 22 |
|---|---|---|---|---|---|---|---|---|---|---|---|---|---|
| Rate kg/ha | 0.03 | 0.12 | 0.03 | 0.12 | 0.030 | 0.120 | 0.030 | 0.120 | 0.060 | 0.250 | 0.060 | 0.250 | 0.030 |
| Crabgrass | 0 | 3H | 0 | 0 | 0 | 0 | 2G | 4G | 0 | 3G | 0 | 4G | 2G |
| Barnyardgrass | 0 | 3G | 4G | 6G | 0 | 3G | 4G | 5G,3H | 0 | 5G | 0 | 0 | 4G,3H |
| Sorghum | 0 | 3G | 10E | 10E | 0 | 6G,3H | 10C | 10C | — | — | — | — | — |
| Wild Oats | 0 | 2G | 3G | 5G | 0 | 2G | 4G,3C | 4G,3C | 0 | 2G | 0 | 7G,3H | 6G |
| Johnsongrass | 0 | 0 | 0 | 6G,3H | 0 | 3G | 8G,5H | 8G,5H | 4G | 8G,3H | 0 | 9G,5H | 6G |
| Dallisgrass | 0 | 0 | 0 | 0 | 0 | 4G | 2G | 3G | 0 | 2G | 0 | 0 | 3G |
| Giant foxtail | 0 | 2G | 0 | 0 | 0 | 0 | 0 | 3G | 0 | 0 | 0 | 0 | 2G |
| Ky. bluegrass | 0 | 3G | 4G | 7G,5C | 0 | 5G | 7G | 8G | 0 | 5G | 5G | 7G,7C | 5G |
| Cheatgrass | 0 | 2G | 0 | 5G | 0 | 3G | 0 | 3G | 0 | 2G | 3G | 6G | 6G |
| Sugar beets | 0 | 6G,5C | 6G,6C | 8G,7C | 0 | 0 | 4G | 6G,3C | 0 | 8G,8C | 10C | 10C | 6G,6C |
| Corn | 0 | 0 | 5G,2H | 6G,5H | 0 | 4G | 4G,2H | 7G,3H | 0 | 8G,5H | 3G | 6G,3H | 4G,2H |
| Mustard | 3G | 9G,7C | 8G | 9G,9C | 0 | 5G | 8G,5C | 9G,9C | 3G | 9G,3H | 9G,9C | 10C | 8G,3H |
| Cocklebur | 0 | — | 3G | — | 0 | 0 | 3G | 7G | 0 | 0 | 6G,3H | 8G,5H | 5G |
| Pigweed | 5G | 9G,8C | 4G | 9G,8C | 0 | 3G | 4G | 8G,8C | 0 | 10C | 10C | 10C | 5G |
| Nutsedge | 0 | 0 | 3G | 4G | 0 | 0 | 2G | 3G | 0 | 3G | 7G | 7G | 4G |
| Cotton | 0 | 0 | 2G | 4G | 0 | 0 | 4G | 6G,5H | 0 | 4G | 7G,3H | 8G,3H | 3G |
| Morningglory | 0 | 0 | 0 | 4G | 0 | 5G | 7G,5H | 9G,5H | 0 | 9G,3H | 5G | 8G,5C | 5G |
| Sicklepod | 0 | 3G | 3G | 4G | 0 | 2G | 3G | 5G,2C | 0 | 4G | 7G | 9G,5C | 5G |
| Teaweed | 0 | 0 | 0 | 3G | 0 | 0 | 5G,5H | 8G,5H | 0 | 0 | 3G | 6G,3H | 3G |
| Velvetleaf | 0 | 0 | 5G | 7G | 0 | 3G | 6G,5H | 9G,9C | 0 | 0 | 5G,3H | 9G,8C | 3G |
| Jimsonweed | 0 | 0 | 5G | 7G | 0 | 0 | 4G | 7G,5H | 0 | 4G | 4G | 7G,3C | 6G |
| Soybean | 0 | 0 | 3G | 5G | 0 | 2G | 4G | 6G,5H | 0 | 4G | 8G,5H | 9G,5H | 3G |
| Rice | 0 | 7G,3H | 5G | 7G | 0 | 5G | 8G,8C | 10C | 7G,3H | 10C | 5G,3H | 10C | 7G,3H |
| Wheat | 0 | 0 | 3G | 3G | 0 | 0 | 3G | 5G | 2G | 4G | 0 | 4G | 4G |

| | Compound 23 | | Compound 24 | | Compound 25 | | Compound 26 | |
|---|---|---|---|---|---|---|---|---|
| Rate kg/ha | 0.03 | 0.125 | 0.030 | 0.125 | 0.03 | 0.125 | 0.030 | 0.125 |
| Crabgrass | 3G | 3G | 2G | 4G | 0 | 0 | 0 | 0 |
| Barnyardgrass | 5G | 8G,5H | 4G | 9G,5H | 0 | 3G | 0 | 2G |
| Sorghum | — | — | — | — | — | — | — | — |
| Wild Oats | 4G | 5G | 0 | 0 | 5G | 7G | 0 | 3G |
| Johnsongrass | 5G | 6G | 5G | 8G,3H | 4G | 4G,3H | 2G | 3G |
| Dallisgrass | 6G | 4G | 3G | 6G | 0 | 3G | 0 | 0 |
| Giant foxtail | 3G | 5G | 5G | 7G,3H | 0 | 2G | 0 | 2G |
| Ky. bluegrass | 8G,5E | 8G,8C | 5G | 7G,5E | 5G | 6G,5E | 2G | 10E |
| Cheatgrass | 7G,5E | 7G,5E | 4G | 7G,8C | 5G | 6G,5C | 0 | 6G,7C |
| Sugar beets | 5G | 9G,9C | 4G | 9G,9C | 9G,9C | 10C | 5G | 10C |
| Corn | 4G,3H | 7G,5H | 2G | 6G,5H | 3G | 8G,5H | 0 | 5G,2H |
| Mustard | 9G,8C | 10C | 6G,3H | 10C | 8G,8C | 10C | 3G | 9G,9C |
| Cocklebur | 4G | 4G,3H | 2G | 5G,3H | 8G,3H | 7G,5H | — | 7G,5H |
| Pigweed | 9G,8C | 10C | 10E | 10E | 10E | 10E | 5G | 10E |
| Nutsedge | 4G | 8G | 3G | 9G | 6G | 8G | 7G | 10E |
| Cotton | 0 | 0 | 0 | 3G | 5G | 8G,3H | 0 | 5G |
| Morningglory | 3G | 4G | 0 | 4G | 5G | 8G,3H | 0 | 4G |
| Sicklepod | 2G | 4G | 0 | 3G | 6G | 8G,8C | 4G | 6G |
| Teaweed | 0 | 4G | 0 | 3G | 3G | 6G,3H | 0 | 5G,3H |
| Velvetleaf | 3G | 5G,3H | 3G | 4G,3H | 3G,3H | 8G,5H | 0 | 8G,5H |
| Jimsonweed | 5G | 6G | 3G | 7G | 5G | 8G,7C | 0 | 7G |
| Soybean | 3G | 4G | 0 | 2G | 6G,3H | 8G,5H | 0 | 7G,5H |
| Rice | 8G | 8G,3H | 7G | 8G,9C | 8G,3H | 10E | 4G | 8G,8C |

TABLE B-continued

| PRE-EMERGENCE ON FALLINGTON SILT LOAM SOIL | | | | | | | | |
|---|---|---|---|---|---|---|---|---|
| Wheat | 0 | 5G | 0 | 3G | 2G | 4G | 0 | 2G |

Test C

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pensylvanicum*), tumble mustard (*Sisymbrium altissium*) kochia (*Kochia scoparia*), shepherd's purse (*Capsella bursa-pastoris*), *Matricaria inodora*, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treaments were compared to the controls and the effects visually rated. The recorded data are presented in Table C. It may be seen that certain compounds from within the scope of the invention have utility for selective weed control in cereal crops such as wheat and barley.

TABLE C

| | Compound 2 | | | | Compound 3 | | | |
|---|---|---|---|---|---|---|---|---|
| | Pre-Emergence | | Post-Emergence | | Pre-Emergence | | Post-Emergence | |
| Rate kg/ha | 0.015 | 0.06 | 0.015 | 0.06 | 0.015 | 0.06 | 0.015 | 0.06 |
| wheat | 0 | 0 | 0 | 6G | 0 | 0 | 1G | 5G |
| barley | 0 | 0 | 2G | 4G | 0 | 1G | 3G | 3G,2C |
| wild oats | 0 | 0 | 2G | 5G | 0 | 3G | 2G | 3G |
| downy brome | 2G | 8G | 6G | 8G,1C | 3G,1C | 8G | 3G,1C | 7G |
| cheatgrass | 2G | 7G,1C | 7G | 8G | 4G | 7G | 5G,1C | 8G |
| blackgrass | 3G | 8G | 4G | 6G | 4G,1C | 7G | 2G | 6G |
| annual bluegrass | 4G | 8G | 3G | 4G | 8G | 8G | 0 | 3G |
| green foxtail | 3G | 2G,2C | 6G | 7G,1C | 3G | 5G,3C | 7G,1C | 9G,4C |
| quackgrass | 2G | 5G | 4G | 6G,1C | 4G | 4G | 6G | 6G |
| Italian ryegrass | 4G | 5G | 8G | 8G,3C | 4G | 5G | 7G,3C | 7G |
| ripgut brome | 2G | 5G | 8G | 8G,1C | 3G | 5G,1C | 6G | 7G |
| Russian thistle | 0 | 0 | 0 | 0 | 0 | 0 | 0 | 0 |
| tansy mustard | 8G,5C | 9G,9C | 8G,4C | 8G,6C | 9G | 8G | 9G,5C | 10C |
| tumble mustard | 9G,7C | 9G,6C | 8G,4C | 10C | 2G | 9G,4C | 8G,4C | 10C |
| kochia | 4G,2C | 6G | 2G | 3G | 0 | 5G,3C | 0 | 1G,1C |
| shepherd's purse | 8G | 9G | 7G,5C | 8G,5C | 9G | 8G | 8G,3C | 9G,9C |
| *Matricaria inodora* | 7G | 9G | 3G,1C | 7G,2C | 8G | 9G | 2G | 3G,2C |
| black nightshade | 5G | 8G | 4G | 6G,2C | 3G | 7G | 0 | 3G |
| yellow rocket | 8G | 9G | 2G | 6G | 8G | 9G,4C | 0 | 4G |
| wild mustard | 7G,2C | 9G,7C | 10C | 10C | 0 | 8G,5C | 10C | 10C |
| wild buckwheat | 0 | 2G | 0 | 2G | 0 | 1G,2C | 0 | 5G,2C |

| | Compound 5 | | | | Compound 6 | | | |
|---|---|---|---|---|---|---|---|---|
| | Pre-Emergence | | Post-Emergence | | Pre-Emergence | | Post-Emergence | |
| Rate kg/ha | 0.015 | 0.06 | 0.015 | 0.06 | 0.015 | 0.06 | 0.015 | 0.06 |
| wheat | 0 | 0 | 0 | 5G | 0 | 0 | 0 | 3G |
| barley | 0 | 0 | 0 | 0 | 0 | 0 | 0 | 6G |
| wild oats | 0 | 0 | 0 | 2G | 0 | 0 | 0 | 1G |
| downy brome | 2G | 3G | 2G | 5G | 0 | 4G | 2G | 2G |
| cheatgrass | 2G | 5G | 0 | 6G,1C | 0 | 2G | 0 | 4G |
| blackgrass | 3G | 7G | 0 | 2G | 0 | 5G | 0 | 2G |
| annual bluegrass | 4G | 8G | 0 | 5G,2C | 0 | 8G,4C | 0 | 0 |
| green foxtail | 0 | 2G,2C | 0 | 7G | 0 | 2G,1C | 0 | 0 |
| quackgrass | 4C,1C | 7G | 0 | 5G | 0 | 3G,2C | 0 | 1G |
| Italian ryegrass | 5G | 9G | 6G | 8G,5C | 0 | 7G,3C | 4G | 7G,1C |
| ripgut brome | 3G | 5G,1C | 4G | 8G,2C | 0 | 4G,1C | 3G | 6G |
| Russian thistle | 0 | 0 | 0 | 1G,2C | 0 | 0 | 0 | 0 |
| tansy mustard | 7C | 9G,9C | 0 | 10C | 9G | 9C | 6G,4C | 10C |
| tumble mustard | 0 | 7G | 8G,7C | 9G,9C | 10C | 5G | 8G,6C | 9G,9C |
| kochia | 0 | 7G,3C | 5G | 8G,3C | 10C | 4G | 0 | 0 |
| shepherd's purse | 6G | 8G | 8G,3C | 8G,5C | 9G,9C | 9G | 8G,3C | 9G,7C |
| *Matricaria inodora* | 0 | 4G | 1G | 4G,2C | 0 | 2G | 0 | 2G,1C |
| black nightshade | 4G | 7G,3C | 0 | 5G | 0 | 4G | 1G,1C | 1G,1C |
| yellow rocket | 5G | 8G,5C | 2G,1C | 8G,4C | 0 | 3G | 0 | 0 |
| wild mustard | 0 | 8G,5C | 10C | 10C | 0 | 3G | 8G,4C | 10C |
| wild buckwheat | 0 | 3G,1C | 0 | 5G | 0 | 1G | 0 | 2G |

Test D

The test chemicals, dissolved in a non-phytotoxic solvent, were applied in an overall spray to the foliage and surrounding soil of selected plant species. One day after treatment, plants were checked for rapid burn injury. Approximately fourteen days after treatment, all species were visually compared to untreated controls and rated for response to treatment. The rating system was as described previously for Test A. The data are presented in Table D.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species are sometimes added to this standard test in order to evaluate unusual selectivity.

The compounds tested are highly active post-emergence herbicides.

TABLE D

| | Over-the-Top Soil/Foliage Treatment | | | | | | | |
|---|---|---|---|---|---|---|---|---|
| | Compound 2 | | Compound 3 | | Compound 5 | | Compound 6 | |
| Rate kg/ha | 0.063 | 0.016 | 0.063 | 0.016 | 0.063 | 0.016 | 0.063 | 0.016 |
| Soybean | 10C | 8G,3C | 10G,2C | 9G,3C | 10G,4C | 6G | 10G,6C | 8G |
| Velvetleaf | 10C | 9G | 10C | 10C | 9G | 9G | 9G | 8G,2C |
| Sesbania | 10C | 7G,5C | 10C | 8G,2C | 9G,8C | 8G | 7G | 7G |
| Sicklepod | 9G,2C | 8G | 9G,2C | 7G,2C | 9G,3C | 7G | 7G,4C | 6G,2C |
| Cotton | 10G | 7G,2C | 9G,3H | 8G | 9G,1H | 4G | 7G,4C | 6G,2C |
| Morningglory | 9G,2C | 8G | 9G,2C | 7G | 9G,3C | 7G | 8G,4C | 7G |
| Alfalfa | 10C | 10C | 10C | 7G | 10C | 10C | 2G | 0 |
| Jimsonweed | 9G | 0 | 9G | 0 | 0 | 3C | 5C | 5C |
| Cocklebur | 9G,2H | 0 | 9G,2H | — | 9G,2C | 0 | 7G | 4G |
| Sunflower | 9G,2H | 7G,2H | 9G,4H | 7G,4H | 10C | 9G,8C | 8G,6C | 8G,4C |
| Mustard | 10C | 9G,9C | 10C | 10C | 10C | 10C | 9G,7C | 6G |
| Sugar beet | 10C | 5G | 10C | 8G | 10C | 8G,8C | 3G | 3G |
| Corn | 8G,3U | 7G,2H | 7G | 5G,5H | 8G,5C | 8G,4C | 8G,2U | 7G |
| Crabgrass | 2G | 0 | 0 | 0 | 2G | 0 | 0 | 0 |
| Rice | 6G,6C | 0 | 6G | 2G | 6G,8C | 4G | 4G,4C | 4G,4C |
| Nutsedge | 1C | 0 | 2G | 0 | 0 | 0 | 0 | 0 |
| Barnyardgrass | 8G,3C | 3G | 6G | 0 | 8G,8C | 3G | 4G | 4G |
| Wheat | 2G | 0 | 3G | 0 | 0 | 0 | 0 | 0 |
| Giant Foxtail | 4G | 0 | 7G | 2G | 4G | 0 | 0 | 0 |
| Wild Oats | 3G | 1G | 0 | 0 | 0 | 0 | 0 | 0 |
| Sorghum | 7G | 6G,2C | 8G | 4G | 7G,5C | 8G | 5G,3C | 5G |
| Johnsongrass | 7G | 5G | 0 | 3G | 8G,8U | 7G,2U | — | 3G |
| Field Bindweed | 7G,3C | 0 | 6G | 0 | 8G | 6G | 5G | 5G |

What is claimed is:

1. Compounds of the formulae:

I

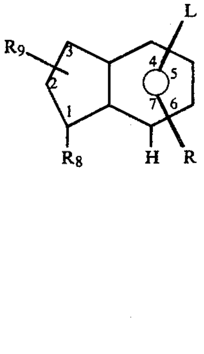

-continued

II

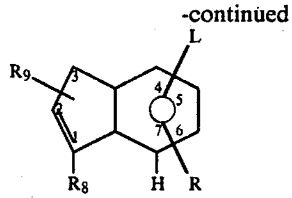

III

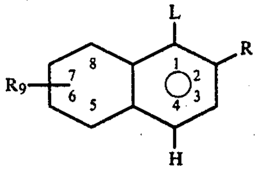

wherein

L is

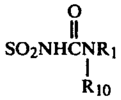

R is H, Cl, Br, $NO_2$, $QR_2$, $CO_2R_3$, $SO_2NR_5R_6$, $SO_2N(OCH_3)CH_3$, $OSO_2R_7$ or $C_1$-$C_3$ alkyl;

$R_2$ is $C_1$-$C_3$ alkyl, $CF_2H$, $CF_3$ or $CF_2CF_2H$;

$R_3$ is $C_1$-$C_3$ alkyl, $CH_2CH{=}CH_2$, $CH_2CH_2OCH_3$ or $CH_2CH_2Cl$;

$R_5$ and $R_6$ are independently $C_1$-$C_2$ alkyl;

$R_7$ is $C_1$-$C_3$ alkyl or $CF_3$;

$R_8$ is H, $CH_3$ or Cl;

$R_9$ is H or $CH_3$;

$R_{10}$ is H or $CH_3$;

Q is O, S or $SO_2$; $R_1$ is

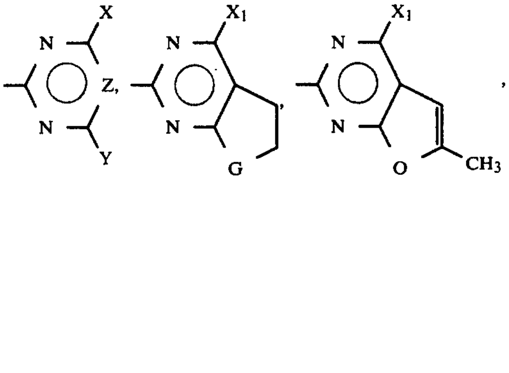

-continued

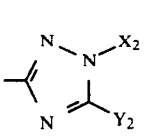 or 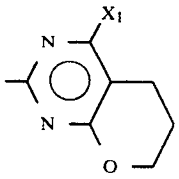

X is $CH_3$, $OCH_3$ or Cl;

Y is $CH_3$, $C_2H_5$, $OCH_3$, $OC_2H_5$, $CH_2OCH_3$, $NH_2$, $NHCH_3$, $SCH_3$, $CH(OCH_3)_2$;

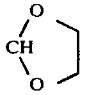

or $N(CH_3)_2$;

Z is CH or N;

$X_1$ is $CH_3$ or $OCH_3$;

G is O or $CH_2$;

$X_2$ is $C_1$–$C_3$ alkyl or $CH_2CF_3$; and $Y_2$ is $SCH_3$, $SC_2H_5$, $OCH_3$ or $OC_2H_5$.

and their agriculturally suitable salts; provided that (1) in Formula I, L is not in the 6-position;

(2) in Formula I, when L is in the 4-position and R is in the 6-position, then R is H, Cl, Br, $NO_2$, $CH_3$ or $OCH_3$;

(3) in Formula II, when $R_8$ is Cl, then R is other than $C_1$–$C_3$ alkyl; and (4) when X is Cl, then Z is CH and Y is $NH_2$, $NHCH_3$, $N(CH_3)_2$ or $OCH_3$.

2. Compounds of claim 1, Formula I.

3. Compounds of claim 1, Formula II.

4. Compounds of claim 1, Formula III.

5. Compounds of claim 2 where L is fixed at the 4-position and $R_9$ is at the 2 or 3 position.

6. Compounds of claim 5 where R is fixed at the 5-position and $R_{10}$ is H.

7. Compounds of claim 6 where $R_1$ is

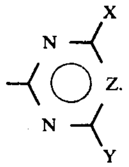

8. Compounds of claim 7 where R is $CO_2CH_3$, $SO_2CH_3$, $SO_2N(CH_3)_2$, Cl, $NO_2$, $OSO_2CH_3$, $OCF_2H$, $SCF_2H$ or H.

9. The compound of claim 1, 2,3-dihydro-N-[(4,6-dimethoxypyrimidin-2-yl)aminocarbonyl]-1H-indene-4-sulfonamide.

10. The compound of claim 1, 2,3-dihydro-N-[(4,6-dimethylpyrimidin-2-yl)aminocarbonyl]-1H-indene-4-sulfonamide.

11. The compound of claim 1, 2,3-dihydro-N-[(4-methoxy-6-methylpyrimidin-2-yl)aminocarbonyl]-1H-indene-4-sulfonamide.

12. The compound of claim 1, 2,3-dihydro-N-[(4,6-dimethoxy-1,3,5-triazin-2-yl)aminocarbonyl]-1H-indene-4-sulfonamide.

13. The compound of claim 1, 2,3-dihydro-N-[(4,6-dimethyl-1,3,5-triazin-2-yl)aminocarbonyl]-1H-indene-4-sulfonamide.

14. The compound of claim 1, 2,3-dihydro-N-[(4-methoxy-6-methyl-1,3,5-triazin-2-yl)aminocarbonyl]-1H-indene-4-sulfonamide.

15. A composition suitable for controlling the growth of undesired vegetation which comprises an effective amount of a compound of claim 1 and at least one of the following: surfactant, solid or liquid diluent.

16. A composition suitable for controlling the growth of undesired vegetation which comprises an effective amount of a compound of claim 2 and at least one of the following: surfactant, solid or liquid diluent.

17. A composition suitable for controlling the growth of undesired vegetation which comprises an effective amount of a compound of claim 3 and at least one of the following: surfactant, solid or liquid diluent.

18. A composition suitable for controlling the growth of undesired vegetation which comprises an effective amount of a compound of claim 4 and at least one of the following: surfactant, solid or liquid diluent.

19. A composition suitable for controlling the growth of undesired vegetation which comprises an effective amount of a compound of claim 5 and at least one of the following: surfactant, solid or liquid diluent.

20. A composition suitable for controlling the growth of undesired vegetation which comprises an effective amount of a compound of claim 6 and at least one of the following: surfactant, solid or liquid diluent.

21. A method for controlling the growth of undesired vegetation which comprises applying to the locus to be protected an effective amount of a compound of claim 1.

22. A method for controlling the growth of undesired vegetation which comprises applying to the locus to be protected an effective amount of a compound of claim 2.

23. A method for controlling the growth of undesired vegetation which comprises applying to the locus to be protected an effective amount of a compound of claim 3.

24. A method for controlling the growth of undesired vegetation which comprises applying to the locus to be protected an effective amount of a compound of claim 4.

25. A method for controlling the growth of undesired vegetation which comprises applying to the locus to be protected an effective amount of a compound of claim 5.

26. A method for controlling the growth of undesired vegetation which comprises applying to the locus to be protected an effective amount of a compound of claim 6.

* * * * *